US011369432B2

(12) United States Patent
Barrish et al.

(10) Patent No.: US 11,369,432 B2
(45) Date of Patent: Jun. 28, 2022

(54) ARRHYTHMIA DIAGNOSTIC AND/OR THERAPY DELIVERY METHODS AND DEVICES, AND ROBOTIC SYSTEMS FOR OTHER USES

(71) Applicant: Project Moray, Inc., Belmont, CA (US)

(72) Inventors: Mark D. Barrish, Belmont, CA (US); Keith Phillip Laby, Oakland, CA (US)

(73) Assignee: Project Moray, Inc., Belmont, CA (US)

(*) Notice: Subject to any disclaimer, the term of this patent is extended or adjusted under 35 U.S.C. 154(b) by 902 days.

(21) Appl. No.: 15/719,120

(22) Filed: Sep. 28, 2017

(65) Prior Publication Data
US 2018/0263688 A1 Sep. 20, 2018

Related U.S. Application Data

(60) Provisional application No. 62/401,001, filed on Sep. 28, 2016.

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/6853* (2013.01); *A61B 5/06* (2013.01);
(Continued)

(58) Field of Classification Search
CPC .............. A61B 18/1492; A61B 5/6853; A61B 2034/2051; A61B 5/0422; A61B 5/06;
(Continued)

(56) References Cited

U.S. PATENT DOCUMENTS 3,284,964 A 11/1966 Saito
3,459,221 A 8/1969 Axelrod
(Continued)

FOREIGN PATENT DOCUMENTS

CN 107835703 3/2018
CN 107835704 3/2018
(Continued)

OTHER PUBLICATIONS approppedia.org , "3-D Printing of Electrically Conductive Materials Literature Review", Appropedia: The sustainability Wiki, By Michigan Tech's Open Sustainability Technology Lab, Jul. 13, 2016, 9 pages.
(Continued)

*Primary Examiner* — Eun Hwa Kim
*Assistant Examiner* — Adam Z Minchella
(74) *Attorney, Agent, or Firm* — Kilpatrick Townsend & Stockton LLP

(57) ABSTRACT

Improved systems for diagnosing and/or treating arrhythmia of a heart makes use of an array of articulation balloons to control movement of a distal portion of a catheter inside the heart, and may be used to align a diagnostic or treatment tool with a target tissue surface region along or adjacent an inner surface of one of the chambers of the heart. The articulation balloons can generate articulation forces at the site of articulation, and the movement may provide greater dexterity than movements induced by transmitting articulation forces proximally along a catheter body that winds through a tortuous vascular pathway. One or more fluid channels may transmit pressure signals that can be used to determine engagement forces between an electrode or other surface near the distal and of an elongate flexible structure and a tissue or other surface, and those same channels may also be used to control inflation of a balloon articulation array, with (Continued)

the pressure signals optionally providing both force and engagement orientation information.

14 Claims, 33 Drawing Sheets

(51) Int. Cl.
| | |
|---|---|
| A61M 25/10 | (2013.01) |
| A61B 5/06 | (2006.01) |
| A61B 17/22 | (2006.01) |
| A61B 34/20 | (2016.01) |
| A61B 17/00 | (2006.01) |
| A61B 5/287 | (2021.01) |

(52) U.S. Cl.
CPC ............. *A61B 5/287* (2021.01); *A61B 5/4836* (2013.01); *A61B 5/686* (2013.01); *A61B 5/6885* (2013.01); *A61B 2017/00318* (2013.01); *A61B 2017/22071* (2013.01); *A61B 2018/141* (2013.01); *A61B 2034/2051* (2016.02); *A61M 25/10184* (2013.11)

(58) Field of Classification Search
CPC ..... A61B 5/4836; A61B 5/686; A61B 5/6885; A61B 2017/00318; A61B 2017/22071; A61B 2018/141; A61M 25/10184
See application file for complete search history.

(56) References Cited

U.S. PATENT DOCUMENTS

| | | | |
|---|---|---|---|
| 3,523,547 A | | 8/1970 | Hatch, Jr. et al. |
| 3,915,194 A | | 10/1975 | Friedrich |
| 3,934,605 A | | 1/1976 | Legris |
| 4,082,324 A | | 4/1978 | Obrecht |
| 4,230,143 A | | 10/1980 | Dettmann et al. |
| 4,494,417 A | | 1/1985 | Larson et al. |
| 4,762,130 A | | 8/1988 | Fogarty et al. |
| 4,784,042 A | * | 11/1988 | Paynter ................ F15B 15/103 92/92 |
| 4,794,912 A | | 1/1989 | Lia |
| 4,838,859 A | | 6/1989 | Strassmann |
| 4,890,611 A | | 1/1990 | Monfort et al. |
| 4,893,613 A | | 1/1990 | Hake |
| 4,900,218 A | | 2/1990 | Sutherland |
| 4,983,165 A | | 1/1991 | Loiterman |
| 5,018,506 A | | 5/1991 | Danna et al. |
| 5,304,132 A | | 4/1994 | Jang |
| 5,308,356 A | | 5/1994 | Blackshear, Jr. et al. |
| 5,337,733 A | | 8/1994 | Bauerfeind et al. |
| 5,413,107 A | | 5/1995 | Oakley et al. |
| 5,469,756 A | | 11/1995 | Feiten |
| 5,489,270 A | | 2/1996 | Van Erp |
| 5,501,667 A | | 3/1996 | Verduin, Jr. |
| 5,529,088 A | | 6/1996 | Asou |
| 5,619,993 A | | 4/1997 | Lee |
| 5,820,595 A | | 10/1998 | Parodi |
| 5,823,955 A | | 10/1998 | Kuck et al. |
| 5,865,801 A | | 2/1999 | Houser |
| 6,066,125 A | | 5/2000 | Webster, Jr. |
| 6,146,339 A | | 11/2000 | Biagtan et al. |
| 6,178,872 B1 | | 1/2001 | Schulz |
| 6,503,194 B2 | | 1/2003 | Pauker |
| 6,527,739 B1 | | 3/2003 | Bigus et al. |
| 6,648,879 B2 | | 11/2003 | Joye et al. |
| 6,811,550 B2 | | 11/2004 | Holland et al. |
| 6,875,170 B2 | | 4/2005 | Francois et al. |
| 6,928,313 B2 | | 8/2005 | Peterson |
| 6,951,226 B2 | | 10/2005 | Eriksson et al. |
| 7,060,062 B2 | | 6/2006 | Joye et al. |
| 7,373,955 B2 | | 5/2008 | Steinberg |
| 7,422,579 B2 | | 9/2008 | Wahr et al. |
| 7,570,981 B2 | | 8/2009 | Peterson |
| 7,578,787 B2 | | 8/2009 | Boese et al. |
| 7,780,723 B2 | | 8/2010 | Taylor |
| 7,824,391 B2 | | 11/2010 | Gesswein |
| 7,850,683 B2 | | 12/2010 | Elkins et al. |
| 7,879,004 B2 | | 2/2011 | Seibel et al. |
| 7,957,790 B2 | | 6/2011 | Kleen |
| 7,963,911 B2 | | 6/2011 | Turliuc |
| 8,125,755 B2 | | 2/2012 | Garcia et al. |
| 8,201,473 B2 | | 6/2012 | Knoll |
| 8,372,055 B2 | | 2/2013 | Thornton et al. |
| 8,388,520 B2 | | 3/2013 | Stefanchik et al. |
| 8,398,540 B2 | | 3/2013 | Hassidov et al. |
| 8,423,115 B2 | | 4/2013 | Koblish et al. |
| 8,469,059 B1 | | 6/2013 | Forst |
| 8,764,725 B2 | | 7/2014 | Averbuch |
| 8,845,523 B2 | | 9/2014 | Lawrence et al. |
| 8,863,608 B2 | | 10/2014 | Fischer et al. |
| 2001/0007070 A1 | | 7/2001 | Stewart et al. |
| 2002/0045929 A1 | | 4/2002 | Diaz |
| 2002/0049408 A1 | | 4/2002 | Van Moorlegem et al. |
| 2002/0058951 A1 | | 5/2002 | Fiedler |
| 2003/0069475 A1 | | 4/2003 | Banik et al. |
| 2006/0058598 A1 | | 3/2006 | Esposito |
| 2006/0084964 A1 | | 4/2006 | Knudson et al. |
| 2006/0106321 A1 | * | 5/2006 | Lewinsky ................ A61B 6/12 600/491 |
| 2006/0235368 A1 | | 10/2006 | Oz |
| 2007/0060997 A1 | | 3/2007 | de Boer |
| 2007/0083193 A1 | * | 4/2007 | Werneth ................ A61B 5/742 606/41 |
| 2007/0100235 A1 | | 5/2007 | Kennedy, II |
| 2007/0123925 A1 | | 5/2007 | Benjamin et al. |
| 2007/0169761 A1 | | 7/2007 | Price |
| 2007/0270686 A1 | | 11/2007 | Ritter et al. |
| 2007/0288095 A1 | | 12/2007 | Wirtel et al. |
| 2008/0091073 A1 | * | 4/2008 | Park ........................ A61B 1/31 600/146 |
| 2008/0215008 A1 | | 9/2008 | Nance et al. |
| 2009/0076584 A1 | | 3/2009 | Mao et al. |
| 2009/0105816 A1 | | 4/2009 | Olsen et al. |
| 2009/0281523 A1 | | 11/2009 | Sacco et al. |
| 2010/0168665 A1 | * | 7/2010 | Skerven ............. A61M 25/1011 604/98.01 |
| 2011/0112632 A1 | | 5/2011 | Chau et al. |
| 2011/0270126 A1 | | 11/2011 | Gunday et al. |
| 2011/0295247 A1 | | 12/2011 | Schlesinger et al. |
| 2011/0295248 A1 | | 12/2011 | Wallace et al. |
| 2012/0271319 A1 | | 10/2012 | Bromander et al. |
| 2012/0296329 A1 | * | 11/2012 | Ng ..................... A61B 18/1492 606/41 |
| 2012/0310227 A1 | | 12/2012 | Katou |
| 2013/0091974 A1 | | 4/2013 | Riwan et al. |
| 2013/0096377 A1 | | 4/2013 | Duindam et al. |
| 2013/0103019 A1 | | 4/2013 | Joye et al. |
| 2013/0178838 A1 | | 7/2013 | Malkowski et al. |
| 2013/0296983 A1 | | 11/2013 | Keller et al. |
| 2014/0062405 A1 | | 3/2014 | Videbaek |
| 2014/0142666 A1 | | 5/2014 | Phelan et al. |
| 2014/0243688 A1 | | 8/2014 | Caron et al. |
| 2014/0276933 A1 | | 9/2014 | Hart et al. |
| 2014/0276934 A1 | | 9/2014 | Balaji et al. |
| 2015/0209558 A1 | | 7/2015 | Charlebois et al. |
| 2015/0265807 A1 | | 9/2015 | Park et al. |
| 2016/0128767 A1 | | 5/2016 | Azamian et al. |
| 2016/0279388 A1 | | 9/2016 | Barrish et al. |
| 2017/0021132 A1 | | 1/2017 | Laby et al. |
| 2017/0021143 A1 | | 1/2017 | Barrish et al. |
| 2017/0157361 A1 | | 6/2017 | Barrish et al. |
| 2017/0157363 A1 | | 6/2017 | Barrish et al. |
| 2017/0189106 A1 | * | 7/2017 | Schuler .................... A61B 5/00 |
| 2018/0071492 A1 | | 3/2018 | Laby et al. |
| 2018/0085559 A1 | | 3/2018 | Laby et al. |

(56) References Cited

U.S. PATENT DOCUMENTS

| | | |
|---|---|---|
| 2018/0200483 A1 | 7/2018 | Laby et al. |
| 2019/0104933 A1* | 4/2019 | Stern ............... A61B 1/307 |

FOREIGN PATENT DOCUMENTS

| | | |
|---|---|---|
| CN | 107921236 | 4/2018 |
| EP | 3274038 | 1/2018 |
| EP | 3274039 | 1/2018 |
| EP | 3274040 | 1/2018 |
| WO | 2007053625 | 5/2007 |
| WO | 2014128507 | 8/2014 |

OTHER PUBLICATIONS

Arsalan et al., "Comparison of Current Costs and Reimbursement for Transcatheter and Surgical Aortic Valve Replacement", J. Am. Coll. Cardiol., vol. 67, No. 13, ACC.i2 Interventional Cardiology, Available online at http://content.onlinejacc.org/article.aspxarticleid=2508037, Apr. 5, 2016, 2 pages.

Atzori et al., "Indoor Navigation System Using Image and Sensor Data Processing on a Smartphone", Optimization of Electrical and Electronic Equipment (OPTIM), 2012 13th International Conference, Available online at https://www.researchgate.net/publication/261267019_Indoor_navigation_system_using_image_and_sensor_data_processing_on_a_smartphone, May 24-26, 2012, pp. 1158-1163.

Au et al., "Microvalves and Micropumps for BioMEMS", Micromachines, vol. 2, ISSN 2072-666X, Available online at www.mdpi.com/journal/micromachines, 2011, pp. 179-220.

Backer et al., "Percutaneous Transcatheter Mitral Valve Replacement", Circulation: Cardiovascular Interventions, Available online at http://circinterventions.ahajournals.org/content/7/3/400.full, 2014, pp. 400-409.

Bar-Cohen , "WorldWide ElectroActive Polymers", EAP (Artificial Muscles) Newsletter, vol. 16, No. 1, (The 31th issue), Available online at http://eap.jpl.nasa.gov, Jun. 2014, pp. 1-18.

BBC News Science & Environment , "Nanotube Yarns Twist Like Muscles", BBC News, Available online at http://www.bbc.co.uk/news/science-environment-15287185, Oct. 14, 2011, 8 pages.

Beahm et al., "Catheter Bonding Technology Overview", Avaialble online at www.beahmdesigns.com, Apr. 2012, 4 pages.

Biswal et al., "Development of an Active Catheter Mechanism Using IPMC for in Vivo Inspection", Journal of Mechatronics and Automation vol. 1, No. 1, Available online at: http://www.academia.edu/10757534/Development_of_an_Active_Catheter_Mechanism_using_IPMC_for_in_vivo_Inspection, 2014, 10 pages.

Bolling , "Can We Predict Mitral Valve Repair Rates by Individual Surgeons' Mitral Volume", Tex Heart Inst J., vol. 38, No. 6, 8th Current Trends in Aortic and Cardiothoracic Surgery, Available online at http://www.ncbi.nlm.nih.gov/pmc/articles/PMC3233323/, 2011, pp. 703-704.

Buntz , "Forget IoT: The Internet of Moving Things Is Where It Is At", Qmed, Available online at http://www.qmed.com/mpmn/medtechpulse/forget-iot-internet-moving-things-where-it, Dec. 10, 2014, 3 pages.

Buntz , "Graphene Breakthrough Could Be a Boon to Flexible Electronics", Electronic Components, Qmed, Available online at http://www.qmed.com/mpmn/medtechpulse/graphene-breakthrough-could-be-boon-flexible-electronicscid=nl.qmed02, Nov. 14, 2013, 1 page.

Buntz , "How Tiny Artificial Muscles Could Be Huge Energy Savers", Motion Control, Qmed, Available online at http://www.qmed.com/mpmn/medtechpulse/how-tiny-artificial-muscles-could-be-huge-energy-saverscid=nl.qmed02.20150223, Feb. 20, 2015, 3 pages.

Buntz , "Using a T-Shirt Printer to Make Medical Circuits", Qmed, Electronic Components, Available online at http://www.qmed.com/mpmn/medtechpulse/using-t-shirt-printer-make-medical-circuits, Nov. 17, 2014, 3 pages.

Catherine et al., "Comparative Review of Endoscopic Devices Articulations Technologies Developed for Minimally Invasive Medical Procedures", Applied Bionics and Biomechanics, vol. 8, 2011, pp. 151-171.

Chakraborty et al., "Mems Micro-Valve for Space Applications", Sensors and Actuators A: Physical, vol. 83, No. 1-3, 2000, pp. 188-193.

Chandgadkar , "An Indoor Navigation System For Smartphones", Available online at http://www.doc.ic.ac.uk/teaching/distinguished-projects/2013/a.chandgadkar.pdf, Jun. 18, 2013, 80 pages.

Chang et al., "Electrostatically-Actuated Reconfigurable Elastomer Microfluidics", Available online at http://people.eecs.berkeley.edu/~maharbiz/HH_paper_mpchang_0008.pdf, 4 pages.

Chen et al., "High-Pressure On-Chip Mechanical Valves for Thermoplastic Microfluidic Devices", The Royal Society of Chemistry, Lab Chip, vol. 9, 2009, pp. 3511-3516.

Clippard New!, "New 7 mm Electronic Valves", Available online at http://www.clippard.com/products/electronic-valve-7mm, 2 pages.

Conrad et al., "Closed Loop Task Space Control of an Interleaved Continuum-Rigid Manipulator", IEEE International Conference on Robotics and Automation, Available online at http://robotics.engr.wisc.edu/cgi-bin/wikiwp/category/continuum-robotics/, 2015, 8 pages.

Corma Inc. , "Corrugators and Pulsating Corrugators", Available online at http://corma.com/products/corrugators-pulsating-corrugators/, 2011, 3 pages.

Coyne , "Comprehensive Manufacturing of Microfluidic Diagnostic Devices", IVD, MDDI Medical Device and Diagnostic Industry, Jun. 17, 2014, 4 pages.

Creganna Tactx Medical , "Deflectable and Steerable Catheter Handbook", Terminology Guide & Design Options, Available online at http://www.creganna.com/wp-content/uploads/Steeringand-DeflectionTerminologyrev3.pdf, 7 pages.

Dabove et al., "Inertial Sensors for Smartphones Navigation", SpringerPlus, vol. 4, No. 834, Available online at http://www.ncbi.nlm.nih.gov/pmc/articles/PMC4695469/, 2015, 18 pages.

D'Arcy et al., "Valvular Heart Disease: The Next Cardiac Epidemic", vol. 97, No. 2, Available online at http://heart.bmj.com/content/97/2/91.extract, 2011, pp. 91-93.

De Sars et al., "A Practical Approach to the Design and Control of Active Endoscopes", Mechatronics, vol. 20, Available online at http://www.elsevierscitech.com/pdfs/Mechatronics_DeSars.pdf, 2010, pp. 251-264.

DMQ Inc. , "Product Datasheet: silQflo™ Silicon Servo Valve", Available online at http://www.dmq-us.com/wp-content/uploads/2015/02/SSV-Datasheet-Rev-1.001.pdf, 2 pages.

Don et al., "Novel Velocity Model to Improve Indoor Localization Using Inertial Navigation With Sensors on a Smart Phone", Avaialble online at http://arxiv.org/pdf/1601.03004.pdf, Jan. 12, 2016, 5 pages.

Dupont et al., "Snakes, Worms and Catheters: Continuum and Serpentine Robots for Minimally Invasive Surgery", IEEE ICRA Full Day Workshop, May 3, 2010, 60 pages.

Eitel , "The Rise of Soft Robots and the Actuators that Drive Them", Available online at http://machinedesign.com/robotics/rise-soft-robots-and-actuators-drive-them, Sep. 12, 2013, 7 pages.

Elveflow Plug & Play , "Microfluidics and Microfluidic Devices: A Review", Available online at http://www.elveflow.com/microfluidic-tutorials/microfluidic-reviews-and-tutorials/microfluidics-and-microfluidic-device-a-review/, 2015, 10 pages.

EP Vantage Ltd. , "Edwards Tightens Transcatheter Valve Stranglehold", Available online at http://www.epvantage.com/Universal/View.aspxtype=Story&id=580885&isEPVantage=yes, Jun. 18, 2015, 2 pages.

Eucog Wiki , "Compliant Robots", Available online at http://www.eucognition.org/eucog-wiki/Compliant_robots, 2012, 5 pages.

Fedak et al., "Evolving Concepts and Technologies in Mitral Valve Repair", American Heart Association, Inc., Contemporary Reviews in Cardiovascular Medicine, vol. 117, No. 7, Available online at http://circ.ahajournals.org/content/117/7/963.full, Feb. 19, 2008, pp. 963-974.

Festo AG & Co. KG , "Systematic Expertise Through Continuous Further Development", Bionic Handling Assistant, Available online at https://www.festo.com/net/supportportal/files/42050/brosch_fc_bha_3_0_en_lo.pdf, Apr. 2012, 6 pages.

(56) References Cited

OTHER PUBLICATIONS

Fite et al., "A Gas-Actuated Anthropomorphic Prosthesis for Transhumeral Amputees", IEEE Transactions on Robotics, vol. 24, No. 1, Feb. 2008, pp. 159-169.
Flexpoint Sensor Systems, Inc. , "The Benefits of Using Bend Sensors", Sensor Products Inc., Available online at www.sensorprod.com, 2 pages.
Fornell , "Transcatheter Mitral Valve Replacement Devices in Development", Diagnostic and Interventional Cardiology, Available online at http://www.dicardiology.com/article/transcatheter-mitral-valve-replacement-devices-development, Dec. 30, 2014, 5 pages.
Fu et al., "Research on the Axis Shape of an Active Catheter", Int. J. Med. Robot.; vol. 4, No. 1, Mar. 2008, pp. 69-76.
Fu et al., "Steerable Catheters in Minimally Invasive Vascular Surgery", Int. J. Med. Robot., vol. 5, No. 4, Dec. 2009, pp. 381-391.
Gionata et al., "An Inertial and Qr Code Landmarks-Based Navigation System for Impaired Wheelchair Users", Available online at https://www.researchgate.net/publication/261551014_An_inertial_and_QR_code_landmarks-based_navigation_system_for_impaired_wheelchair_users, May 29, 2014, pp. 205-214.
Grube , "Development of a TMVR Device Challenge to Innovators", ICI meeting, Dec. 13-15, 2015, 30 pages.
Haga et al., "Active Bending Catheter and Endoscope Using Shape Memory Alloy Actuators", Available online at www.intechopen.com, Shape Memory Alloys, 2010, 21 pages.
Haga et al., "Multi-Functional Active Catheter", Available online at http://bdml.stanford.edu/twiki/pub/Haptics/DesignReferencesSummer2009/MultifunctionalActiveCatheter.pdf, pp. 147-186.
Herrmann et al., "Novel Transcatheter Approaches", Heart Valve Summit, American association of Thoracic surgery, Available online at http://aats.org/multimedia/files/valve/2015/Presentations/Thursday/600-Herrmann.pdf, 2015, 26 pages.
Ikeuchi et al., "Development of Pressure-Driven Micro Active Catheter using Membrane Micro Emboss Following Excimer Laser Ablation (MeME-X) Process", IEEE International Conference on Robotics and Automation, Available online at http://ir.nul.nagoya-u.ac.jp/jspui/bitstream/2237/13924/1/ICRA09_MeMEX.pdf, May 12-17, 2009, pp. 4469-4472.
Jagadeesan , "Design and Control of an Active Catheter", Available online at http://scholar.harvard.edu/jayender/activecatheter, Jul. 14, 2016, 2 pages.
Jia et al., "Online Camera-Gyroscope Auto-Calibration for Cell-phones", IEEE Transactions on Image Processing, Available online at http://users.ece.utexas.edu/~bevans/papers/2015/autocalibration/autocalibrationIEEETransImageProcPaperDraft.pdf, 2013, 11 pages.
John Muir Health , "U.S. Aortic Stenosis Disease Prevalence and Treatment Statistics", Facts and Figures, Available Online at https://www.johnmuirhealth.com/services/cardiovascular-services/intervention/transcatheter-aortic-valve-replacement/facts-and-figures.html, 2016, 3 pages.
Johnson , "Modeling of Frictional Gas Flow in a Piezoelectrically Actuated High-pressure Microvalve for Flowrate Control", Dec. 16, 2005, 197 pages.
Jung et al., "A Modeling Approach for Continuum Robotic Manipulators: Effects of Nonlinear Internal Device Friction", IEEE/RSJ International Conference on Intelligent Robots and Systems, Sep. 25-30, 2011, pp. 5139-5146.
Kasahara et al., "Surface Modification of Polyethylene Terephthalate (PET) by 172-nm Excimer lamp", Technical paper, 2012, pp. 47-54.
Kato et al., "An Inchworm Type In-Pipe Mobile Microrobot Driven by Three Gas-liquid Phase-change Actuators", Proceedings of the Annual Meeting—American Society for Precision Engineering, 2003, pp. 295-298.
Kim et al., "Materials for Multifunctional Balloon Catheters with Capabilities in Cardiac Electrophysiological Mapping and Ablation Therapy", Nat Mater., vol. 10, No. 4, Available online at http://www.ncbi.nlm.nih.gov/pmc/articles/PMC3132573/, Apr. 2011, pp. 316-323.
Kirby et al., "Microfluidic Routing of Aqueous and Organic Flows at High Pressures: Fabrication and Characterization of Integrated Polymer Microvalve Elements", The Royal Society of Chemistry, Lab Chip, vol. 5, 2005, pp. 184-190.
Korane , "Robot Imitates an Elephant's Trunk", Available online at http://machinedesign.com/robotics/robot-imitates-elephant-s-trunk, Sep. 13, 2010, 5 pages.
LabSmith, Inc. , "LabSmith uProcess™ System", LabSmith, Inc., Microfluidic Automation, Available online at http://www.labsmith.com/products/LabSmith_uProcess_Brochure.pdf_ga=1.142274551.472763250.1458083262., 2015, 6 pages.
Langelaar et al., "Modeling of a Shape Memory Alloy Active Catheter", 45th AIAA/ASME/ASCE/AHS/ASC Structures, Structural Dynamics & Materials Conference, American Institute of Aeronautics and Astronautics, Available online at http://citeseerx.ist.psu.edu/viewdoc/downloaddoi=10.1.1.125.1080&rep=rep1&type=pdf, Apr. 19-22, 2004, 16 pages.
Lee et al., "Fabrication, Characterization, and Computational Modeling of a Piezoelectrically Actuated Microvalve for Liquid Flow Control", Journal of Microelectromechanical Systems, vol. 15, No. 3, IEEE, Jun. 2006, pp. 686-696.
Levy , "Tiny Ultrasound Camera Images Blood Vessel Interior in 3-D", Medical Imaging, Qmed, Available online at http://www.qmed.com/mpmn/medtechpulse/tiny-ultrasound-camera-images-blood-vessel-interior-3-dcid=nl.qmed02, Mar. 3, 2014, 5 pages.
Maglione et al., "Ultra-High-Pressure Balloon Angioplasty for Treatment of Resistant Stenoses Within or Adjacent to Previously Implanted Pulmonary Arterial Stents", Circulation: Cardiovascular Interventions, Available online at http://circinterventions.ahajournals.org/content/2/1/52.full, 2009, pp. 52-58.
Malek et al., "Femtosecond Laser Machining and Lamination for Large-Area Flexible Organic Microfluidic Chips", European Physical Journal: Applied Physics, EDP Sciences, Available online at https://hal.archives-ouvertes.fr/hal-00480155/document, Apr. 2009, 8 pages.
Mazzarese , "Low-Profile Balloon Catheters are Critical to TAVR's Success", Medical Tubing Types by MDDI Staff, Available online at http://www.mddionline.com/article/low-profile-balloon-catheters-are-critical-tavr-success-10-21-2014cid=nl.mddi01.20141023, Oct. 21, 2014, 3 pages.
MDDI, Medical Plastics , "The Effect of Extrusion and Blow Molding Parameters on Angioplasty Balloon Production", Available online at http://www.mddionline.com/article/effect-extrusion-and-blow-molding-parameters-angioplasty-balloon-production, May 1, 1998, 4 pages.
Medtronic , "CoreValve™ System", Transcatheter Aortic Valve Delivery Catheter System Compression Loading System, 2014, 61 pages.
Messenger , "A Comprehensive Guide to the U.S. TAVR Market: Surveying the Field", Available online at http://www.meddeviceonline.com/doc/a-comprehensive-guide-to-the-u-s-tavr-market-surveying-the-field-0001, Apr. 12, 2016, 7 pages.
Mohty et al., "Valvular Heart Disease in Elderly Adults", Available online at http://www.uptodate.com/contents/valvular-heart-disease-in-elderly-adults, 2016, 6 pages.
Mount Sinai Hospital , "Researchers Compare Two-Year Clinical Outcomes of Mitral Valve Replacement and Repair in Treating Severe Valve Regurgitation", Icahn School of Medicine at Mount Sinai, Available online at http://www.mountsinai.org/about-us/newsroom/press-releases/researchers-compare-twoyear-clinical-outcomes-of-mitral-valve-replacement-and-repair-, Nov. 9, 2015, 2 pages.
Mueller et al., "An Overview of MEMS-based Micropropulsion Developments at JPL", Acta Astronautica, vol. 52, No. 9-12, Selected Proceedings of the 3rd IAA International Symposium on Small Satellites for Earth Observation, May-Jun. 2003, 15 pages.
Mueller et al., "Design and Fabrication of MEMS-Based Micropropulsion Devices at JPL", Proceedings of SPIE vol. 4558, 2001, pp. 57-71.
Muller et al., "Remote Control Catheter Navigation: Options for Guidance Under MRI", Journal of Cardiovascular Magnetic Resonance, vol. 14, No. 33, Available online at http://www.jcmr-online.com/content/14/1/33, 2012, pp. 1-9.

(56) References Cited

OTHER PUBLICATIONS

Newmarker, "How Lasers are Changing MedTech", Lasers, Qmed, Available online at http://www.qmed.com/mpmn/medtechpulse/how-lasers-are-changing-medtechcid=nl.qmed02, Jan. 14, 2014, 3 pages.
Newmarker, "How Scotch Tape is Driving Diagnostics Breakthroughs", Medical Plastics, Qmed, Available online at http://www.qmed.com/mpmn/medtechpulse/how-scotch-tape-driving-diagnostics-breakthroughscid=nl.qmed02.20141002, Oct. 1, 2014, 3 pages.
Nolker et al., "Differences in Tissue Injury and Ablation Outcomes in Atrial Fibrillation Patients—Manual versus Robotic Catheters", Journal of Atrial Fibrillation, Department of Cardiology, Heart and Diabetes Center, vol. 6, No. 2, Aug.-Sep. 2013, pp. 82-88.
Nucryovascular, LLC, "Peripheral Dilatation Catheter Peripheral Dilatation System", Vascular solutions, PolarCath™ over-the-wire, Available online at www.vasc.com, pp. 1-12.
Oh et al., "A Review of Microvalves", Topical Review, Journal of Micromechanics and Microengineering, vol. 16, 2006, pp. R13-R39.
Omed Qualified Suppliers, "A Tiny Spectrometer that Costs 10 Bucks", Qmed, Available online at http://www.qmed.com/mpmn/medtechpulse/tiny-spectrometer-costs-10-buckscid=nl.qmed02.20141216, Dec. 12, 2014, 3 pages.
Omed Qualified Suppliers, "How 3-D Printing Can Help Accelerate Fluidic Manifold Delivery", Qmed, Available online at http://www.qmed.com/mpmn/medtechpulse/how-3-d-printing-can-help-accelerate-fluidic-manifold-deliverycid=nl.qmed02.20150507, May 6, 2015, 3 pages.
Omed Qualified Suppliers, "Introducing 3-D Injection Molding", Qmed, Available online at http://www.qmed.com/mpmn/gallery/image/4-introducing-3-d-injection-molding, 2014, 2 pages.
Omed Qualified Suppliers, "Overcoming Engineering Challenges: Developing a Tiny Robotically Steerable Guidewire", Qmed, Medtech Pulse Blog, Available online at http://www.qmed.com/mpmn/medtechpulse/overcoming-engineering-challenges-developing-tiny-robotically-steerable-guidewirecid=nl_qmed_daily, Feb. 15, 2013, 2 pages.
Ono et al., "Development of a Cylinder Type Gas-liquid Phase-change Actuator", 2 pages.
Parmar, "FDA Approves St. Jude Medical's Force-Sensing Ablation Catheters for AF", Regulatory and Compliance, MDDI Medical Device and Diagnostic Industry, Available online at http://www.mddionline.com/article/fda-approves-st-jude-medicals-force-sensing-ablation-catheters-af-102714cid=nl.mddi01.20141028, Oct. 27, 2014, 3 pages.
Peelsil™ Tubing, "Scientific Tubing", SGE, Glass Lined Tubing (GLT™), Available online at www.sge.com, Fused Silica Tubing brochure PD-0230-Aw, 2001, 6 pages.
Penning et al., "A Combined Modal-Joint Space Control Approach for Minimally Invasive Surgical Continuum Manipulators", Advanced Robotics, vol. 28, No. 16, Jul. 2014, 41 pages.
Penning et al., "An Evaluation of Closed-Loop Control Options for Continuum Manipulators", IEEE, 2012, 6 pages.
Penning, "ICRA 2012 Recap", Available online at http://robotics.engr.wisc.edu/cgi-bin/wikiwp/2012/11/icra-2012-recap/, Nov. 11, 2012, 2 pages.
Penning et al., "Towards Closed Loop Control of a Continuum Robotic Manipulator for Medical Applications", IEEE, 2011, 6 pages.
Plastics, "Corrugator Technologies: Overview and New Developments", Corrugator technologies overview, Available at http://www.plastics.gl/extrusion-profile/corrugator-technologies-overview/, 2015, 8 pages.
Pollock, "Bionic Ants Could be Tomorrow's Factory Workers", Available online at http://www.reuters.com/article/2015/03/30/us-germany-bionic-ants-idUSKBN0MQ1WD20150330, Mar. 30, 2015, 3 pages.
Preston-Maher et al., "A Technical Review of Minimally Invasive Mitral Valve Replacements", Cardiovascular Engineering and Technology, vol. 6, No. 2, Jun. 2015, pp. 174-184.

Profilepipe Machinery Inc., "Convoluted Tubing to an Outer Diameter of 65 mm", Available online at http://www.profilepipe.com/small_corrugators.html, 2015, 2 pages.
Qmed Qualified Suppliers, "Tiny Artificial Muscles", Available online at http://www.qmed.com/mpmn/gallery/image/1-tiny-artificial-muscles, Jul. 14, 2016, 1 page.
Qmed, Electronic Components, "How Micro-Location Could Boost Healthcare IoT", Available online at http://www.qmed.com/mpmn/medtechpulse/how-micro-location-could-boost-healthcare-iotcid=nl.x.qmed02.edt.aud.qmed.20160606, Jun. 3, 2016, 2 pages.
Quero et al., "A Novel Pressure Balanced Microfluidic Valve", Proc. ISCAS, IEEE, 2002, pp. 1-4.
Rich et al., "Costs for Mitral Valve Surgery According to STS Preoperative Risk: Implications for Transcatheter Mitral Therapies", American Association for Thoracic Surgery, Available Online at http://aats.org/mitral/abstracts/2015/P165.cgi, 2016, 2 pages.
Roriz et al., "Fiber Optic Intensity-Modulated Sensors: A Review in Biomechanics", Photonic Sensors, vol. 2, No. 4, 2012, pp. 315-330.
Rossiter et al., "Printing 3D Dielectric Elastomer Actuators for Soft Robotics", SPIE Proceedings, vol. 7287, Apr. 6, 2009, 2 pages.
Schut, "Corrugator Vacuum Forming", Plastics Technology, Available online at http://www.ptonline.com/articles/'corrugator-vacuum-forming', Jul. 2005, 4 pages.
SGE Analytical Science, "Tubing, Stainless Steel Tubing and Terry-Tool Tubing Cutter", 2011, 10 pages.
Shoa et al., "Conducting Polymer Based Active Catheter for Minimally Invasive Interventions inside Arteries", Conf Proc IEEE Eng Med Biol Soc, Available online at http://mm.ece.ubc.ca/mediawiki/images/b/b7/PID616280.pdf, 2008, pp. 2063-2066.
Sparkfun, "Accelerometer, Gyro and IMU Buying Guide", Available online at https://www.sparkfun.com/pages/accel_gyro_guide, accessed from the internet on Jul. 14, 2016, 10 pages.
Strickland, "Inside an MRI, a Non-Metallic Robot Performs Prostate Surgery", Available online at http://spectrum.ieee.org/automaton/robotics/medical-robots/inside-an-mri-a-nonmetallic-robot-performs-prostate-surgery, Jul. 8, 2015, 3 pages.
Takizawa et al., "Development of a Microfine Active Bending Catheter Equipped with MIF Tactile Sensors", Available online at http://www.ics.forth.gr/bioloch/internal/papers/Olympus.pdf, 1999, 7 pages.
Taramasso et al., "Current Challenges in Interventional Mitral Valve Treatment", J. Thorac. Dis., vol. 7, No. 9, Available online at http://www.ncbi.nlm.nih.gov/pmc/articles/PMC4598533/, 2015, pp. 1536-1542.
Teleflex Incorporated, "Balloons and Balloon Catheters", Available online at http://www.teleflexmedicaloem.com/diagnostic-and-interventional-catheters/balloon-catheters/, 2015, 3 pages.
Temiz et al., "Lab-on-a-Chip Devices: How to Close and Plug the Lab", Microelectronic Engineering, vol. 132, 2015, pp. 156-175.
Tokai Medical Products Inc., "PTA Sphere-Curve", Available online at http://www.tokaimedpro.co.jp/en/products/2009/000056.html, Jul. 14, 2016, 2 pages.
Tung et al., "Laser-Machined Shape Memory Alloy Actuators for Active Catheters", Mechatronics, IEEE/ASME Transactions on, vol. 12, No. 4, Aug. 2007, pp. 439-446.
Van Oosten et al., "Printed Artificial Cilia from Liquid-crystal Network Actuators Modularly Driven by Light", Nature Materials, vol. 8, Available online at http://www.nature.com/nmat/journal/v8/n8/full/nmat2487.html, 2009, pp. 677-682.
Veeramani, "A Transformative Tool for Minimally Invasive Procedures: Design, Modeling and Real-time Control of a Polycrystalline Shape Memory Alloy Actuated Robotic Catheter", 2009, 198 pages.
Walters, "Gas-Flow Calculations: Don't Choke", Applied Flow Technology, Chemical Engineering, Available online at http://www.aft.com/documents/AFT-CE-Gasflow-Reprint.pdf, Jan. 2000, 8 pages.
Wasserman, "Edwards and Medtronic Turn up TAVR Competition with Positive Study Data", Available online at http://www.fiercemedicaldevices.com/story/edwards-and-medtronic-turn-tavr-competition-positive-study-data/2015-03-16, Mar. 16, 2015, 3 pages.
Webb et al., "Transcatheter Aortic Valve Implantation: The Evolution of Prostheses, Delivery Systems and Approaches", Archives of Cardiovascular Disease, vol. 105, 2012, pp. 153-159.

(56) References Cited

OTHER PUBLICATIONS

Weber et al., "Side-Selective Atrial Transseptal Laser Puncture", The Journal of Innovations in Cardiac Rhythm Management, vol. 4, Avaiable online at http://www.innovationsincrm.com/cardiac-rhythm-management/2013/december/524-side-selective-atrial-transseptal-laser-puncture, Dec. 2013, pp. 1481-1485.

Wirtl et al., "White Paper Piezo Technology in Pneumatic Valves", Festo AG & Co. KG, 2014, pp. 1-9.

Wood, "Early Results for Transcatheter Mitral Valve Replacement Reveal Complications and Challenges for the Long Road Ahead", Available online at http://www.tctmd.com/show.aspxid=133937, Feb. 22, 2016, 1 pages.

Wutzler et al., "Robotic Ablation of Atrial Fibrillation", Department of Cardiology, . Vis. Exp. (99), e52560, Available online at http://www.jove.com/video/52560/robotic-ablation-of-atrial-fibrillation, 2015, 14 pages.

Yang et al., "Leak-Tight Piezoelectric Microvalve for High-Pressure Gas Micropropulsion", Journal of Microelectromechanical Systems, vol. 13, No. 5, IEEE, Available Online at http://web.stevens.edu/ses/documents/fileadmin/documents/pdf/JMEMS_hp_valve.pdf, Oct. 2004, pp. 799-807.

Yarbasi et al., "On the Design of a Continuum Robot with Extendable Balloons", Department of Mechanical Engineering, 2015, 1 page.

You et al., "A Doubly Cross-Linked Nano-Adhesive for the Reliable Sealing of Flexible Microfluidic Devices", Lab Chip., vol. 13, No. 7, Available online at http://www.ncbi.nlm.nih.gov/pubmed/23381132, Apr. 2013, pp. 1266-1272.

* cited by examiner

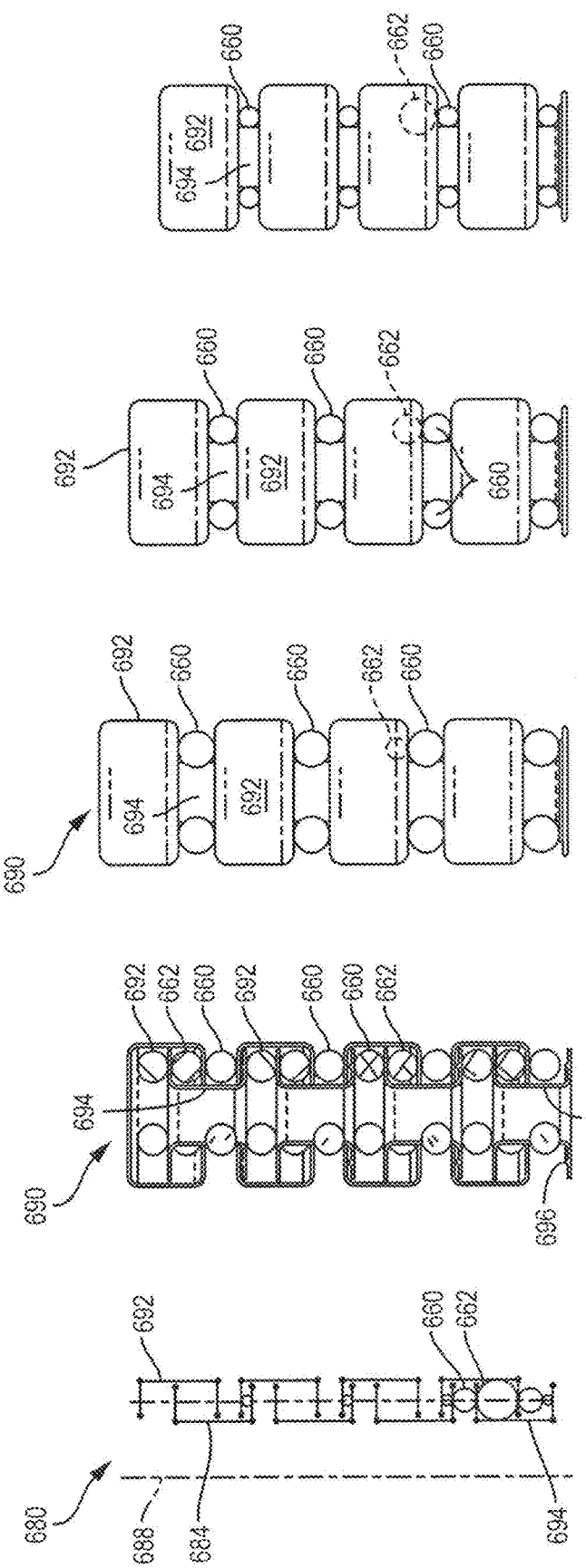

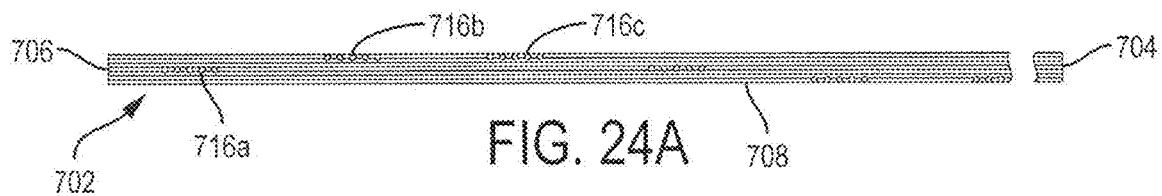
FIG. 24A
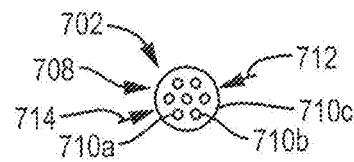
FIG. 24B
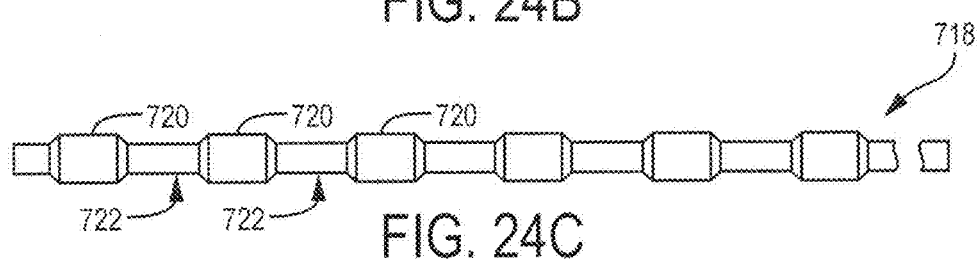
FIG. 24C
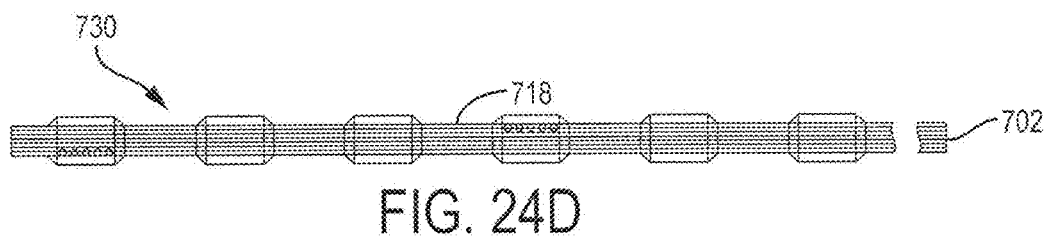
FIG. 24D
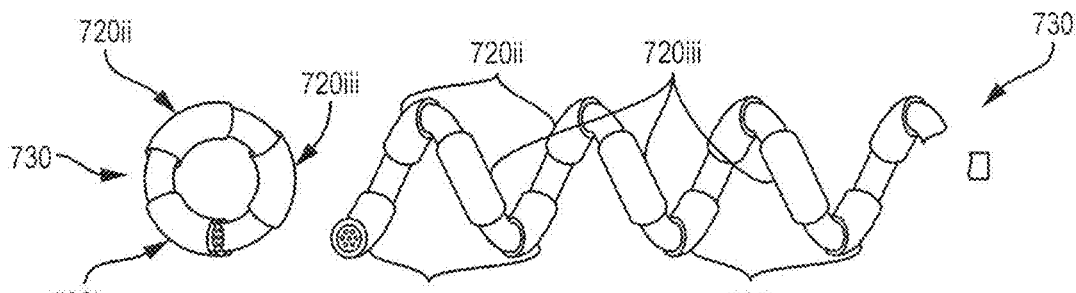
FIG. 24E1   FIG. 24E

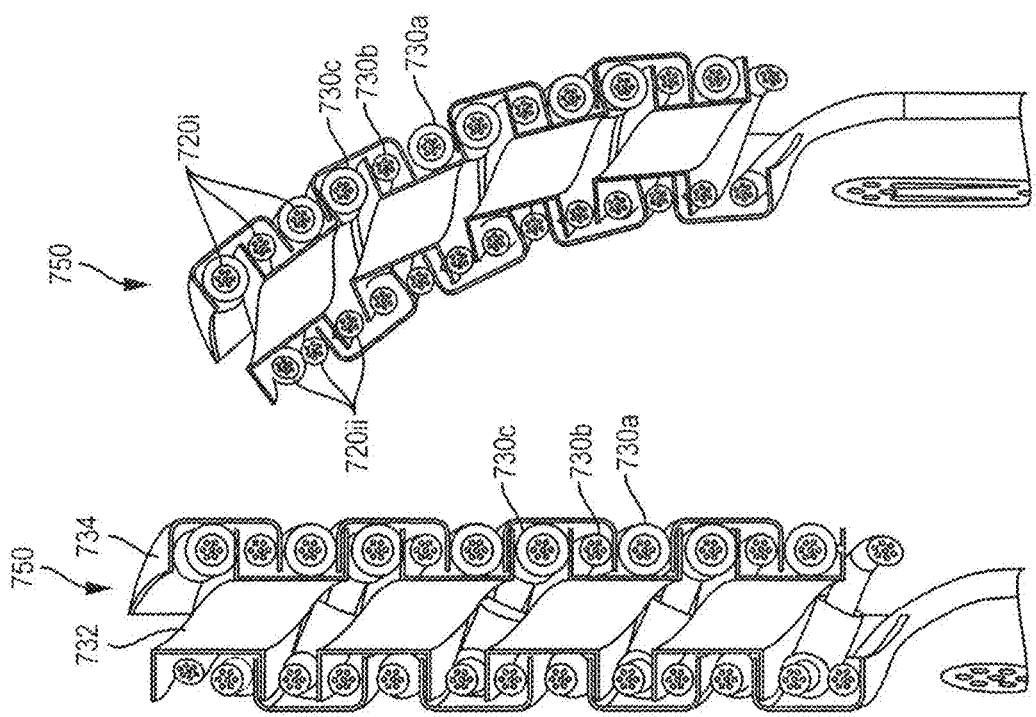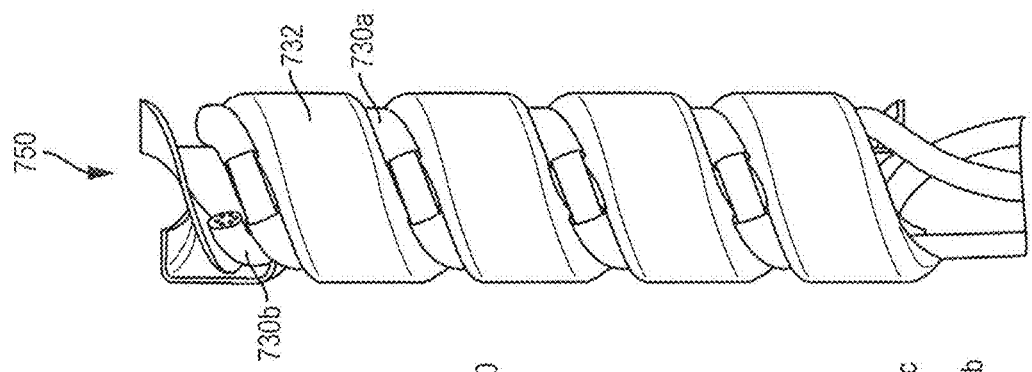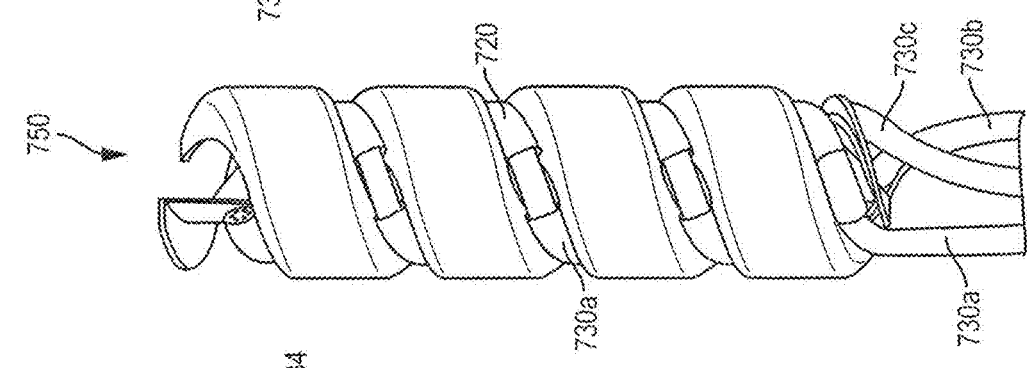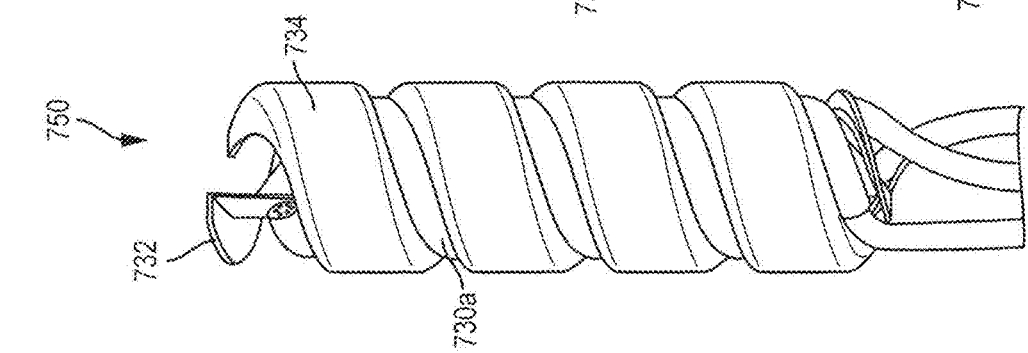

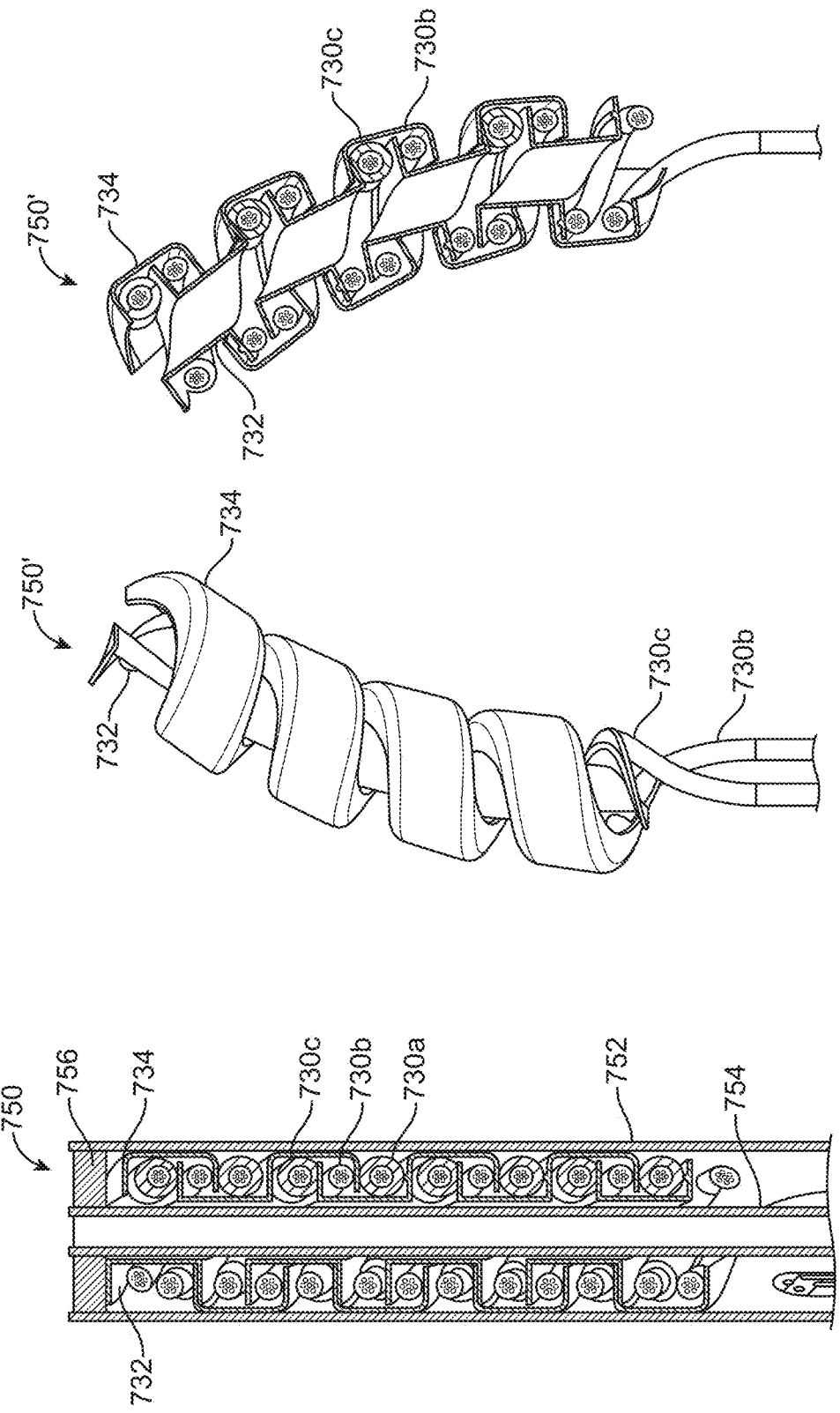

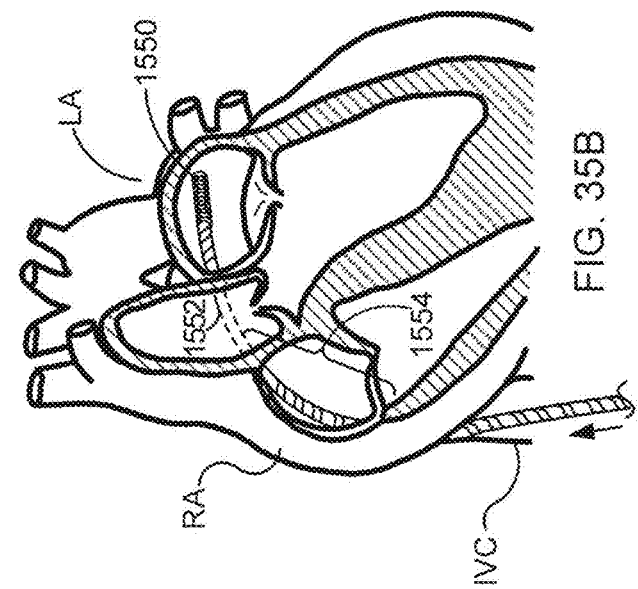
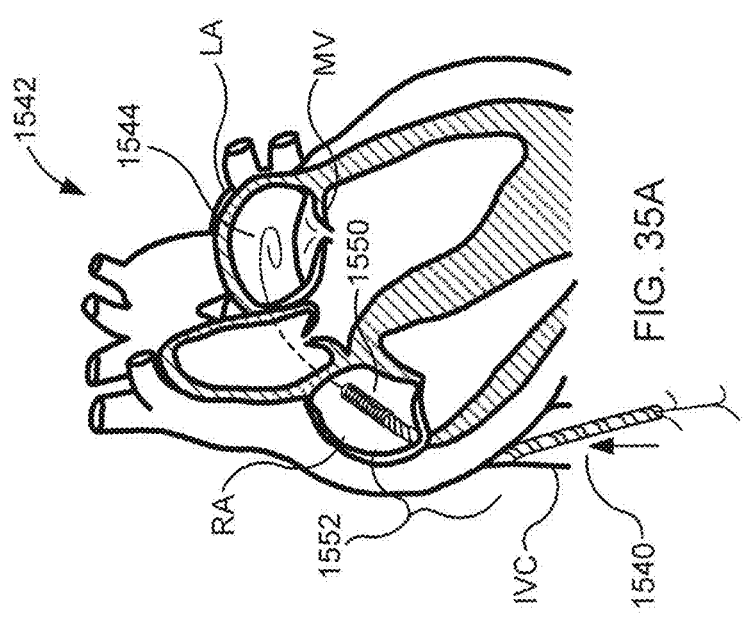

ARRHYTHMIA DIAGNOSTIC AND/OR THERAPY DELIVERY METHODS AND DEVICES, AND ROBOTIC SYSTEMS FOR OTHER USES

CROSS REFERENCE TO RELATED APPLICATIONS

This application claims the benefit of U.S. Provisional Application No. 62/401,001 filed on Sep. 28, 2016, which is incorporated by reference herein in its entirety.

The subject matter of the present application is related to that of co-assigned US Provisional Patent App. Nos. 62/263, 231 filed Dec. 4, 2015, entitled "Input and Articulation System for Catheters and Other Uses"; and 62/296,409 filed Feb. 17, 2016, entitled "Local Contraction of Flexible Bodies using Balloon Expansion for Extension-Contraction Catheter Articulation and Other Uses"; and U.S. patent application Ser. No. 15/081,026 filed Mar. 25, 2016, entitled "Articulation System, Devices, and Methods for Catheters and Other Uses"; the full disclosures which are incorporated herein by reference in their entirety.

FIELD OF THE INVENTION

In general, the present invention provides improved medical devices, systems, and methods. In exemplary embodiments, the invention provides balloon articulated catheter systems for diagnosing and/or treating arrhythmia in a heart of a patient. Alternative embodiments provide elongate flexible structures that can sense engagement force applied at a distal end by transmission of fluid pressure along a fluid channel toward a proximal end, with the channel optionally also being used to articulate a distal portion of the structure by inflation of a force-sensing/articulation balloon.

BACKGROUND OF THE INVENTION

Diagnosing and treating disease often involve accessing internal tissues of the human body. Once the tissues have been accessed, medical technology offers a wide range of diagnostic tools to evaluate tissues and identify lesions or disease states. Similarly, a number of therapeutic tools have been developed that can help surgeons interact with, remodel, deliver drugs to, or remove tissues associated with a disease state so as to improve the health and quality of life of the patient. Unfortunately, gaining access to and aligning tools with the appropriate internal tissues for evaluation or treatment can represent a significant challenge to the physician, can cause serious pain to the patient, and may (at least in the near term) be seriously detrimental to the patient's health.

Open surgery is often the most straightforward approach for gaining access to internal tissues. Open surgery can provide such access by incising and displacing overlying tissues so as to allow the surgeon to manually interact with the target internal tissue structures of the body. This standard approach often makes use of simple, hand-held tools such as scalpels, clamps, sutures, and the like. Open surgery remains, for many conditions, a preferred approach. Although open surgical techniques have been highly successful, they can impose significant trauma to collateral tissues, with much of that trauma being associated with gaining access to the tissues to be treated.

To help avoid the trauma associated with open surgery, a number of minimally invasive surgical access and treatment technologies have been developed. Many minimally invasive techniques involve accessing the vasculature, often through the skin of the thigh, neck, or arm. One or more elongate flexible catheter structures can then be advanced along the network of blood vessel lumens extending throughout the body and its organs. While generally limiting trauma to the patient, catheter-based endoluminal therapies are often reliant on a number of specialized catheter manipulation techniques to safely and accurately gain access to a target region, to position a particular catheter-based tool in alignment with a particular target tissue, and/or to activate or use the tool. In fact, some endoluminal techniques that are relatively simple in concept can be very challenging (or even impossible) in practice (depending on the anatomy of a particular patient and the skill of a particular physician). More specifically, advancing a flexible guidewire and/or catheter through a tortuously branched network of body lumens might be compared to pushing a rope. As the flexible elongate body advances around first one curve and then another, and through a series of branch intersections, the catheter/tissue forces, resilient energy storage (by the tissue and the elongate body), and movement interactions may become more complex and unpredictable, and control over the rotational and axial position of the distal end of a catheter can become more challenging and less precise. Hence, accurately aligning these elongate flexible devices with the desired luminal pathway and target tissues can be a significant challenge.

A variety of mechanisms can be employed to steer or variably alter deflection of a tip of a guidewire or catheter in one or more lateral directions to facilitate endoluminal and other minimally invasive techniques. Pull wires may be the most common catheter tip deflection structures and work well for many catheter systems by, for example, controllably decreasing separation between loops along one side of a helical coil, braid, or cut hypotube near the end of a catheter or wire. It is often desirable to provide positive deflection in opposed directions (generally by including opposed pull wires), and in many cases along two orthogonal lateral axes (so that three or four pull wires are included in some devices). Where additional steering capabilities are desired in a single device, still more pull wires may be included. Complex and specialized catheter systems having dozens of pull wires have been proposed and built, in some cases with each pull wire being articulated by a dedicated motor attached to the proximal end. Alternative articulation systems have also been proposed, including electrically actuated shape memory alloy structures, piezoelectric actuation, phase change actuation, and the like. As the capabilities of steerable systems increase, the range of therapies that can use these technologies should continue to expand.

Unfortunately, as articulation systems for catheters get more complex, it can be more and more challenging to maintain accurate control over these flexible bodies. For example, pull wires that pass through bent flexible catheters often slide around the bends over surfaces within the catheter, with the sliding interaction extending around not only bends intentionally commanded by the user, but also around bends that are imposed by the tissues surrounding the catheter. Hysteresis and friction of a pull-wire system may vary significantly with that sliding interaction and with different overall configurations of the bends, so that the articulation system response may be difficult to predict and control. Furthermore, more complex pull wire systems may add additional challenges. While opposed pull-wires can each be used to bend a catheter in opposite directions from a generally straight configuration, attempts to use both together—while tissues along the segment are applying unknown forces in unknown directions—may lead to widely inconsistent results. Hence, there could be benefits to providing more accurate small and precise motions, to improving the lag time, and/or to providing improved transmission of motion over known catheter pull-wire systems so as to avoid compromising the coordination, as experienced by the surgeon, between the input and output of catheters and other elongate flexible tools.

Along with catheter-based therapies, a number of additional minimally invasive surgical technologies have been developed to help treat internal tissues while avoiding at least some of the trauma associated with open surgery. Among the most impressive of these technologies is robotic surgery. Robotic surgeries often involve inserting one end of an elongate rigid shaft into a patient, and moving the other end with a computer-controlled robotic linkage so that the shaft pivots about a minimally invasive aperture. Surgical tools can be mounted on the distal ends of the shafts so that they move within the body, and the surgeon can remotely position and manipulate these tools by moving input devices with reference to an image captured by a camera from within the same workspace, thereby allowing precisely scaled micro-surgery. Alternative robotic systems have also been proposed for manipulation of the proximal end of flexible catheter bodies from outside the patient so as to position distal treatment tools. These attempts to provide automated catheter control have met with challenges, which may be in-part because of the difficulties in providing accurate control at the distal end of a flexible elongate body using pull-wires extending along bending body lumens. Still further alternative catheter control systems apply large magnetic fields using coils outside the patient's body to direct catheters inside the heart of the patient, and more recent proposals seek to combine magnetic and robotic catheter control techniques. In addition to the technical challenges of (and large capital equipment investments involved in) known robotic manipulators and catheter articulation systems, the user interface of these systems are often large, complex, expensive, and/or configured to be used by a physician seated outside the sterile field. While the potential improvements to control surgical accuracy make all of these efforts alluring, the capital total equipment costs and overall burden to the healthcare system of these large, specialized systems is a concern.

In light of the above, it would be beneficial to provide improved medical devices, systems, and methods, including improved input devices, articulation systems, and methods for users to direct and control articulation of flexible medical structures such as catheters, guidewires, and the like. Improved techniques for diagnosing and/or treating hard-to-access tissues would also be beneficial. It would be particularly beneficial if these new technologies were suitable to provide or enhance therapeutically effective control over movement of a distal end of a flexible guidewire, catheter, or other elongate body extending within a patient body via the vascular system so as to facilitate diagnosing and/or treating an arrhythmia from within a patient body, such as for alleviation of atrial fibrillation (AFib) from within the left atrium, identification of arrhythmogenic sites and/or undesirable contractile pathways, and the like. Elongate flexible bodies that could sense engagement forces between a distal end of the body and a tissue surface or the like would also be beneficial.

BRIEF SUMMARY OF THE INVENTION

The present invention generally provides new medical devices, systems, and methods, with exemplary embodiments providing improved systems for diagnosing and/or treating arrhythmia of a heart. The invention optionally makes use of an array of articulation balloons to control movement of a distal portion of a catheter inside the heart, and may be used to align a diagnostic or treatment tool with a target tissue surface region along or adjacent an inner surface of one of the chambers of the heart. As the articulation balloons can generate articulation forces at the site of articulation, the movement of the articulated catheter within the beating heart may be better controlled and/or provide greater dexterity than movements induced by transmitting articulation forces proximally along a catheter body that winds through a tortuous vascular pathway. In preferred embodiments, one or more fluid channels will transmit pressure signals that can be used to determine engagement forces between an electrode or other surface near the distal and of an elongate flexible structure and a tissue or other surface, and those same channels may also be used to control inflation of a balloon articulation array, with the pressure signals optionally providing both force and engagement orientation information.

In a first aspect, the invention provides an arrhythmia catheter system for diagnosing and/or treating an arrhythmia of a heart of a patient. The system comprises an elongate flexible cardiac catheter body having a proximal end and a distal end with an axis therebetween. An arrhythmia tool can be mounted near the distal end of the catheter body, the tool having an axis. The catheter body can have an articulated portion adjacent the distal end, and the articulated portion may have an array of articulation balloons.

Optionally, the balloons may include a first subset and a second subset, so that inflation of the first subset articulates the articulated portion along a first orientation, and inflation of the second subset articulates the articulated portion along a second orientation. The second orientation may be transverse to the first orientation, and the second subset may include some or all of the balloons in the first subset (such as where three groups of balloons are each separated by 120 degrees, and one group can be inflated to bend the catheter in an X direction, and that group and another group are both inflated in different amounts to bend the catheter in a Y direction). In some embodiments, the tool may comprise an ablation electrode. In other embodiments, the tool may comprise a diagnostic electrode array, such as a "barber pole" array optionally along a lasso electrode tip.

Advantageously, a pressure sensor can be coupled to the balloons and to an output. Preferably, a processor couples the output to the pressure sensor so that the output can provide an indication of an engagement force between the electrode and the heart in response to balloon pressure signals. The balloon pressure signals may include a first pressure signal associated with a third subset of the balloons and a second pressure signal associated with a fourth subset of the balloons, and the indication may identifies an orientation of the engagement force.

The catheter body may optionally be included in a transseptal access system. In some embodiments, the articulated portion can include a first articulated segment and a second articulated segment, wherein the first segment can articulate along first and second lateral orientations. The second segment may be configured to be articulated along third and fourth lateral orientations, with differing subsets of balloons often being used for articulation in these differing orientations. For example, first and second subsets of balloons may induce articulation in the first and second orientation, and a third subset of balloons may axially elongate the articulated portion. The ranges of motion for each of the first and second segments along the first, second, third, and forth orientations may be over about 120 degrees.

In another aspect, the invention provides a catheter system for diagnosing and/or treating a tissue of a patient. The tissue will often have a tissue surface, and the system may comprise an elongate flexible catheter body having a proximal end and a distal end with an axis therebetween. A diagnostic and/or treatment tool can be mounted near the distal end of the catheter body. A fluid channel may extending along the axis between the proximal end and the tool, and an engagement between the tool and the tissue surface may induces pressure within the channel. An output may be coupled to the channel, and may indicate a force of the engagement.

While some embodiments may provide a fluid-pressure-based engagement pressure without also using the cannel for articulation, in exemplary embodiments an array of articulation balloons is coupled to the proximal end by a plurality of channels. The engagement may induce a plurality of differing pressures in the balloons in response to an orientation of the engagement force. The output will often indicate the engagement orientation as well as the force.

In another aspect, the invention provides a method for diagnosing and/or treating an arrhythmia of a heart of a patient. The method comprises introducing an elongate flexible cardiac catheter body into the heart, the catheter body having a proximal end and a distal end and an arrhythmia tool mounted near the distal end of the catheter body. The catheter body can be articulated so as to align the tool with a target tissue region within the heart by inflating a subset of an array of articulation balloons disposed along the catheter body.

In another aspect, the invention provides an articulation system comprising an elongate flexible body having a proximal end and a distal end with an axis therebetween. A surface is near the distal end of the body, and an articulation balloon array is disposed proximal of the surface. A fluid channel extends along the axis between the proximal end and the balloon array. An engagement between the surface and a target structure induces pressure within the channel. A pressure sensor is coupled with the channel, and a processor is coupled with the pressure sensor so as to determine a force of the engagement.

Optionally, the processor can be configured to determine a mass of inflation fluid present in the channel and/or a subset of balloons in the articulation array, such as by measuring pressures in a number of balloon channels, by knowing a supply pressure and exhaust pressure, and by estimating mass flows into and out of the channel based on valve cycle times of inflation and deflation valves. Inflation fluid mass in the channels may be calculated for compressible fluids such as a gas (for which the mass variation may be much larger than that of the balloons) and may or may not vary significantly with channel compliance for a liquid. The processor can tally and use the mass of inflation fluid, optionally along with a stiffness of the body (if it is significant), to determine the force of engagement.

BRIEF DESCRIPTION OF THE DRAWINGS

FIG. 1-1 schematically illustrates a catheter articulation system having a hand-held proximal housing and a catheter with a distal articulatable portion in a relaxed state.

FIGS. 16 and 17 are a schematic illustration of an exemplary axial expansion/contraction skeleton with axial expansion and axial contraction balloons; and a corresponding cross-section of a skeleton having an axial series of annular members or rings articulated by the axial expansion and axial contraction balloons, respectively.

FIGS. 18-20 are illustrations of elongate flexible articulated structures having annular skeletons with three opposed sets of balloons, and show how varying inflation of the balloons can be used to axially contract some portions of the frame and axially extend other portions to bend or elongate the frame and to control a pose or shape of the frame in three dimensions.

FIGS. 24A-24G illustrate components of another alternative elongate articulated flexible structure having axial expansion balloons and opposed axial contraction balloons, the structures here having helical skeleton members and helical balloon assemblies.

FIGS. 25A-25F illustrate exemplary elongate articulated flexible structures having helical skeleton members and three helical balloon assemblies supported in opposition along the skeleton, and also show how selective inflation of subsets of the balloons can locally axially elongate and/or contract the skeleton to bend the structure laterally and/or alter the overall length of the structure.

FIGS. 26A and 26B illustrate alternative articulated structures similar to those of FIG. 25, here with two balloon assemblies supported in opposition along the frames.

FIGS. 35A-35C schematically illustrate positioning and anchoring of a mitral valve delivery catheter system for deployment of a mitral valve prosthesis in heart of a patient FIGS. 36A-36C schematically illustrate positioning of a mitral valve prosthesis in five degrees of freedom by independent articulation of three axial segments of an articulated catheter.

DETAILED DESCRIPTION OF THE INVENTION

Figure 1:
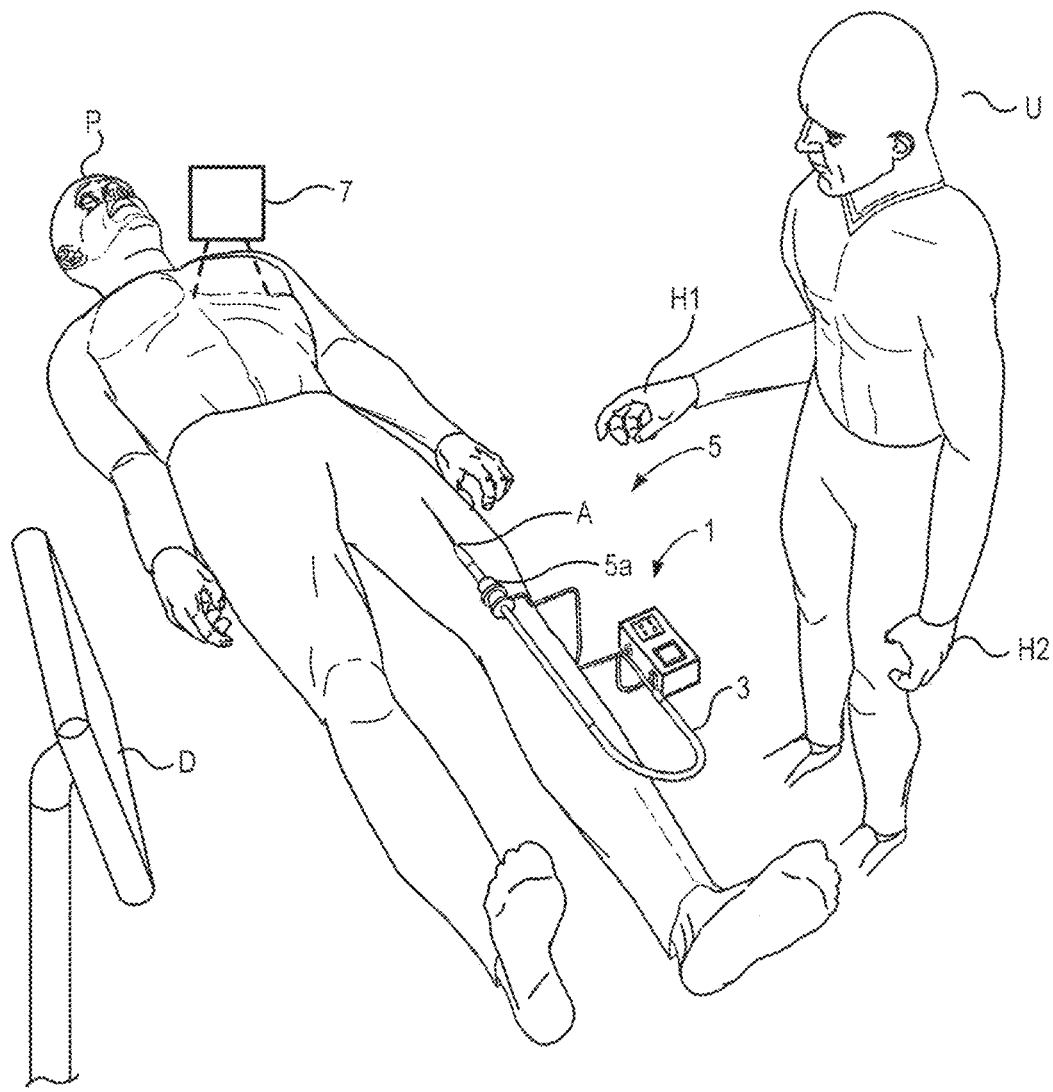
FIG. 1 is a simplified perspective view of a medical procedure in which a physician can input commands into a catheter system so that a catheter is articulated using systems and devices described herein.
Figure 1:
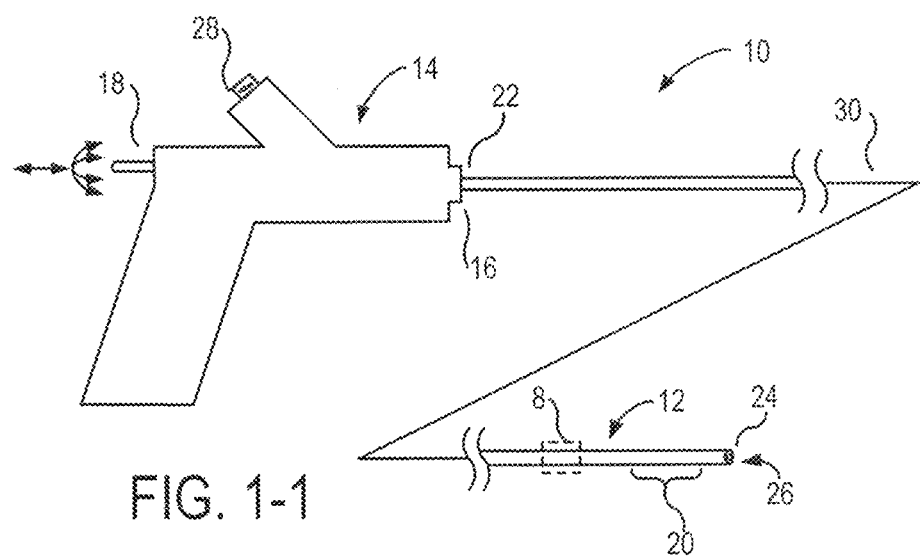

The present invention generally provides improved medical devices, systems, and methods, with exemplary embodiments providing improved systems for diagnosing and/or treating arrhythmias of a heart. The invention optionally makes use of an array of articulation balloons to control movement of a distal portion of a catheter inside the heart, and may be used to align a diagnostic or treatment tool with a mitral or other valve. As the articulation balloons can generate articulation forces at the site of articulation, the movement of the articulated catheter within the beating heart may be better controlled and/or provide greater dexterity than movements induced by transmitting articulation forces proximally along a catheter body that winds through a tortuous vascular pathway.

Embodiments provided herein may use balloon-like structures to effect articulation of the elongate catheter or other body. The term "articulation balloon" may be used to refer to a component which expands on inflation with a fluid and is arranged so that on expansion the primary effect is to cause articulation of the elongate body. Note that this use of such a structure is contrasted with a conventional interventional balloon whose primary effect on expansion is to cause substantial radially outward expansion from the outer profile of the overall device, for example to dilate or occlude or anchor in a vessel in which the device is located. Independently, articulated medial structures described herein will often have an articulated distal portion, and an unarticulated proximal portion, which may significantly simplify initial advancement of the structure into a patient using standard catheterization techniques.

The catheter bodies (and many of the other elongate flexible bodies that benefit from the inventions described herein) will often be described herein as having or defining an axis, such that the axis extends along the elongate length of the body. As the bodies are flexible, the local orientation of this axis may vary along the length of the body, and while the axis will often be a central axis defined at or near a center of a cross-section of the body, eccentric axes near an outer surface of the body might also be used. It should be understood, for example, that an elongate structure that extends "along an axis" may have its longest dimension extending in an orientation that has a significant axial component, but the length of that structure need not be precisely parallel to the axis. Similarly, an elongate structure that extends "primarily along the axis" and the like will generally have a length that extends along an orientation that has a greater axial component than components in other orientations orthogonal to the axis. Other orientations may be defined relative to the axis of the body, including orientations that are transverse to the axis (which will encompass orientation that generally extend across the axis, but need not be orthogonal to the axis), orientations that are lateral to the axis (which will encompass orientations that have a significant radial component relative to the axis), orientations that are circumferential relative to the axis (which will encompass orientations that extend around the axis), and the like. The orientations of surfaces may be described herein by reference to the normal of the surface extending away from the structure underlying the surface. As an example, in a simple, solid cylindrical body that has an axis that extends from a proximal end of the body to the distal end of the body, the distal-most end of the body may be described as being distally oriented, the proximal end may be described as being proximally oriented, and the surface between the proximal and distal ends may be described as being radially oriented. As another example, an elongate helical structure extending axially around the above cylindrical body, with the helical structure comprising a wire with a square cross section wrapped around the cylinder at a 20 degree angle, might be described herein as having two opposed axial surfaces (with one being primarily proximally oriented, one being primarily distally oriented). The outermost surface of that wire might be described as being oriented exactly radially outwardly, while the opposed inner surface of the wire might be described as being oriented radially inwardly, and so forth.

Referring first to FIG. 1, a first exemplary catheter system 1 and method for its use are shown. A physician or other system user U interacts with catheter system 1 so as to perform a therapeutic and/or diagnostic procedure on a patient P, with at least a portion of the procedure being performed by advancing a catheter 3 into a body lumen and aligning an end portion of the catheter with a target tissue of the patient. More specifically, a distal end of catheter 3 is inserted into the patient through an access site A, and is advanced through one of the lumen systems of the body (typically the vasculature network) while user U guides the catheter with reference to images of the catheter and the tissues of the body obtained by a remote imaging system.

In this exemplary embodiment, catheter system 1 may be used in a manual mode during a portion of the procedure. In the manual mode, user U can help advance, retract, or position the distal end of the catheter within the patient by manually grasping the exposed catheter shaft near the patient and moving the catheter shaft relative to the patient, often while also holding an introducer sheath of the assembly to prevent the introducer sheath from being dislodged. Alternatively, user U may grasp a proximal or housing affixed to the proximal end of the catheter body with one hand (for example, using a forefinger and/or a thumb to intermittently adjust a steering bend angle or the like, with the rest of the hand supporting the housing), and may manipulate the catheter relative to the introducer with the other hand (for example, with the thumb and forefinger grasping and manipulating the catheter body and the remaining fingers holding the introducer in place). The input for powered movement of catheter system 1 may to some extent mimic these manual manipulations so as to facilitate driving the catheter in an automated articulation mode, and also to facilitate the transitions between manual and automated articulation modes. For example, user U may grasp a first exposed portion of assembly 5*a* using fingers of a first hand H1 (to inhibit introducer sheath displacement), and may also grasp and manipulate another exposed portion of assembly 5*a* near the patient using fingers of a second hand H2. Alternatively, the user may grasp the introducer and adjacent catheter with one hand, and may move a proximal housing or handle of the catheter with the other. In either case, relative movements of these grasped components can be used as input movement commands to the automated catheter system, with those relative movements being reminiscent of the hand movements used in the manual mode (and of the hand movements used for manipulation of known manual catheter systems). While often described herein with reference to manipulation of a catheter, these devices, system, and methods will also be well suited for manipulation of other medical structures including guidewires and the like, and may also be used for manipulation of non-medical structures such as industrial endoscopes or boroscopes and the like.

Exemplary catheter system 1 will often be introduced into patient P through one of the major blood vessels of the leg, arm, neck, or the like. A variety of known vascular access techniques may also be used, or the system may alternatively be inserted through a body orifice or otherwise enter into any of a number of alternative body lumens. The imaging system will generally include an image capture system 7 for acquiring the remote image data and a display D for presenting images of the internal tissues and adjacent catheter system components. Suitable imaging modalities may include fluoroscopy, computed tomography, magnetic resonance imaging, ultrasonography, combinations of two or more of these, or others.

Referring next to FIG. 1-1 components which may be included in or used with catheter system 1 or catheter 3 (described above) can be more fully understood with reference to an alternative catheter system 10 and its catheter 12. Catheter 12 generally includes an elongate flexible catheter body and is detachably coupled to a handle 14, preferably by a quick-disconnect coupler 16. Handle 14 (and similar proximal handles having steering input capabilities) may be used in place of or together with assembly 5*a* (also described above), so that components of such handles can be included in the user interface of the catheter system. Catheter body 12 has an axis 30, and an input 18 of handle 14 can be moved by a user so as to locally alter the axial bending characteristics along catheter body 12, often for variably articulating an actuated portion 20 of the catheter body. Catheter body 12 will often have a working lumen 26 into or through which a therapeutic and/or diagnostic tool may be advanced from a proximal port 28 of handle 14. Alternative embodiments may lack a working lumen, may have one or more therapeutic or diagnostic tools incorporated into the catheter body near or along actuated portion 20, may have a sufficiently small outer profile to facilitate use of the body as a guidewire, may carry a tool or implant near actuated portion 20 or near distal end 26, or the like. In particular embodiments, catheter body 12 may support a therapeutic or diagnostic tool 8 proximal of, along the length of, and/or distal of actuated portion 20. Alternatively, a separate elongate flexible catheter body may be guided distally to a target site once catheter body 20 has been advanced (with the elongate body for such uses often taking the form and use of a guidewire or guide catheter).

The particular tool or tools included in, advanceable over, and/or introducible through the working lumen of catheter body 20 may include any of a wide range of therapeutic and/or treatment structures. Examples include cardiovascular therapy and diagnosis tools (such as angioplasty balloons, stent deployment balloons or other devices, atherectomy devices, tools for detecting, measuring, and/or characterizing plaque or other occlusions, tools for imaging or other evaluation of, and/or treatment of, the coronary or peripheral arteries, structural heart tools (including prostheses or other tools for valve procedures, for altering the morphology of the heart tissues, chambers, and appendages, and the like), tools for electrophysiology mapping or ablation tools, and the like); stimulation electrodes or electrode implantation tools (such as leads, lead implant devices, and lead deployment systems, leadless pacemakers and associated deployments systems, and the like); neurovascular therapy tools (including for accessing, diagnosis and/or treatment of hemorrhagic or ischemic strokes and other conditions, and the like); gastrointestinal and/or reproductive procedure tools (such as colonoscopic diagnoses and intervention tools, transurethral procedure tools, transesophageal procedure tools, endoscopic bariatric procedure tools, etc.); hysteroscopic and/or falloposcopic procedure tools, and the like; pulmonary procedure tools for therapies involving the airways and/or vasculature of the lungs; tools for diagnosis and/or treatment of the sinus, throat, mouth, or other cavities, and a wide variety of other endoluminal therapies and diagnoses structures. Such tools may make use of known surface or tissue volume imaging technologies (including imaging technologies such as 2-D or 3-D cameras or other imaging technologies; optical coherence tomography technologies; ultrasound technologies such as intravascular ultrasound, transesophogeal ultrasound, intracardiac ultrasound, Doppler ultrasound, or the like; magnetic resonance imaging technologies; and the like), tissue or other material removal, incising, and/or penetrating technologies (such a rotational or axial atherectomy technologies; morcellation technologies; biopsy technologies; deployable needle or microneedle technologies; thrombus capture technologies; snares; and the like), tissue dilation technologies (such as compliant or non-compliant balloons, plastically or resiliently expandable stents, reversibly expandable coils, braids or other scaffolds, and the like), tissue remodeling and/or energy delivery technologies (such as electrosurgical ablation technologies, RF electrodes, microwave antennae, cautery surfaces, cryosurgical technologies, laser energy transmitting surfaces, and the like), local agent delivery technologies (such as drug eluting stents, balloons, implants, or other bodies; contrast agent or drug injection ports; endoluminal repaving structures; and the like), implant and prosthesis deploying technologies, anastomosis technologies and technologies for applying clips or sutures, tissue grasping and manipulation technologies; and/or the like. In some embodiments, the outer surface of the articulation structure may be used to manipulate tissues directly. Non-medical embodiments may similarly have a wide range of tools or surfaces for industrial, assembly, imaging, manipulation, and other uses.

Addressing catheter body 12 of system 10 (and particularly articulation capabilities of actuated portion 20) in more detail, the catheter body generally has a proximal end 22 and a distal end 24 with axis 30 extending between the two. As can be understood with reference to FIG. 2, catheter body 12 may have a short actuated portion 20 of about 3 diameters or less, but will often have an elongate actuated portion 20 extending intermittently or continuously over several diameters of the catheter body (generally over more than 3 diameters, often over more than 10 diameters, in many cases over more than 20 diameters, and in some embodiments over more than 40 diameters). A total length of catheter body 12 (or other flexible articulated bodies employing the actuation components described herein) may be from 5 to 500 cm, more typically being from 15 to 260 cm, with the actuated portion optionally having a length of from 1 to 150 cm (more typically being 2 to 20 cm) and an outer diameter of from 0.65 mm to 5 cm (more typically being from 1 mm to 2 cm). Outer diameters of guidewire embodiments of the flexible bodies may be as small as 0.012" though many embodiments may be more than 2 Fr, with catheter and other medical embodiments optionally having outer diameters as large as 34 French or more, and with industrial robotic embodiments optionally having diameters of up to 1" or more. Exemplary catheter embodiments for structural heart therapies (such as trans-catheter aortic or mitral valve repair or implantation, left atrial appendage closure, and the like) may have actuated portions with lengths of from 3 to 30 cm, more typically being from 5 to 25 cm, and may have outer profiles of from 10 to 30 Fr, typically being from 12 to 18 Fr, and ideally being from 13 to 16 Fr. Electrophysiology therapy catheters (including those having electrodes for sensing heart cycles and/or electrodes for ablating selected tissues of the heart) may have sizes of from about 5 to about 12 Fr, and articulated lengths of from about 3 to about 30 cm. A range of other sizes might also be implemented for these or other applications.

Figure 1A:
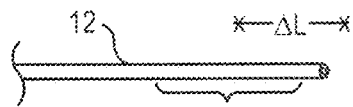
FIGS. 1A-1C schematically illustrate a plurality of alternative articulation states of the distal portion of the catheter in the system of FIG. 1.
Figure 1B:
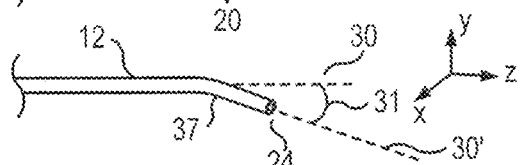
Figure 1C:
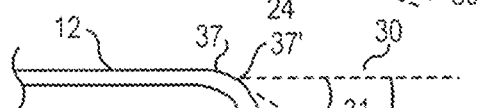

Referring now to FIGS. 1A, 1B, and 1C, system 10 may be configured to articulate actuated portion 20. Articulation will often allow movement continuously throughout a range of motion, though some embodiments may provide articulation in-part or in-full by selecting from among a plurality of discrete articulation states. Catheters having opposed axial extension and contraction actuators are described herein that may be particularly beneficial for providing continuous controlled and reversible movement, and can also be used to modulate the stiffness of a flexible structure. These continuous and discrete systems share many components (and some systems might employ a combination of both approaches). First addressing the use of a discrete state system, FIG. 1A, system 10 can, for example, increase an axial length of actuated portion 20 by one or more incremental changes in length $\Delta L$. An exemplary structure for implementation of a total selectable increase in length $\Delta L$ can combine a plurality of incremental increases in length $\Delta L = \Delta L_1 + \Delta L_2 + \ldots$ ), as can be understood with reference to FIG. 6. As shown in FIGS. 1B and 1C, system 10 may also deflect distal end 24 to a first bent state having a first bend angle 31 between unarticulated axis 30 and an articulated axis 30' (as shown schematically in FIG. 1B), or to a second bent state having a total bend angle 33 (between articulated axis 30 and articulated axis 30"), with this second bend angle being greater than the first bend angle (as shown schematically in FIG. 1C). An exemplary structure for combining multiple discrete bend angle increments to form a total bend angle 33 can be understood with reference to FIG. 5. Regardless, the additional total cumulative bend angle 33 may optionally be implemented by imposing the first bend 31 (of FIG. 1B) as a first increment along with one or more additional bend angle increments 35. The incremental changes to actuated portion 20 may be provided by fully inflating and/or deflating actuation balloons of the catheter system. Bend capabilities may be limited to a single lateral orientation, but will more typically be available in different lateral orientations, most typically in any of 3 or 4 orientations (for example, using balloons positioned along two pairs of opposed lateral axes, sometimes referred to as the +X, −X, +Y and −Y orientations), and by combining different bend orientations, in intermediate orientations as well. Continuous positioning may be implemented using similar articulation structures by partially inflating or deflating balloons or groups of balloons.

System 10 may also be configured to provide catheter 12 with any of a plurality of discrete alternative total axial lengths. As with the bend capabilities, such length actuation may also be implemented by inflating balloons of a balloon array structure. To provide articulation with the simple balloon array structures described herein, each actuation may be implemented as a combination of discrete, predetermined actuation increments (optionally together with one or more partial or modulated actuation) but may more often be provided using modulated or partial inflation of balloons.

Figure 2:
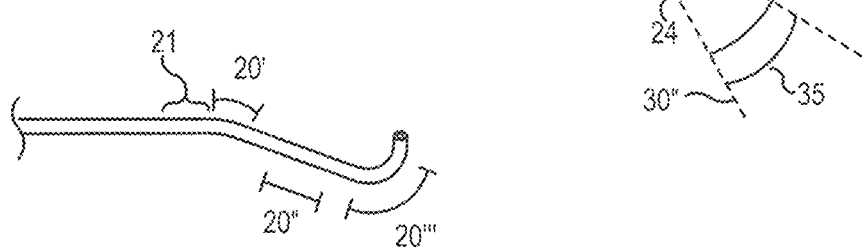
FIG. 2 schematically illustrates an alternative distal structure having a plurality of articulatable sub-regions or segments so as to provide a desired total number of degrees of freedom and range of movement.

Referring now to FIGS. 1-1 and 2, embodiments of articulation system 10 will move the distal end 24 of catheter 12 toward a desired position and/or orientation in a workspace relative to a base portion 21, with the base portion often being adjacent to and proximal of actuated portion 20. Note that such articulation may be relatively (or even completely) independent of any bending of catheter body 12 proximal of base portion 21. The location and orientation of proximal base 21 (relative to handle 14 or to another convenient fixed or movable reference frame) may be identified, for example, by including known catheter position and/or orientation identification systems in system 10, by including radiopaque or other high-contrast markers and associated imaging and position and/or orientation identifying image processing software in system 10, by including a flexible body state sensor system along the proximal portion of catheter body 12, by foregoing any flexible length of catheter body 12 between proximal handle 14 and actuated portion 20, or the like. A variety of different degrees of freedom may be provided by actuated portion 20. Exemplary embodiments of articulation system 10 may allow, for example, distal end 24 to be moved with 2 degrees of freedom, 3 degrees of freedom, 4 degrees of freedom, 5 degrees of freedom, or 6 degrees of freedom relative to base portion 21. The number of kinematic degrees of freedom of articulated portion 20 may be much higher in some embodiments, particularly when a number of different alternative subsets of the balloon array could potentially be in different inflation states to give the same resulting catheter tip and/or tool position and orientation.

Note that the elongate catheter body 12 along and beyond actuated portion 20 may (and often should) remain flexible before, during, and after articulation, so as to avoid inadvertently applying lateral and/or axial forces to surrounding tissues that are beyond a safe threshold. Nonetheless, embodiments of the systems described herein may locally and controllable increase a stiffness of one or more axial portions of catheter body 12, along actuated portion 20, proximal of actuated portion 20, and/or distal of actuated portion 20. Such selective stiffening of the catheter body may be implemented with or without active articulation capabilities, may extend along one or more axial portion of catheter body 12, and may alter which portions are stiffened and which are more flexible in response to commands from the user, sensor input (optionally indicating axial movement of the catheter), or the like.

As shown in FIG. 2, actuated portion 20 may comprise an axial series of 2 or more (and preferably at least 3) actuatable sub-portions or segments 20', 20", 20''', with the segments optionally being adjacent to each other, or alternatively separated by relatively short (less than 10 diameters) and/or relatively stiff intermediate portions of catheter 12. Each sub-portion or segment may have an associated actuation array, with the arrays working together to provide the desired overall catheter shape and degrees of freedom to the tip or tool. At least 2 of the sub-portions may employ similar articulation components (such as similar balloon arrays, similar structural backbone portions, similar valve systems, and/or similar software). Commonality may include the use of corresponding actuation balloon arrays, but optionally with the characteristics of the individual actuation balloons of the different arrays and the spacing between the locations of the arrays varying for any distal tapering of the catheter body. There may be advantages to the use of differentiated articulation components, for example, with proximal and distal sub portions, 20', 20''' having similar structures that are configured to allow selective lateral bending with at least two degrees of freedom, and intermediate portion 20" being configured to allow variable axial elongation. In many embodiments, however, at least two (and preferably all) segments are substantially continuous and share common components and geometries, with the different segments having separate fluid channels and being separately articulatable but each optionally providing similar movement capabilities.

For those elongate flexible articulated structures described herein that include a plurality of axial segments, the systems will often determine and implement each commanded articulation of a particular segment as a single consistent articulation toward a desired segment shape state that is distributed along that segment. In some exemplary embodiments, the nominal or resting segment shape state may be constrained to a 3 DOF space (such as by continuous combinations of two transverse lateral bending orientations and an axial (elongation) orientation in an X-Y-Z work space). In some of the exemplary embodiments described herein (including at least some of the helical extension/contraction embodiments), lateral bends along a segment may be at least approximately planar when the segment is in or near a design axial length configuration (such as at or near the middle of the axial or Z range of motion), but may exhibit a slight but increasing off-plane twisting curvature as the segment moves away from that design configuration (such as near the proximal and/or distal ends of the axial range of motion). The off-plane bending may be repeatably accounted for kinematically by determining the changes in lateral orientation of eccentric balloons resulting from winding and unwinding of helical structures supporting those balloons when the helical structures increase and decrease in axial length. For example, a segment may be commanded (as part of an overall desired pose or movement) to bend in a −Y orientation with a 20 degree bend angle. If the bend is to occur at a design axial length (such as at the middle of the axial range of motion), and assuming balloons (or opposed balloon pairs) at 4 axial bend locations can be used to provide the commanded bend, the balloons (or balloon pairs) may each be inflated or deflated to bend the segment by about 5 degrees (thereby providing a total bend of 5*4 or 20 degrees) in the −Y orientation. If the same bend is to be combined with axial lengthening of the segment to the end of its axial range of motion, the processor may determine that the segment may would exhibit some twist (say 2 degrees) so that there would be a slight +X component to the commanded bend, so that the processor may compensate for the twist by commanding a corresponding −X bend component, or by otherwise compensating in the command for another segment of the flexible body.

Figure 3:
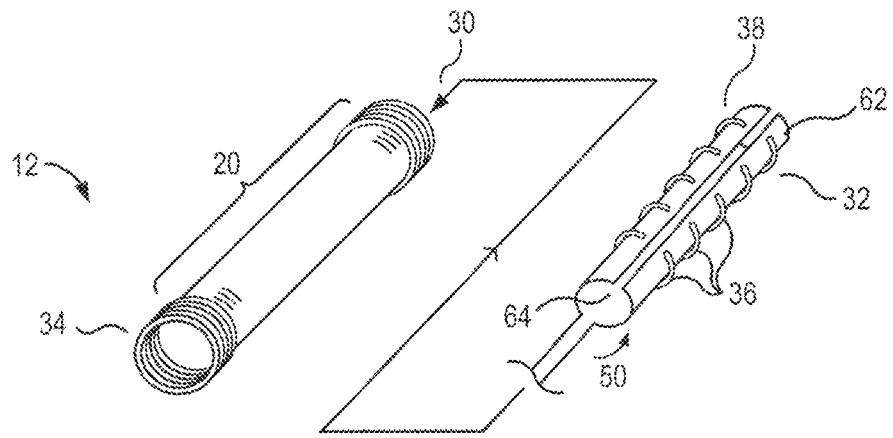
FIG. 3 is a simplified exploded perspective view showing a balloon array that can be formed in a substantially planar configuration and rolled into a cylindrical configuration, and which can be mounted coaxially to a helical coil or other skeleton framework for use in the catheter of the system of FIGS. 1 and 2.
Figure 5:
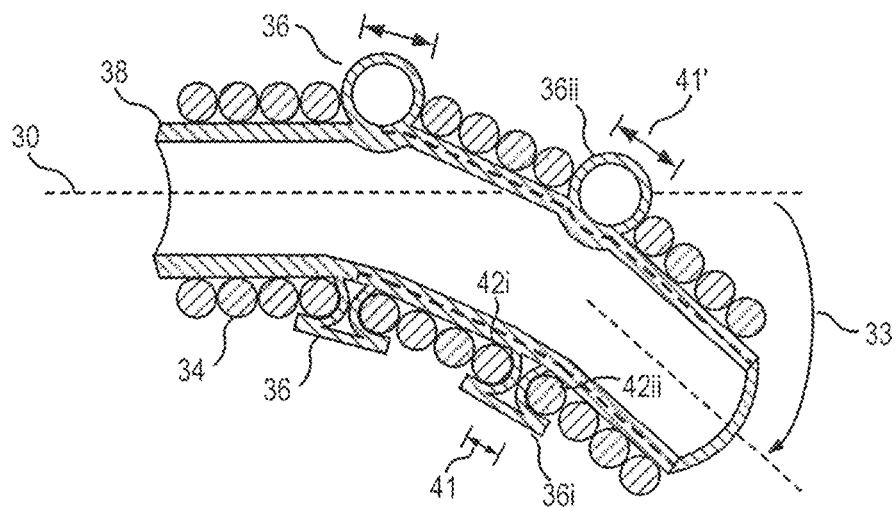
FIG. 5 is a simplified transverse cross-section of the articulatable catheter of FIGS. 4A and 4B, with a plurality of axially aligned balloons along one side of the articulatable region of the catheter inflated so that the catheter is in a laterally deflected state.

Referring to FIGS. 3 and 5, catheter body 12 of system 10 includes an actuation array structure 32 mounted to a structural skeleton (here in the form of a helical coil 34). Exemplary balloon array 32 includes fluid expandable structures or balloons 36 distributed at balloon locations along a flexible substrate 38 so as to define an M×N array, in which M is an integer number of balloons distributed about a circumference 50 of catheter 12 at a given location along axis 30, and N represents an integer number of axial locations along catheter 12 having actuation balloons. Circumferential and axial spacing of the array element locations will generally be known, and will preferably be regular. This first exemplary actuation array includes a 4×4 array for a total of 16 balloons; alternative arrays may be from 1×2 arrays for a total of 2 balloons to 8×200 arrays for a total of 1600 balloons (or beyond), more typically having from 3×3 to 6×20 arrays. While balloon arrays of 1×N may be provided (particularly on systems that rely on rotation of the catheter body to orient a bend), M will more typically be 2 or more, more often being from 3 to 8, and preferably being 3 or 4. Similarly, while balloon arrays of M×1 may be provided to allow imposition of a single bend increment at a particular location in any of a number of different desired lateral orientations, array 32 will more typically have an N of from 2 to 200, often being from 3 to 20 or 3 to 100. In contraction/expansion embodiments described below, multiple arrays may be provided with similar M×N arrays mounted in opposition. Not all array locations need have inflatable balloons, and the balloons may be arranged in more complex arrangements, such as with alternating circumferential numbers of balloons along the axis, or with varying or alternating separation between balloons along the axial length of the array.

The balloons of a particular segment or that are mounted to a common substrate may be described as forming an array, with the actuation balloon array structure optionally being used as a sub-array in a multi-segment or opposed articulation system. The combined sub-arrays together may form an array of the overall device, which may also be described simply as an array or optionally an overall or combined array. Exemplary balloon arrays along a segment or sub-portion of articulated portion 20 include 1×8, 1×12, and 1×16 arrays for bending in a single direction (optionally with 2, 3, 4, or even all of the balloons of the segment in fluid communication with a single common inflation lumen so as to be inflated together) and 4×4, 4×8, and 4×12 arrays for X-Y bending (with axially aligned groups of 2-12 balloons coupled with 4 or more common lumens for articulation in the +X, −X, +Y, and −Y orientations). Exemplary arrays for each segment having the opposed extension/retraction continuous articulation structures described herein may be in the form of a 3×2N, 3×3N, 4×2N, or 4×3N balloons arrays, for example, 3×2, 3×4, 3×6, 3×8, 3×10, 3×12, 3×14, and 3×16 arrays with 6 to 48 balloons, with the 3 lateral balloon orientations separated by 120 degrees about the catheter axis. Extension balloons will often be axially interspersed with contraction balloons along each lateral orientation, with separate 3×N arrays being combined together in a 3×2N extension/contraction array for the segment, while two extension balloons may be positioned axially between each contraction balloon for 3×3N arrangements. The contraction balloons may align axially and/or be in plane with the extension balloons they oppose, though it may be advantageous in some embodiments to arrange opposed balloons offset from a planer arrangement, so that (for example) two balloons of one type balance one balloon of the other, or vice versa. The extension balloons along each orientation of the segment may share a common inflation fluid supply lumen while the contraction balloons of the segment for each orientation similarly share a common lumen (using 6 fluid supply lumens per segment for both 3×2N and 3×3N arrays). An extension/contraction catheter may have from 1 to 8 such segments along the articulated portion, more typically from 1 to 5 segments, and preferably being 2 to 4 segments. Other medical and non-medical elongate flexible articulated structures may have similar or more complex balloon articulation arrays.

As can be seen in FIGS. 3, 4A, 4B, and 5, the skeleton will often (though not always) include an axial series of loops 42. When the loops are included in a helical coil 34, the coil may optionally be biased so as to urge adjacent loops 42 of the coil 34 toward each other. Such axially compressive biasing may help urge fluid out and deflate the balloons, and may by applied by other structures (inner and/or outer sheath(s), pull wires, etc.) with or without helical compression. Axial engagement between adjacent loops (directly, or with balloon walls or other material of the array between loops) can also allow compressive axial forces to be transmitted relatively rigidly when the balloons are not inflated. When a particular balloon is fully inflated, axial compression may be transmitted between adjacent loops by the fully inflated balloon wall material and by the fluid within the balloons. Where the balloon walls are non-compliant, the inflated balloons may transfer these forces relatively rigidly, though with some flexing of the balloon wall material adjacent the balloon/skeleton interface. Rigid or semi-rigid interface structures which distribute axial loads across a broader balloon interface region may limit such flexing. Axial tension forces (including those associated with axial bending) may be resisted by the biasing of the skeleton (and/or by other axial compressive structures). Alternative looped skeleton structures may be formed, for example, by cutting hypotube with an axial series of lateral incisions across a portion of the cross-section from one or more lateral orientations, braided metal or polymer elements, or the like. Non-looped skeletons may be formed using a number of alternative known rigid or flexible robotic linkage architectures, including with structures based on known soft robot structures. Suitable materials for coil 34 or other skeleton structures may comprise metals such as stainless steel, spring steel, superelastic or shape-memory alloys such as Nitinol™ alloys, polymers, fiber-reinforced polymers, high-density or ultrahigh-density polymers, or the like.

Figure 6:
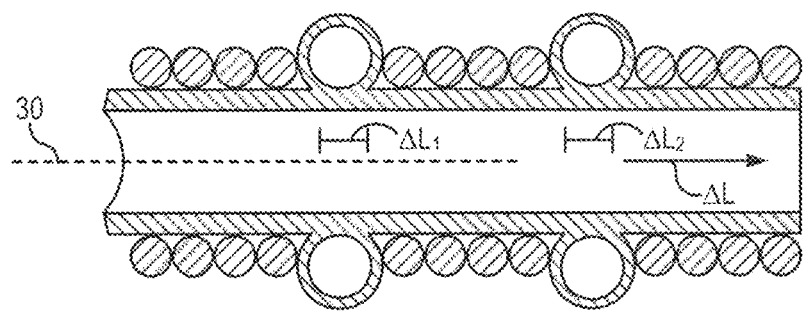
FIG. 6 is a simplified transverse cross-section of the articulatable catheter of FIG. 4, with a plurality of laterally opposed balloons inflated so that the catheter is in an axially elongated state.
Figure 7:
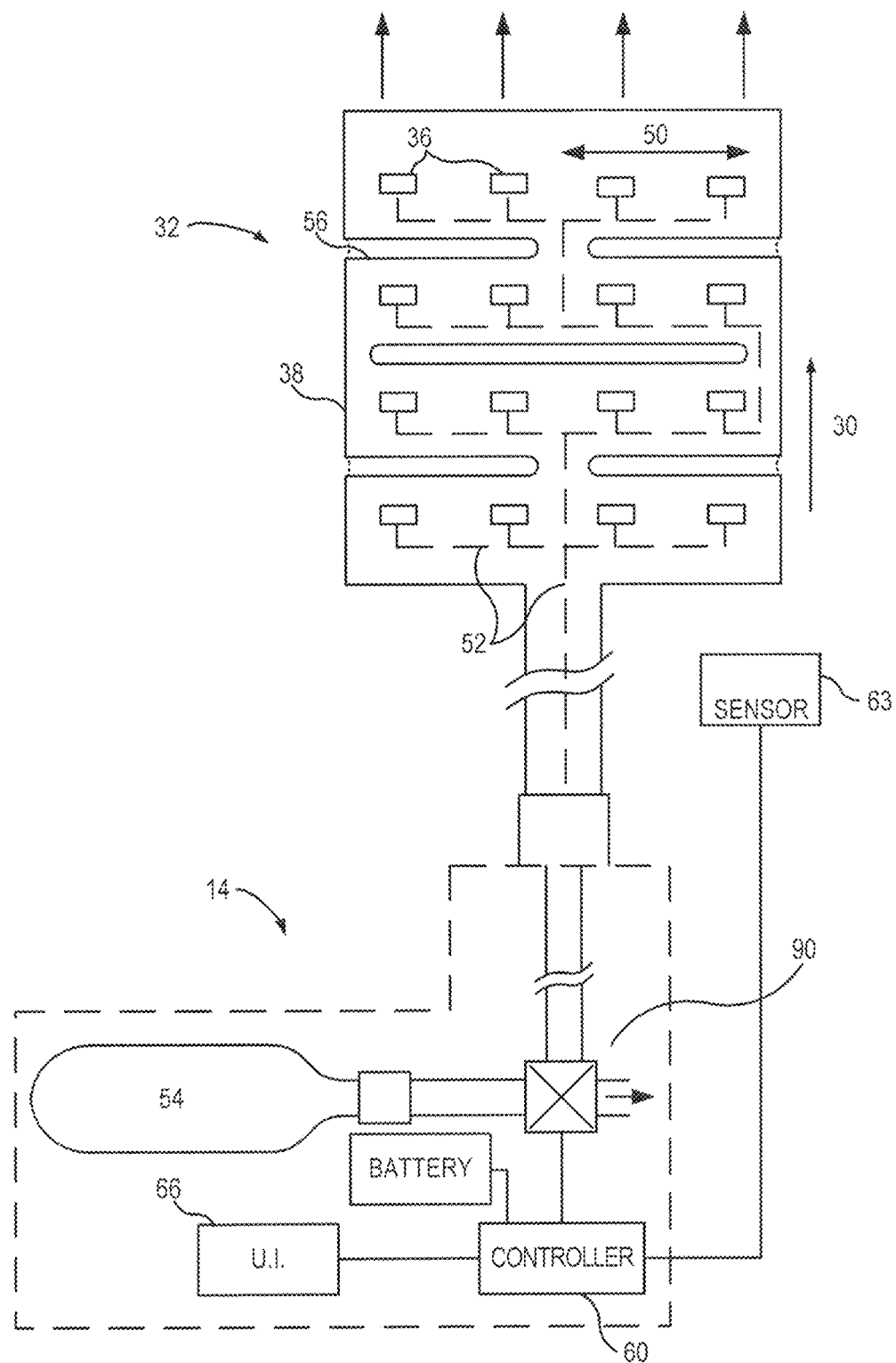
FIG. 7 schematically illustrates components for use in the catheter system of FIG. 1, including the balloon array, inflation fluid source, fluid control system, and processor.
Figure 8:
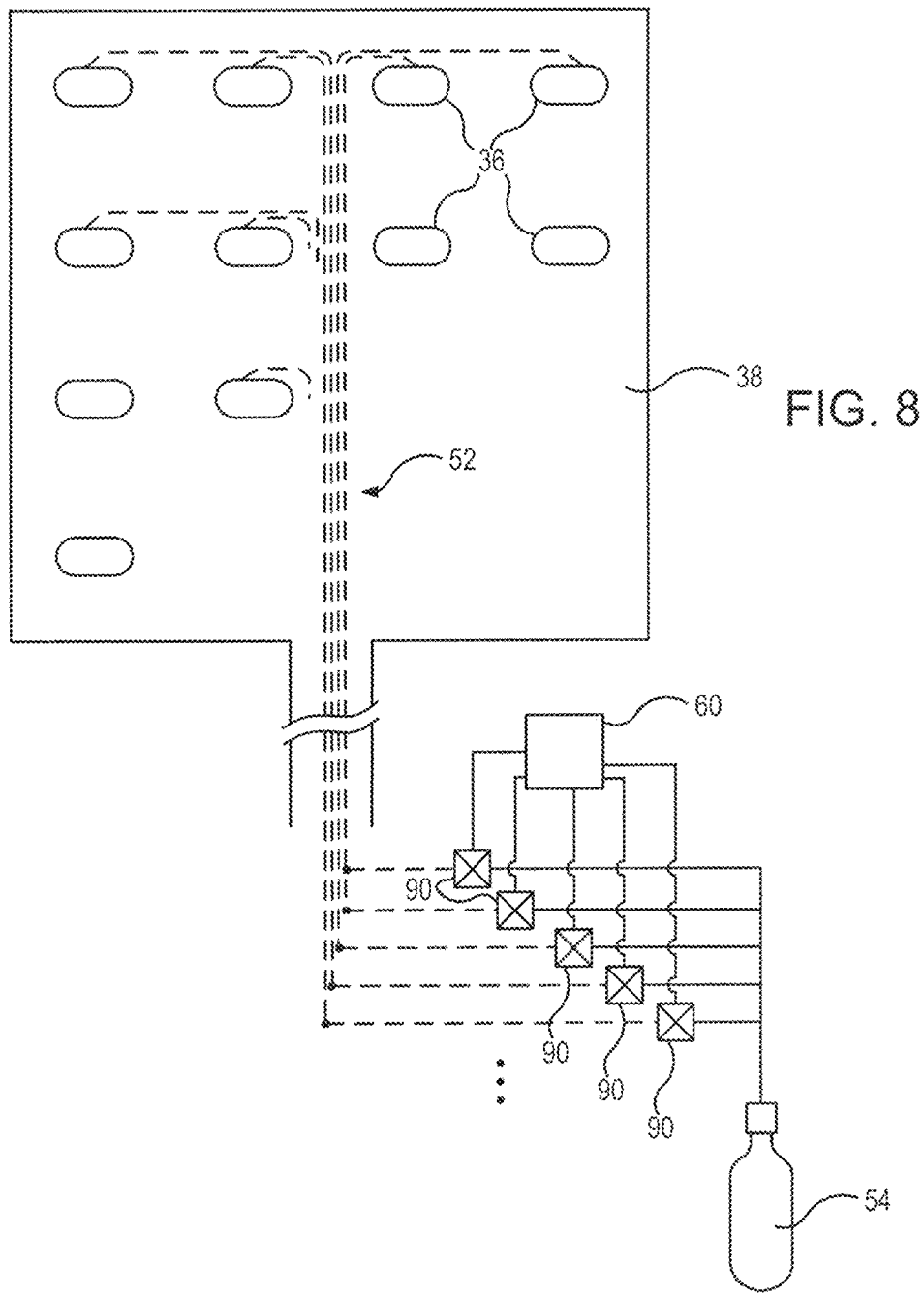
FIG. 8 is a simplified schematic of an alternative balloon array and fluid control system, in which a plurality of valves coupled with the proximal end of the catheter can be used to direct fluid to any of a plurality of channels of the array and thereby selectably determine a subset of balloons to be expanded.

When loops are included in the skeleton, actuation array 32 can be mounted to the skeleton with at least some of the balloons 36 positioned between two adjacent associated loops 42, such as between the loops of coil 34. Referring now to FIG. 5, an exemplary deflated balloon 36$i$ is located between a proximally adjacent loop 42$i$ and a distally adjacent loop 42$ii$, with a first surface region of the balloon engaging a distally oriented surface of proximal loop 34$i$, and a second surface region of the balloon engaging a proximally oriented surface of distal loop 42$ii$. The walls of deflated balloon 36$i$ have some thickness, and the proximal and distal surfaces of adjacent loops 42$i$ and 42$ii$ maintain a non-zero axial deflated offset 41 between the loops. Axial compression forces can be transferred from the loops through the solid balloon walls. Alternative skeletal structures may allow the loops to engage directly against each other so as to have a deflated offset of zero and directly transmit axial compressive force, for example by including balloon receptacles or one or more axial protrusions extending from one or both loops circumferentially or radially beyond the balloon and any adjacent substrate structure. Regardless, full inflation of the balloon will typically increase the separation between the adjacent loops to a larger full inflation offset 41'. The simplified lateral cross-sections of FIGS. 4B, 5, and 6 schematically show a direct interface engagement between a uniform thickness thin-walled balloon and a round helical coil loop. Such an interface may result in relatively limited area of the balloon wall engaging the coil and associated deformation under axial loading. Alternative balloon-engaging surface shapes along the coils (often including locally increased convex radii, locally flattened surfaces, and/or local concave balloon receptacles) and/or along the coil-engaging surfaces of the balloon (such as by locally thickening the balloon wall to spread the engagement area), and/or providing load-spreading bodies between the balloons and the coils may add axial stiffness. A variety of other modifications to the balloons and balloon/coil interfaces may also be beneficial, including adhesive bonding of the balloons to the adjacent coils, including folds or material so as to inhibit balloon migration, and the like.

Inflation of a balloon can alter the geometry along catheter body 12, for example, by increasing separation between loops of a helical coil so as to bend axis 30 of catheter 12. As can be understood with reference to FIGS. 1B, 1C and 4-5, selectively inflating an eccentric subset of the balloons can variably alter lateral deflection of the catheter axis. As can be understood with reference to FIGS. 1A, 4, and 6, inflation of all (or an axisymmetric subset) of the balloons may increase an axial length of the catheter structure. Inflating subsets of the balloons that have a combination of differing lateral orientations and axial positions can provide a broad range of potential locations and orientations of the catheter distal tip 26, and/or of one or more other locations along the catheter body (such as where a tool is mounted).

Some or all of the material of substrate 38 included in actuation array 32 will often be relatively inelastic. It may, however, be desirable to allow the skeleton and overall catheter to flex and/or elongate axially with inflation of the balloons or under environmental forces. Hence, array 32 may have cutouts 56 so as to allow the balloon array to move axially with the skeleton during bending and elongation. The array structure could alternatively (or in addition) be configured for such articulation by having a serpentine configuration or a helical coiled configuration. Balloons 36 of array 32 may include non-compliant balloon wall materials, with the balloon wall materials optionally being formed integrally from material of the substrate or separately. Note that elastic layers or other structures may be included in the substrate for use in valves and the like, and that some alternative balloons may include elastic and/or semi-compliant materials.

Figure 4A:
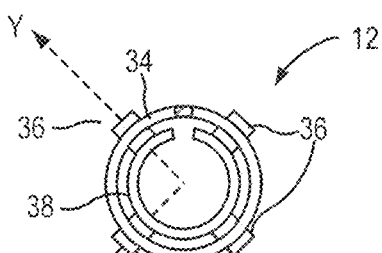
FIGS. 4A and 4B are a simplified cross-section and a simplified transverse cross-section, respectively, of an articulatable catheter for use in the system of FIG. 1, shown here with the balloons of the array in an uninflated, small axial profile configuration and between loops of the coil.
Figure 4B:
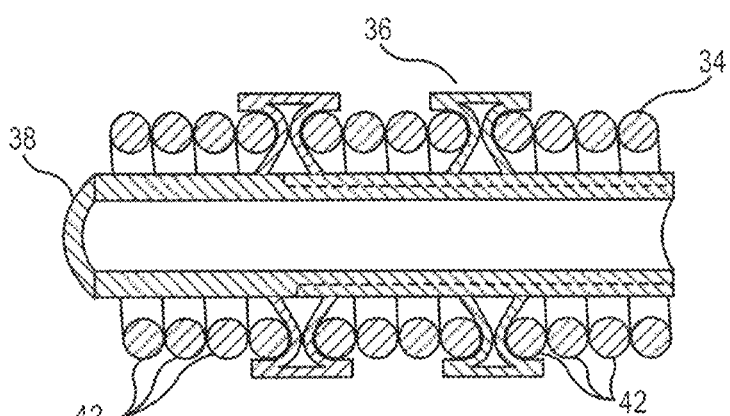

Referring to FIGS. 3, 4A, and 5, substrate 38 of array 32 is laterally flexible so that the array can be rolled or otherwise assume a cylindrical configuration when in use. The cylindrical array may be coaxially mounted to (such as being inserted into or radially outwardly surrounding) the helical coil 34 or other structural backbone of the catheter. The cylindrical configuration of the array will generally have a diameter that is equal to or less than an outer diameter of the catheter. The opposed lateral edges of substrate 38 may be separated by a gap as shown, may contact each other, or may overlap. Contacting or overlapping edges may be affixed together (optionally so as to help seal the catheter against radial fluid flow) or may accommodate relative motion (so as to facilitate axil flexing). In some embodiments, lateral rolling or flexing of the substrate to form the cylindrical configuration may be uniform (so as to provide a continuous lateral curve along the major surfaces), while in other embodiments intermittent axial bend regions of the substrate may be separated by axially elongate relatively flat regions of the substrate so that a cylindrical shape is approximated by a prism-like arrangement (optionally so as to limit bending of the substrate along balloons, valves, or other array components).

It will often (though not always) be advantageous to form and/or assemble one or more components of the array structure in a flat, substantially planar configuration (and optionally in a linear configuration as described below). This may facilitate, for example, partial or final formation of balloons 36 on substrate 38, or alternatively, attachment of pre-formed balloons to the substrate. The flat configuration of the substrate may also facilitate the use of known extrusion or microfluidic channel fabrication techniques to provide fluid communication channels 52 so as to selectively couple the balloons with a fluid inflation fluid source or reservoir 54, and the like. Still further advantages of the flat configuration of the substrate may include the use of electrical circuit printing techniques to fabricate electrical traces and other circuit components, automated 3-D printing techniques (including additive and/or removal techniques) for forming valves, balloons, channels, or other fluid components that will be supported by substrate 38, and the like. When the substrate is in a rolled, tubular, or flat planar configuration, the substrate will typically have a first major surface 62 adjacent balloons 36, and a second major surface 64 opposite the first major surface (with first major surface 62 optionally being a radially inner or outer surface and second major surface 64 being a radially outer or inner surface, respectively, in the cylindrical configuration). To facilitate flexing substrate 38 and array 32 into the rolled configuration, relief cuts or channels may be formed extending into the substrate from the first and/or second major surfaces, or living hinge regions may otherwise be provided between relatively more rigid portions of the substrate. To further avoid deformation of the substrate adjacent any valves or other sensitive structures, local stiffening reinforcement material may be added, and/or relief cuts or apertures may be formed partially surrounding the valves. In some embodiments, at least a portion of the array components may be formed or assembled with the substrate at least partially in a cylindrical configuration, such as by bonding layers of the substrate together while the substrate is at least locally curved, forming at least one layer of the substrate as a tube, selectively forming cuts in the substrate (optionally with a femtosecond, picosecond, or other laser) to form fluid, circuit, or other components or allow for axial flexing and elongation (analogous to cutting a stent to allow for axial flexing and radial expansion) and/or to form at least some of the channels, and bonding the layers together after cutting.

As can be understood with reference to FIGS. 5 and 6, substrate 38 of array 32 may include one or more layers of flexible substrate material. The substrate layers may comprise known flexible and/or rigid microfluidic substrate materials, such as polydimethylsiloxane (PDMS), polyimide (PI), polyethylene (PE) and other polyolefins, polystyrene (PS), polyethylene terephthalate (PET), polypropylene (PP), polycarbonate (PC), nanocomposite polymer materials, glass, silicon, cyclic olefin copolymer (COC), polymethyl methacrylate (PMMA), polyetheretherketone (PEEK), polyester, polyurethane (PU), and/or the like. These and still further known materials may be included in other components of actuation array 32, including known polymers for use in balloons (which will often include PET, PI, PE, polyether block amide (PEBA) polymers such as PEBAX™ polymers, nylons, urethanes, polyvinyl chloride (PVC), thermoplastics, and/or the like for non-compliant balloons; or silicone, polyurethane, semi-elastic nylons or other polymers, latex, and/or the like for compliant or semi-compliant balloons). Additional polymers than may be included in the substrate assembly may include valve actuation elements (optionally including shape memory alloy structures or foils; phase-change actuator materials such as paraffin or other wax, electrical field sensitive hydrogels, bimetallic actuators, piezoelectric structures, dielectric elastomer actuator (DEA) materials, or the like). Hence, while some embodiments may employ homogenous materials for actuation array 32, many arrays and substrate may instead be heterogeneous.

Fortunately, techniques for forming and assembling the components for actuation array 32 may be derived from a number of recent (and relatively widely-reported) technologies. Suitable techniques for fabricating channels in substrate layer materials may include laser micromachining (optionally using femtosecond or picosecond lasers), photolithography techniques such as dry resist technologies, embossing (including hot roller embossing), casting or molding, xerographic technologies, microthermoforming, stereolithography, 3-D printing, and/or the like. Suitable 3-D printing technologies that may be used to form circuitry, valves, sensors, and the like may include stereolithography, digital light processing, laser sintering or melting, fused deposition modeling, inkjet printing, selective deposition lamination, electron beam melting, or the like. Assembly of the components of actuation array 32 may make use of thermal or adhesive bonding between layers and other components, though laser, ultrasound, or other welding techniques; microfasteners, or the like may also be used. Electrical element fabrication of conductive traces, actuation, signal processor, and/or sensor components carried by substrate 38 may, for example, use ink-jet or photolithography techniques, 3-D printing, chemical vapor deposition (CVD) and/or more specific variants such as initiated chemical vapor deposition (iCVD), robotic microassembly techniques, or the like, with the electrical traces and other components often comprising inks and other materials containing metals (such as silver, copper, or gold) carbon, or other conductors. Many suitable fabrication and assembly techniques have been developed during development of microfluidic lab-on-a-chip or lab-on-a-foil applications. Techniques for fabricating medical balloons are well developed, and may optionally be modified to take advantage of known high-volume production techniques (optionally including those developed for fabricating bubble wrap, for corrugating extruded tubing, and the like). Note that while some embodiments of the actuation array structures described herein may employ fluid channels sufficiently small for accurately handling of picoliter or nanoliter fluid quantities, other embodiments will include channels and balloons or other fluid-expandable bodies that utilize much larger flows so as to provide desirable actuation response times. Balloons having at least partially flexible balloon walls may provide particular advantages for the systems described herein, but alternative rigid fluid expandable bodies such as those employing pistons or other positive displacement expansion structures may also find use in some embodiments.

The structures of balloons 36 as included in actuation array 32 may be formed of material integral with other components of the array, or may be formed separately and attached to the array. Balloons 36 may be formed from or attached to a first sheet of substrate material that can be bonded or otherwise affixed to another substrate layer or layers. The material of the balloon layer may optionally cover portions of the channels directly, or may be aligned with apertures that open through an intermediate substrate layer surface between the channels and the balloons. Alternative methods for fabricating individual balloons are well known, and the formed balloons may be affixed to the substrate 38 by adhesive bonding. Balloon shapes may comprise relatively simple cylinders or may be somewhat tailored to taper to follow an expanded offset between loops of a coil, to curve with the cylindrical substrate and/or to engage interface surfaces of the skeleton over a broader surface area and thereby distribute actuation and environmental loads. Effective diameters of the balloons in the array may range from about 0.003 mm to as much as about 2 cm (or more), more typically being in a range from about 0.3 mm to about 2 mm or 5 mm, with the balloon lengths often being from about 2 to about 15 times the diameter. Typical balloon wall thicknesses may range from about 0.0002 mm to about 0.004 mm (with some balloon wall thicknesses being between 0.0002 mm and 0.020 mm), and full inflation pressures in the balloons may be from about 0.2 to about 40 atm, more typically being in a range from about 0.4 to about 30 atm, and in some embodiments being in a range from about 10 to about 30 atm, with high-pressure embodiments operating at pressures in a range as high as 20-45 atm and optionally having burst pressures of over 50 atm.

Referring now to FIG. 5, balloons 36 will generally be inflated using a fluid supply system that includes a fluid source 54 (shown here as a pressurized single-use cartridge) and one or more valves 90. At least some of the valves 90 may be incorporated into the balloon array substrate, with the valves optionally being actuated using circuitry printed on one or more layers of substrate 38. With or without substrate-mounted valves that can be used within a patient body, at least some of the valves may be mounted to housing 14, or otherwise coupled to the proximal end of catheter 12. Valves 90 will preferably be coupled to channels 52 so as to allow the fluid system to selectively inflate any of a plurality of alternative individual balloons or subsets of balloons 36 included in actuation array 32, under the direction of a processor 60. Hence, processor 60 will often be coupled to valves 90 via conductors, the conductors here optionally including flex circuit traces on substrate 38.

Referring still to FIG. 5, fluid source 54 may optionally comprise a separate fluid reservoir and a pump for pressurizing fluid from the reservoir, but will often include a simple tank or cartridge containing a pressurized fluid, the fluid optionally being a gas or a gas-liquid mixture. The cartridge will often maintain the fluid at a supply pressure at or above a full inflation pressure range of balloons 36, with the cartridge optionally being gently heated by a resistive heater or the like (not shown) in housing 14 so as to maintain the supply pressure within a desired range in the cartridge during use. Supply pressures will typically exceed balloon inflation pressures sufficiently to provide balloon inflation times within a target threshold given the pressure loss through channels 52 and valves 90, with typical supply pressures being between 10 and 210 atm, and more typically being between 20 and 60 atm. Suitable fluids may include known medical pressurized gases such as carbon dioxide, nitrogen, oxygen, nitrous oxide, air, known industrial and cryogenic gasses such as helium and/or other inert or noble gasses, refrigerant gases including fluorocarbons, and the like. Note that the pressurized fluid in the canister can be directed via channels 52 into balloons 36 for inflation, or the fluid from the canister (often at least partially a gas) may alternatively be used to pressurize a fluid reservoir (often containing or comprising a benign biocompatible liquid such as water or saline) so that the balloon inflation fluid is different than that contained in the cartridge. Where a pressurized liquid or gas/liquid mixture flows distally along the catheter body, enthalpy of vaporization of the liquid in or adjacent to channels 52, balloons 36, or other tissue treatment tools carried on the catheter body (such as a tissue dilation balloon, cryogenic treatment surface, or tissue electrode) may be used to therapeutically cool tissue. In other embodiments, despite the use of fluids which are used as refrigerants within the body, no therapeutic cooling may be provided. The cartridge may optionally be refillable, but will often instead have a frangible seal so as to limit re-use.

As the individual balloons may have inflated volumes that are quite small, cartridges that are suitable for including in a hand-held housing can allow more than a hundred, optionally being more than a thousand, and in many cases more than ten thousand or even a hundred thousand individual balloon inflations, despite the cartridge containing less than 10 ounces of fluid, often less than 5 ounces, in most cases less than 3 ounces, and ideally less than 1 ounce. Note also that a number of alternative fluid sources may be used instead of or with a cartridge, including one or more positive displacement pumps (optionally such as simple syringe pumps), a peristaltic or rotary pump, any of a variety of microfluidic pressure sources (such as wax or other phase-change devices actuated by electrical or light energy and/or integrated into substrate 38), or the like. Some embodiments may employ a series of dedicated syringe or other positive displacement pumps coupled with at least some of the balloons by channels of the substrate, and/or by flexible tubing.

Referring still to FIG. 5, processor 60 can facilitate inflation of an appropriate subset of balloons 36 of actuation array 32 so as to produce a desired articulation. Such processor-derived articulation can significantly enhance effective operative coupling of the input 18 to the actuated portion 20 of catheter body 12, making it much easier for the user to generate a desired movement in a desired direction or to assume a desired shape. Suitable correlations between input commands and output movements have been well developed for teleoperated systems with rigid driven linkages. For the elongate flexible catheters and other bodies used in the systems described herein, it will often be advantageous for the processor to select a subset of balloons for inflation based on a movement command entered into a user interface 66 (and particularly input 18 of user interface 66), and on a spatial relationship between actuated portion 20 of catheter 12 and one or more component of the user interface. A number of differing correlations may be helpful, including orientational correlation, displacement correlation, and the like. Along with an input, user interface 66 may include a display showing actuated portion 20 of catheter body 12, and sensor 63 may provide signals to processor 60 regarding the orientation and/or location of proximal base 21. Where the relationship between the input, display, and sensor are known (such as when they are all mounted to proximal housing 14 or some other common base), these signals may allow derivation of a transformation between a user interface coordinate system and a base coordinate system of actuated portion 20. Alternative systems may sense or otherwise identify the relationships between the sensor coordinate system, the display coordinate system, and/or the input coordinate system so that movements of the input result in catheter movement, as shown in the display. Where the sensor comprises an image processor coupled to a remote imaging system (such as a fluoroscopy, MRI, or ultrasound system), high-contrast marker systems can be included in proximal base 21 to facilitate unambiguous determination of the base position and orientation. A battery or other power source (such as a fuel cell or the like) may be included in housing 14 and coupled to processor 60, with the housing and catheter optionally being used as a handheld unit free of any mechanical tether during at least a portion of the procedure. Nonetheless, it should be noted that processor 60 and/or sensor 63 may be wirelessly coupled or even tethered together (and/or to other components such as a separate display of user interface 66, an external power supply or fluid source, or the like).

Regarding processor 60, sensor 63, user interface 66, and the other data processing components of system 10, it should be understood that the specific data processing architectures described herein are merely examples, and that a variety of alternatives, adaptations, and embodiments may be employed. The processor, sensor, and user interface will, taken together, typically include both data processing hardware and software, with the hardware including an input (such as a joystick or the like that is movable relative to housing 14 or some other input base in at least 2 dimensions), an output (such as a medical image display screen), an image-acquisition device or other sensor, and one or more processor. These components are included in a processor system capable of performing the image processing, rigid-body transformations, kinematic analysis, and matrix processing functionality described herein, along with the appropriate connectors, conductors, wireless telemetry, and the like. The processing capabilities may be centralized in a single processor board, or may be distributed among the various components so that smaller volumes of higher-level data can be transmitted. The processor(s) will often include one or more memory or storage media, and the functionality used to perform the methods described herein will often include software or firmware embodied therein. The software will typically comprise machine-readable programming code or instructions embodied in non-volatile media, and may be arranged in a wide variety of alternative code architectures, varying from a single monolithic code running on a single processor to a large number of specialized subroutines being run in parallel on a number of separate processor sub-units.

Referring now to FIG. 6, an alternative actuation array and fluid supply system are shown schematically. As in the above embodiment, balloons 36 are affixed along a major surface of substrate 38, optionally prior to rolling the substrate and mounting of the actuation array to the skeleton of the catheter body. In this embodiment, each balloon has an associated dedicated channel 52 of substrate 38, and also an associated valve 90. Processor 60 is coupled with valves 90, and by actuating a desired subset of the valves the associated subset of balloons can be inflated or deflated. In some embodiments, each valve can be associated with more than one balloon 36, so that (for example), opening of a single valve might inflate a plurality (optionally 2, 3, 4, 8, 12, or some other desired number) of balloons, such as laterally opposed balloons so as to elongate the distal portion of the catheter. In these or other embodiments, a plurality of balloons (2, 3, 4, 5, 8, 12, or another desired number) on one lateral side of the catheter could be in fluid communication with a single associated valve 90 via a common channel or multiple channels so that opening of the valve inflates the balloons and causes a multi-balloon and multi-increment bend in the axis of the catheter. Still further variations are possible. For example, in some embodiments, channels 52 may be formed at least in-part by flexible tubes affixed within an open or closed channel of substrate 38, or glued along a surface of the substrate. The tubes may comprise polymers (such as polyimide, PET, nylon, or the like), fused silica, metal, or other materials, and suitable tubing materials may be commercially available from Polymicro Technologies of Arizona, or from a variety of alternative suppliers. The channels coupled to the proximal end of the actuatable body may be assembled using stacked fluidic plates, with valves coupled to some or all of the plates. Suitable electrically actuated microvalues are commercially available from a number of suppliers. Optional embodiments of fluid supply systems for all balloon arrays described herein may have all values mounted to housing 14 or some other structure coupled to and/or proximal of) the proximal end of the elongate flexible body. Advantageously, accurately formed channels 52 (having sufficiently tight tolerance channel widths, depths, lengths, and/or bends or other features) may be fabricated using microfluidic techniques, and may be assembled with the substrate structure, so as to meter flow of the inflation fluid into and out of the balloons of all of the actuation arrays described herein.

A variety of known lab-on-a-chip and lab-on-a-foil production techniques can be used to assemble and seal the substrate layers, with many embodiments employing thermal fusion bonding, solvent bonding, welding (and particularly ultrasound welding), UV-curable adhesives, contact adhesives, nano-adhesives (including doubly cross-linked nano-adhesive or DCNA), epoxy-containing polymers (including polyglycidyl methacrylate), plasma or other surface modifications, and/or the like between layers. For high fluid pressure systems, third generation nano-adhesive techniques such as CVD deposition of less than 400 nanometer layers of DCNA materials may facilitate the use of high-strength polymer materials such as PET. Channels of such high-pressure systems may optionally be defined at least in part by PET and/or fused silica tubing (which may be supported by a substrate along some or all of the channel, and/or may be bundled together with other fused silica tubing along some or all of its length ideally in an organized array with tubing locations corresponding to the balloon locations within the balloon array, analogous to the organization of a coherent fiber optic bundle), or the like. Any valves mounted to the substrate of the balloon array may be electrically actuated using conductive traces deposited on a surface of a substrate layer prior to bonding, with an overlying layer sealing the traces in the interior of the substrate. Valve members may move when a potential is applied to an actuation material using the traces, with that material optionally comprising a shape-memory alloy, piezoelectric, an electrically actuated polymer, or the like. Still further alternative actuation materials may include phase change materials such as wax or the like, with the phase change being induced by electrical energy or optical energy (such as laser light transmitted via an optical fiber or printed pathway between layers of the substrate). In some embodiments, the actuation material and valve member may be formed using 3-D printing techniques. Multiplex circuitry may be included in, deposited on a layer of, or affixed to substrate 38 so that the number of electrical traces extending proximally along catheter body 12 may be less than the number of valves that can be actuated by those valves. The valves may take any of a wide variety of forms, and may employ (or be derived from) known valve structures such as known electrostatically-actuated elastomeric microfluidic valves, microfluidic polymer piston or free-floating gate valves, layered modular polymeric microvalves, dielectric elastomer actuator valves, shape memory alloy microvalves, hydrogel microactuator valves, integrated high-pressure fluid manipulation valves employing paraffin, and the like. Along with electrically actuated microvalves, suitable valves may be optically actuated, fluid actuated, or the like.

It should be understood that many of the valves shown herein are schematic, and that additional or more complex valves and channel systems may be included to control inflation and deflation of the balloons. One or more valves in the system may comprise gate valves (optionally normally closed, normally open or stable), so as to turn inflation fluid flow from the fluid source to at least one balloon on or off. Deflation may optionally be controlled by a separate gate valve between each balloon (or groups of balloons) and one or more deflation port of substrate 38 (the fluid from the balloon optionally exiting from the substrate to flow proximally between radially inner and outer sealed layers of the catheter) or housing 14. Alternative 2-way valves may allow i) communication between either the fluid source and the balloon (with flow from the balloon being blocked), or ii) between the balloon and the deflation outflow (with the flow from the fluid source being blocked). Still further alternatives may be employed, including a 3 way valve having both of the above modes and iii) a sealed balloon mode in which the balloon is sealed from communication with the fluid source and from the deflation outflow (with flow from the source also being closed).

Figure 9:
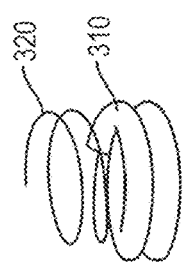
Figure 11:
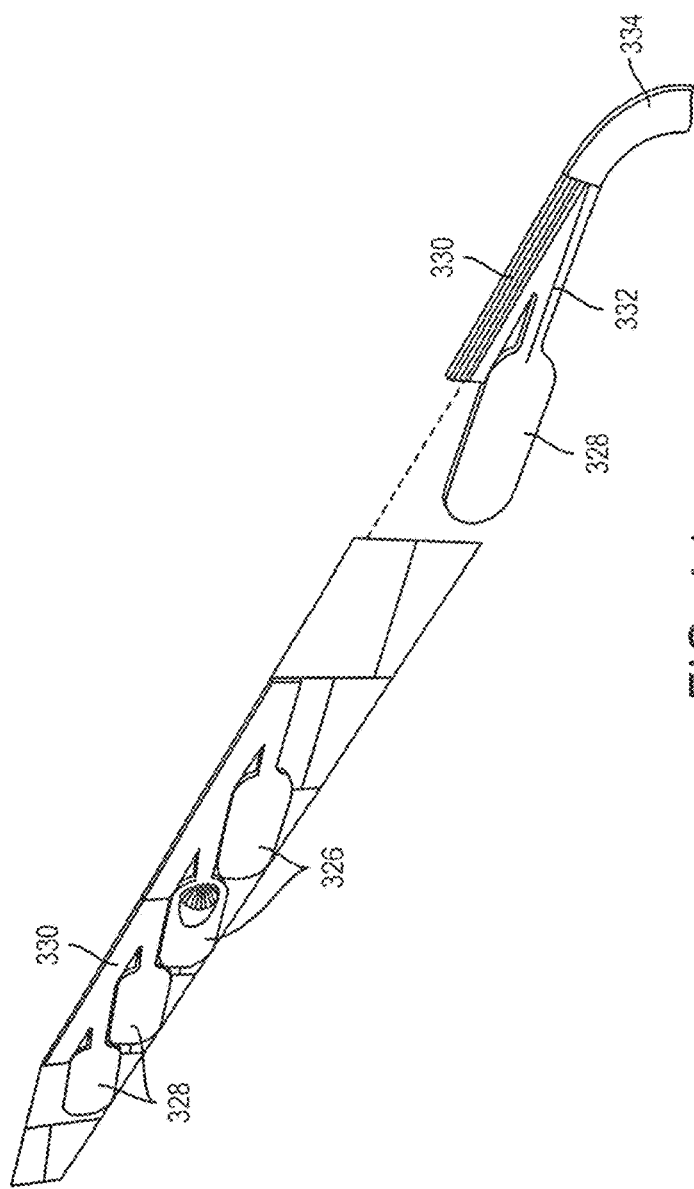

Referring now to FIG. 9, selected components of an articulated portion 302 of an articulated catheter 304 can be seen in more detail. A plurality of inflated balloons 306 are offset from an axis 308 of catheter 304 along a first lateral orientation +X, so that the balloons urge corresponding pairs of axial (proximal and distal) surfaces on the loops of coil 310 apart. This urges the coil to bend away from inflated balloons 306 away from the +X orientation and toward the −X lateral orientation. Uninflated balloons 312a, 312b, and 312c are offset in the lateral −X, −Y, and +Y orientations, respectively, allowing selective inflations of differing subsets of these balloons to bend axis 308 in differing directions. Inflation of opposed balloons (such as −X and +X, or −Y and +Y, or both) may elongate coil 314 along axis 308. Note that a distal portion of coil 314 has been omitted from the drawing so that the arrangement of the balloons can be more clearly seen. This embodiment shows relatively standard offset balloon shapes, with the axes of the balloons bent to follow the coil. In this and other embodiments, a single balloon between coils may impose a bend in axis 308 in a range from 1 to 20 degrees, more typically being in a range from 2½ to 15 degrees, and often being from 6 to 13 degrees. To allow a single inflation lumen to achieve greater bend angles, 2, 3, 4, or more balloon inflation lumens or ports adjacent the balloons may be in fluid communication with a single common fluid inflation lumen.

Figure 10:
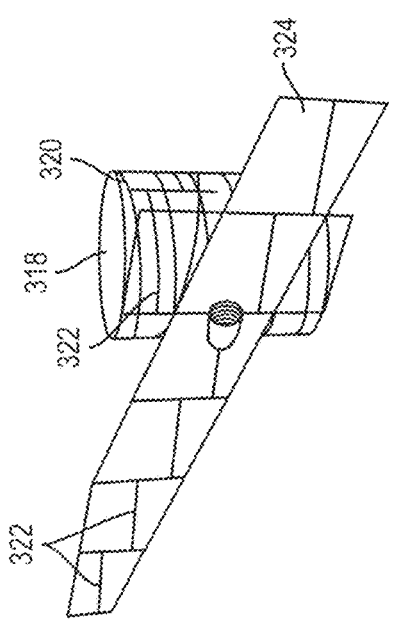
FIGS. 9-12 are perspective drawings showing an exemplary flat-pattern substrate and associated balloon array generated by unwinding a helical balloon pattern, along with an exemplary bonded balloon fabrication technique.
Figure 12:

Referring now to FIGS. 9-12, an exemplary integrated balloon array and array substrate design and fabrication process can be understood. As seen in FIGS. 9 and 10, a cylinder 318 is defined having a diameter corresponding to a helical coil axis 320 of coil 310, with the coil axis typically corresponding to the central axis of the coil wire (so that the helical axis winds around the central axis of the elongate body). Desired balloon centerlines 322 are here defined between loops of the coil. Alternative balloon centerlines may extend along the coil axis, as can be understood with other embodiments described below. A flat pattern 324 of the balloon centerlines 322 can be unwrapped from cylinder 318, with the flat pattern optionally forming a repeating pattern extending along a helical wrap of the cylinder, the helical pattern unwrap optionally being counterwound relative to coil 310 and typically having a pitch which is greater than that of the coil. As can be understood with reference to FIGS. 11 and 12, the repeated flat pattern 324 can be used to define a repeating substrate pattern 326, with the substrate pattern here including, for each balloon in this portion of the array, a balloon portion 328, a multi-lumen channel portion 330, and a connector portion 332 for connecting the balloon to the multi-lumen channel portion. The connector portions and balloons here extend from a single side of the multi-lumen channel portion; alternative embodiments may have connector portions and balloons extending from both lateral or circumferential sides. The loops of the substrate helix may also overlap. In other embodiments, the flat pattern (and associated substrate and multi-lumen channels) may wind in the same direction as the coil, with the balloons and channel structures optionally extending along a contiguous strip, the balloons optionally having channels along one or both axial sides of the strip and the balloons protruding radially from the strip and between the loops of the coil so that connector portions 332 may optionally be omitted. Such embodiments may benefit from a thicker and/or polymer coil. Regardless, the helical balloon array structure may facilitate lateral bending of the catheter along its axis and/or axial elongation of the catheter without kinking or damaging the substrate material along the fluid flow channels, as the substrate loops may slide relative to each other along an inner or outer surface of coil 310 (often within a sealed annular space between inner and outer sheaths bordering the inner and outer surfaces of the catheter).

Advantageously, the substrate pattern may then be formed in layers as generally described above, with at least a portion (often the majority) of each balloon being formed from sheet material in a first or balloon layer 334 (optionally by blowing at least a portion of the balloon from suitable sheet material into a balloon tool) and some or all of the channels being formed from sheet material in a second or channel layer 336. The layers can be bonded together to provide sealed fluid communication between the balloons and the other components of the fluid supply system, with the outline shapes of the balloon portions 328, connector portions 332, and channel portions being cut before bonding, after bonding, or partly before and partly after. Note that a portion of the balloon shape may be imposed on the channel layer(s) and that a plurality of channel layers may be used to facilitate fluid communication between a plurality of helically separated balloons (including balloons along a single lateral orientation of the assembled catheter) and a common fluid supply channel. Similarly, a portion (or even all) of the channel structure might alternatively be imposed on the balloon layer, so that a wide variety of architectures are possible. Formation of multiple balloons 334 and channels 330, and bonding of the layers can be performed using parallel or batch processing (with, for example, tooling to simultaneously blow some or all of the balloons for a helical balloon array of an articulation sub-portion, a laser micromachining station that cuts multiple parallel channels, simultaneous deposition of adhesive materials around multiple balloons and channels), or sequentially (with, for example, rolling tooling and/or roll-by stations for balloon blowing, laser cutting, or adhesive applying tooling), or a combination of both. The number of balloons included in a single helical substrate pattern may vary (typically being from 4 to 80, and optionally being from 4 to 32, and often being from 8 to 24). The balloons may be spaced for positioning along a single lateral catheter bending orientations, along two opposed orientations, along three orientations, along four orientations (as shown), or the like. Channel portion 330 may terminate at (or be integrated with) an interface with a multi-channel cable 334 that extends proximally along the coil (and optionally along other proximal balloon array portions formed using similar or differing repeating balloon substrate patterns). A wide variety of alternative balloon shapes and balloon fabrication techniques may be employed, including blowing a major balloon portion from a first sheet material and a minor portion from a second sheet material, and bonding the sheets surrounding the blow portions together with the bond axially oriented (as shown in FIG. 10) so that the sheets and substrate layers are oriented along a cylinder bordering the coil, or with the bond radially oriented so that the sheet material adjacent the bonds is connected to adjacent substrate by a bent connector portion or tab.

Figure 13:
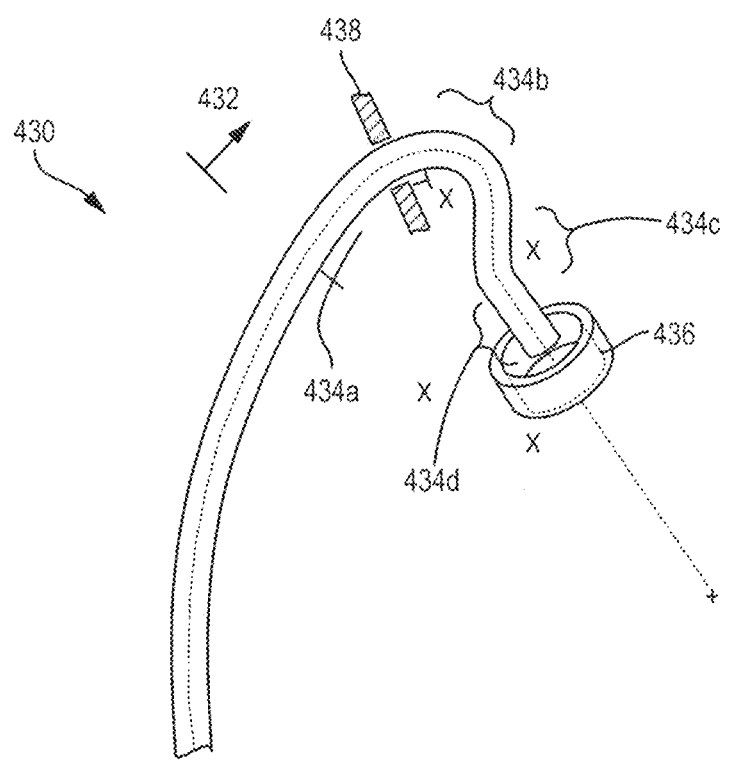
FIG. 13 schematically illustrates bending of a diagnosis or treatment delivery catheter into alignment with a target tissue by actuating a plurality of articulation sub-portions or segments of the catheter.

Referring now to FIG. 13, an exemplary catheter 430 has an articulated portion 432 that includes a plurality of axially separate articulated segments or sub-portions 434a, 434b, 434c, and 434d. Generally, the plurality of articulation segments may be configured to facilitate aligning a distal end of the catheter with a target tissue 436. Suitable articulation segments may depend on the target tissue and planned procedure. For example, in this embodiment the articulation segments are configured to accurately align a distal end of the catheter with the angle and axial location of the native valve tissue, preferably for any patient among a selected population of patients. More specifically, the catheter is configured for aligning the catheter axis at the distal end of the catheter with (and particularly parallel to) an axis of the target tissue, and (as measured along the axis of the catheter) for axially aligning the end of the catheter with the target tissue. Such alignment may be particularly beneficial, for example, for positioning a prosthetic cardiac valve (optionally an aortic valve, pulmonary valve, or the like, and particularly a mitral valve) with tissues of or adjacent a diseased native valve. Suitable catheter articulation capabilities may also, in part, depend on the access path to the target tissue. For alignment with the mitral valve, the catheter may, for example, be advanced distally into the right atrium via the superior or inferior vena cava, and may penetrate from the right atrium through the septum 438 into the left atrium. Suitable transseptal access may be accomplished using known catheter systems and techniques (though alternative septal traversing tools using the articulated structures described herein might alternatively be used). Regardless, to achieve the desired alignment with the native valve tissue, the catheter may be configured to, for example: 1) from distally of (or near) the septum, form a very roughly 90 degree bend (+/−a sufficient angle so as to accommodate varying physiologies of the patients in the population); 2) extend a distance in desired range in three dimensions, including a) apically from the septal penetration site and b) away from the plane of the septal wall at the penetration; and 3) orient the axis of the catheter at the distal end in three dimensions and into alignment with the native valve tissue.

To achieve the desired alignment, catheter 430 may optionally provide consistent multi-axis bend capabilities as well as axial elongation capabilities, either continuously along the majority of articulatable portion 432 of catheter 430, or in articulated segments at regular intervals extending therealong. Alternative approaches may employ more functionally distinguished articulation segments. When present, each segment may optionally have between 4 and 32 balloons, subsets of the balloons within that segment optionally being oriented along from 1 to 4 lateral orientations. In some embodiments, the axis bending balloons within at least one segment may all be aligned along a single bend orientation, and may be served by a single inflation lumen, often served by a modulated fluid supply that directs a controlled inflation fluid volume or pressure to the balloons of the segment to control the amount of bending in the associated orientation. Alternative single lateral bending direction segments may have multiple sets of balloons served by different lumens, as described above. For example, segments 434a and 434b may both comprise single direction bending segments, each capable of imposing up to 60 degrees of bend angle and with the former having a first, relatively large bend radius in the illustrated configuration due to every-other axial balloon being inflated, or due to inflation with a limited quantity of inflation fluid. In segment 434*b*, all but the distal-most four balloons may be inflated, resulting in a smaller bend radius positioned adjacent segment 434*a*, with a relatively straight section of the catheter distal of the bend. Segment 434*c* may have balloons with four different bend orientations at a relatively high axial density, here having selected transverse balloons (such as 6+X balloons and 2−Y balloons) inflated so as to urge the catheter to assume a shape with a first bend component away from the septal plane and a second bend component laterally away from the plane of the bends of segments 434*a* and 434*b*. Segment 434*d* may comprise an axial elongation segment, with opposed balloons in fluid communication with the one or more inflation fluid supply lumen of this segment. Axial positioning of the end of the catheter may thus be accurately controlled (within the range of motion of the segment) by appropriate transmission of inflation fluid. Advantageously, such specialized segments may limit the number of fluid channels (and the cost, complexity and/or size of the catheter) needed to achieve a desired number of degrees of freedom and a desired spatial resolution. It should be understood that alternative segment arrangements might be employed for delivery of a prosthetic heart valve or the like, including the use of three segments. The valve might be positioned using a three-segment system by, for example, inserting the catheter so that the septum is positioned along the middle of the three segments, ideally with the catheter traversing the septum at or near the middle of the middle segment.

Figure 14:
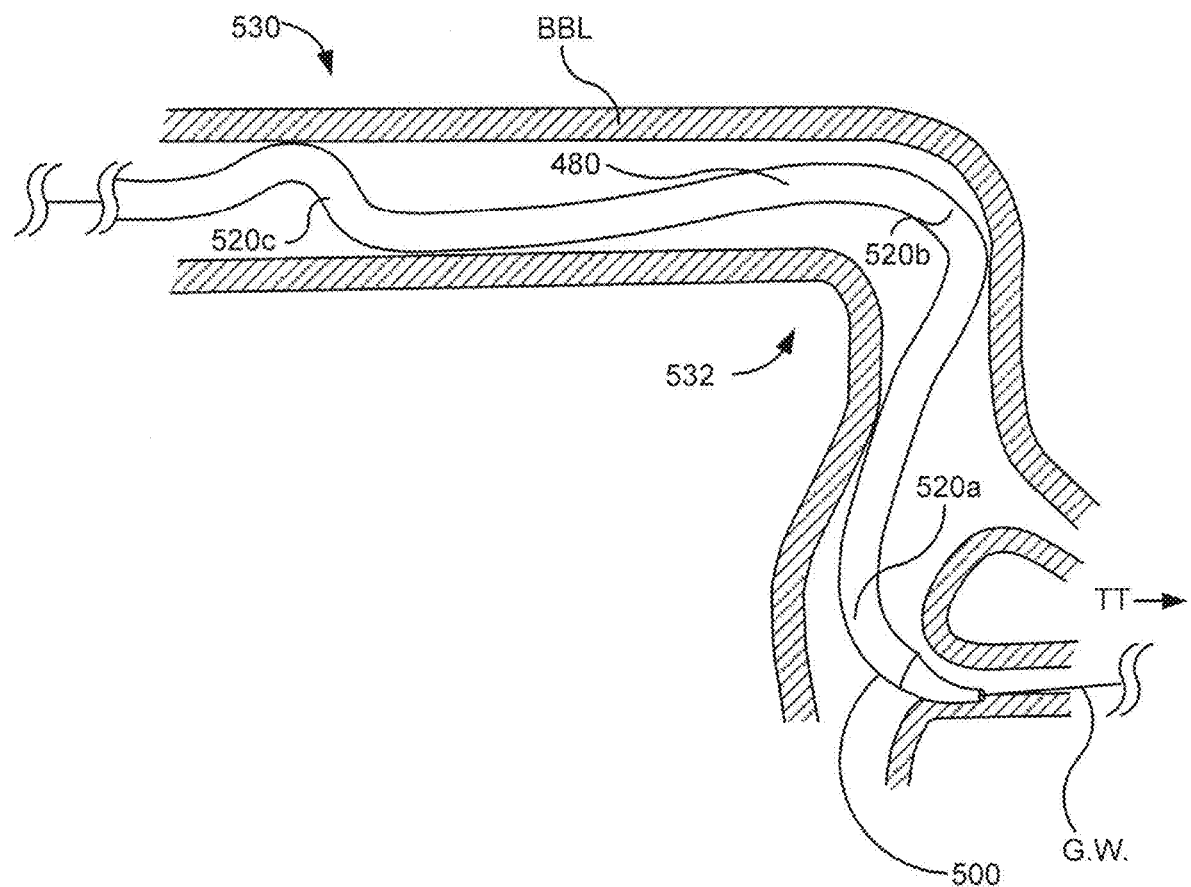
FIG. 14 schematically illustrates lateral deflection of an articulated catheter to provide gentle and releasable anchoring of the catheter within the body lumen, use of an anchored catheter as a base for 3-D steering of a catheter, and sensing of a curved path distal of and end of a catheter body by detecting deflection of soft distal guide tip against a lumen wall and/or guidewire.

Referring now to FIG. 14, two different anchor modes of catheter 480 can be understood. In this embodiment, it is desired to align distal end 500 of catheter 480 with a target tissue TT that is accessed via a branching body lumen BBL. To access the target tissue and/or to produce the desired alignment, catheter 480 may advance over a guidewire GW, or may be self-guiding, and will use lateral deflection and axial elongation of a distal articulable catheter segment 520*a* as generally described above. The system user has here determined it would be desirable to anchor the catheter 480 proximally of segment 520*a*, for example, so that the distal segment of the catheter will move with physiological movement near the target tissue TT, so that the distal segment of the catheter is isolated from movement proximal of the anchor location, to stabilize segment 520*a* during articulation, or the like. To provide a desired anchoring engagement between an outer surface of catheter 480 and the luminal wall at a first anchoring location 530 extending along a relatively straight section of the branching body lumen BBL, catheter articulation segment 520*c* may be driven so as to impose at least one bend and preferably so as to impose opposed bends, sinusoidal bends, a helical bend, or the like. Anchoring engagement at a bent location 532 of the body lumen can be provided by driving articulation segment 520*b* toward a catheter bend configuration having a bend angle which is greater than that of the body lumen bend. Note that FIG. 14 also illustrates lateral deflection of a flexible tip 534 of catheter 480 as imposed by guidewire GW, the lumen wall, or both. Such a flexible tip having a flex sensor (optionally an optical fiber or flex circuit) can measure such deflection and generate signals that may be used as a distal path curve sensor, as can be understood above.

Figure 15:
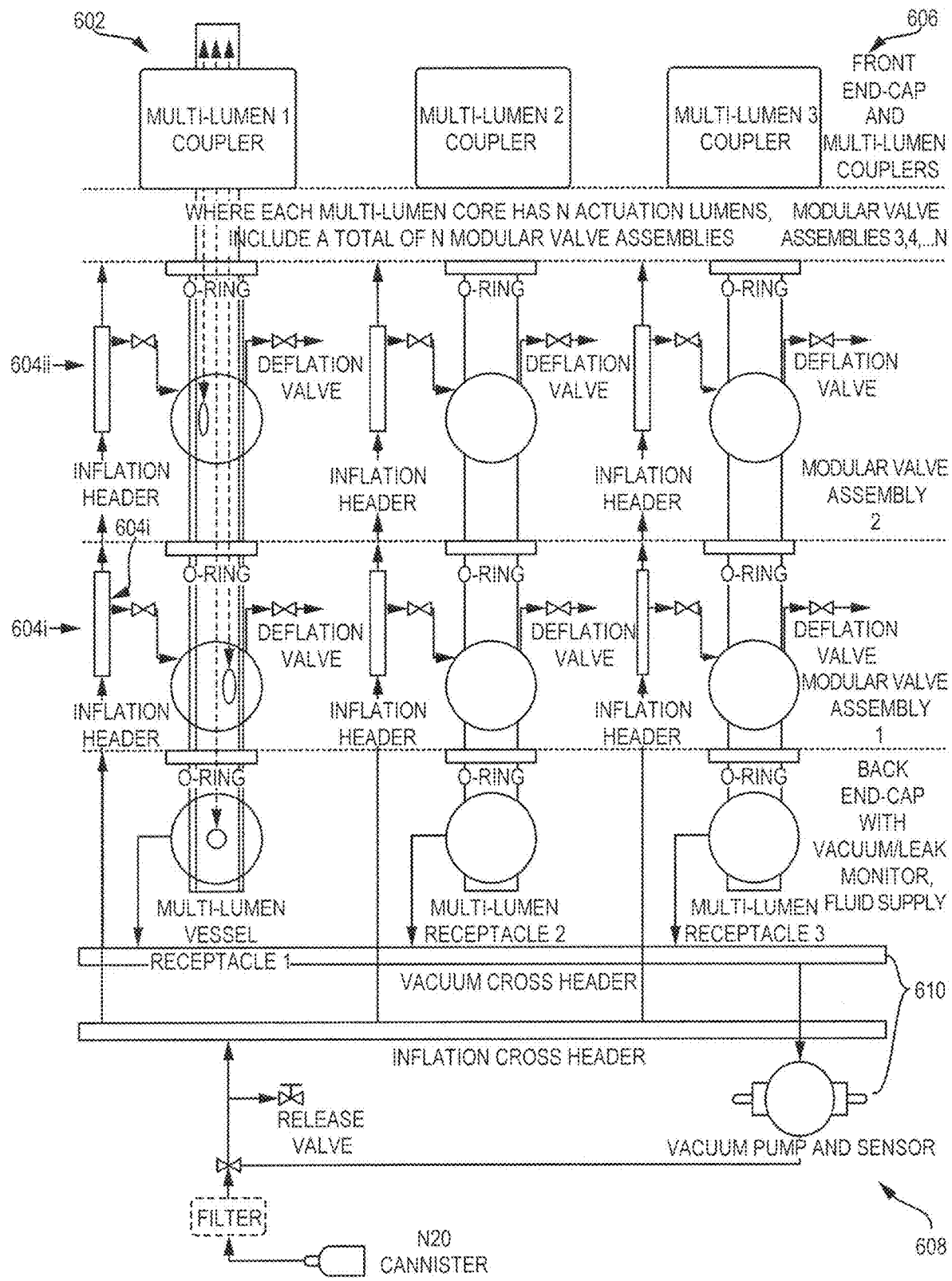
FIG. 15 is a simplified schematic of a modular manifold having a stack of valve plate assemblies through which a multi-lumen connector extends so as to provide controlled fluid flow to and from balloons of an array.

Referring now to FIG. 15, a simplified manifold schematic shows fluid supply and control components of an alternative manifold 602. As generally described above, manifold 602 has a plurality of modular manifold units or valve assembly plates 604*i*, 604*ii*, . . . stacked in an array. The stack of valve plates are sandwiched between a front end cap 606 and a back end-cap 608, and during use the proximal portion of the multi-lumen conduit core(s) extend through apertures in the front cap and valve plates so that the proximal end of the core is adjacent to or in the back cap, with the apertures defining a multi-lumen core receptacle. The number of manifold units or modules in the stack is sufficient to include a plate module for each lumen of each of the multi-lumen core(s). For example, where an articulatable structure has 3 multi-lumen core shafts and each shaft has 6 lumens, the manifold assembly may include a stack of 6 plates. Each plate optionally includes an inflation valve and a deflation valve to control pressure in one of the lumens (and the balloons that are in communication with that lumen) for each multi-lumen shaft. In our 3-multi-lumen shaft/6 lumen each example, each plate may include 3 inflation valves (one for a particular lumen of each shaft) and 3 deflation valves (one for that same lumen of each shaft). As can be understood with reference to the multi-lumen shaft shown in receptacle 1 of FIG. 15, the spacing between the ports along the shaft corresponds to the spacing between the fluid channels along the receptacle. By inserting the core shaft fully into the multi-lumen shaft receptacle, the plate channel locations can be registered axially with the core, and with the ports that were drilled radially from the outer surface of the multi-lumen core. The processor can map the axial locations of the valves along the receptacle with the axial locations of the ports along the core shafts, so that a port into a particular lumen of the core can be registered and associated with a fluid channel of specific inflation and deflation valves. One or more inflation headers can be defined by passages axially through the valve-unit plates; a similar deflation header (not shown) can also be provided to monitor pressure and quantity of fluid released from the lumen system of the articulated device. O-rings can be provided adjacent the interface between the plates surrounding the headers and receptacles. Pressure sensors (not shown) can monitor pressure at the interface between each plate and the multi-lumen receptacle.

Along with monitoring and controlling inflation and deflation of all the balloons, manifold 602 can also include a vacuum monitor system 610 to verify that no inflation fluid is leaking from the articulated system within the patient body. A simple vacuum pump (such as a syringe pump with a latch or the like) can apply a vacuum to an internal volume or chamber of the articulated body surrounding the balloon array. Alternative vacuum sources might include a standard operating room vacuum supply or more sophisticated powered vacuum pumps. Regardless, if the seal of the vacuum chamber degrades the pressure in the chamber of the articulated structure will increase. In response to a signal from a pressure sensor coupled to the chamber, a shut-off valve can automatically halt the flow of gas from the canister, close all balloon inflation valves, and/or open all balloon deflation valves. Such a vacuum system may provide worthwhile safety advantages when the articulated structure is to be used within a patient body and the balloons are to be inflated with a fluid that may initially take the form of a liquid but may vaporize to a gas. A lumen of a multi-lumen core shaft may be used to couple a pressure sensor of the manifold to a vacuum chamber of the articulated structure via a port of the proximal interface and an associated channel of the manifold assembly, with the vacuum lumen optionally comprising a central lumen of the multi-lumen shaft and the vacuum port being on or near the proximal end of the multi-lumen shaft.

Many of the flexible articulated devices described above rely on inflation of one or more balloons to articulate a structure from a first resting state to a second state in which a skeleton of the flexible structure is resiliently stressed. By deflating the balloons, the skeleton can urge the flexible structure back toward the original resting state. This simple system may have advantages for many applications. Nonetheless, there may be advantages to alternative systems in which a first actuator or set of actuators urges a flexible structure from a first state (for example, a straight configuration) to a second state (for example, a bent or elongate configuration), and in which a second actuator or set of actuators are mounted in opposition to the first set such that the second can actively and controllably urge the flexible structure from the second state back to the first state. Toward that end, exemplary systems described below often use a first set of balloons to locally axially elongate a structural skeleton, and a second set of balloons mounted to the skeleton to locally axially contract the structural skeleton. Note that the skeletons of such opposed balloon systems may have very little lateral or axial stiffness (within their range of motion) when no balloons are inflated.

Referring now to FIG. 16, a simplified exemplary C-channel structural skeleton 680 includes an axial series of C-channel members or frames 682, 684 extending between a proximal end (toward the bottom of the page) and a distal end (toward the top of the page) of the skeleton, with each rigid C-channel including an axial wall, a proximal flange, and a distal flange 642. The opposed major surfaces of the walls are oriented laterally, and the opposed major surfaces of the flanges are oriented axially (and more specifically distally and proximally, respectively. The C-channels alternate in orientation so that the frames are interlocked by the flanges. Hence, axially adjacent frames overlap, with the proximal and distal surfaces of two adjacent frames defining an overlap offset. The flanges also define additional offsets, with these offsets being measured between flanges of adjacent similarly oriented frames.

Balloons are disposed in the channels of each C-frame 682, 684 (only some of which are shown). Although the balloons themselves may (or may not) be structurally similar, the balloons are of two different functional types: extension balloons 660 and contraction balloons 662. Both types of balloons are disposed axially between a proximally oriented surface of a flange that is just distal of the balloon, and a distally oriented surface of a flange that is just proximal of the balloon. However, contraction balloons 662 are also sandwiched laterally between a first wall of a first adjacent C-channel 682 and a second wall of a second adjacent channel 684. In contrast, extension balloons 660 have only a single wall on one lateral side; the opposite sides of extension balloons 660 are not covered by the frame (though they will typically be disposed within a flexible sheath or other components of the overall catheter system). When extension balloons 660 are fully inflated, they push the adjacent flange surfaces apart so as to increase the axial separation between the associated frames. Contraction balloons 662 are disposed in a C-channel with an extension balloon, and as the size of the channel will not significantly increase, the contraction balloons will often be allowed to deflate at least somewhat with expansion of the extension balloons. Hence, offsets between adjacent similar frames (682, 682) will be urged to expand, and contraction offsets between differently oriented frames (682, 684) will be allowed to decrease. In contrast, when skeleton 680 is to be driven toward an axially contracted configuration, the contraction balloons 662 are inflated, thereby pushing the flanges of the overlapping frames axially apart to force the contraction overlap to increase and axially pull the local skeleton structure into a shorter configuration. To allow the contraction balloons 662 to expand within a particular C-channel, the expansion balloons 660 can be allowed to deflate. A number of alternative frame arrangements having opposed extension/contraction balloons can also be provided, as can be understood with reference to Provisional U.S. Application No. 62/296,409 filed Feb. 17, 2016, entitled "Local Contraction of Flexible Bodies using Balloon Expansion for Extension-Contraction Catheter Articulation and Other Uses".

Note that whichever extension/contraction skeleton configuration is selected, the axial change in length of the skeleton that is induced when a particular subset of balloons are inflated and deflated will often be local, optionally both axially local (for example, so as to change a length along a desired articulated segment without changing lengths of other axial segments) and—where the frames extend laterally and/or circumferentially—laterally local (for example, so as to impose a lateral bend by extending one lateral side of the skeleton without changing an axial length of the other lateral side of the skeleton). Note also that use of the balloons in opposition will often involve coordinated inflating and deflating of opposed balloons to provide a maximum change in length of the skeleton. There are significant advantages to this arrangement, however, in that the ability to independently control the pressure on the balloons positioned on either side of a flange (so as to constrain an axial position of that flange) allows the shape and the position or pose of the skeleton to be modulated. If both balloons are inflated evenly at with relatively low pressures (for example, at less than 10% of full inflation pressures), the flange may be urged to a middle position between the balloons, but can move resiliently with light environmental forces by compressing the gas in the balloons, mimicking a low-spring force system. If both balloons are evenly inflated but with higher pressures, the skeleton may have the same nominal or resting pose, but may then resist deformation from that nominal pose with a greater stiffness.

Referring again to FIG. 16, a C-frame skeleton 680 has two different generally C-frames or members: a C-frame 682, and a bumper C-frame 684. C-frame 682 and bumper frame 684 both have channels defined by walls 644 and flanges 648 with an axial width to accommodate two balloon assemblies. Bumper frame 684 also has a protrusion or nub that extends from one flange axially into the channel. The adjacent axial surfaces of these different frame shapes engage each other at the nub, allowing the frames to pivot relative to each other and facilitating axial bending of the overall skeleton, particularly when using helical frame members.

Referring now to FIGS. 16 and 17, a relationship between the schematic extension/retraction frame illustration of FIG. 16 and a first exemplary three dimensional skeleton geometry can be understood. To form an axisymmetric ring-frame skeleton structure 690 from the schematic modified C-frame skeleton 680 of FIG. 16, the geometry of frame members 682, 684 can be rotated about an axis 688, resulting in annular or ring frames 692, 694. These ring frames retain the wall and flange geometry described above, but now with annular wall and flanges being interlocked. The annular C-frames 682, 684 were facing different directions in schematic skeleton 680, so that outer C-frame ring 692 has an outer wall (sometimes being referred to as outer ring frame 692) and a channel that opens radially inwardly, while bumper C-frame ring 694 has a channel that is open radially outwardly and an inner wall (so that this frame is sometimes referred to as the inner ring frame 694). Ring nub 696 remains on inner ring frame 694, but could alternatively be formed on the adjacent surface of the outer ring frame (or using corresponding features on both). Note that nub 696 may add more value where the frame deforms with bending (for example, the frame deformation with articulation of the helical frame structures described below) as the deformation may involve twisting that causes differential angels of the adjacent flange faces. Hence, a non-deforming ring frame structure might optionally omit the nub in some implementations.

Referring now to FIGS. 18-20, uniform axial extension and contraction of a segment of ring-frame skeleton 690 is performed largely as described above. To push uniformly about the axis of the ring frames, three balloons are distributed evenly about the axis between the flanges (with centers separated by 120 degrees). The balloons are shown here as spheres for simplicity, and are again separated into extension balloons 660 and contraction balloons 662. In the straight extended configuration of FIG. 18, the extension balloons 660 of the segment are all fully inflated, while the contraction balloons 662 are all fully deflated. In an intermediate length configuration shown in FIG. 20, both sets of balloons 660, 662 are in an intermediate inflation configuration. In the short configuration of FIG. 21, contraction balloons 662 are all fully inflated, while extension balloons 660 are deflated. Note that the state of the balloons remains asymmetrical, so that the lengths on all lateral sides of the ring frame skeleton 690 remain consistent and the axis of the skeleton remains straight. Lateral bending or deflection of the axis of ring-frame skeleton 690 can be accomplished by differential lateral inflation of subsets of the extension and contraction balloons. More specifically, there are three balloons distributed about the axis between each pair of articulated flanges, so that the extension balloons 660 are divided into three sets. Similarly, there are three sets of contraction balloons. The balloons of each set are aligned along the same lateral orientation from the axis. Each axially aligned set of extension balloons along a particular segment can be coupled to an associated inflation fluid channel, and each axially aligned set of contraction balloons can be coupled to an associated inflation channel so that there are a total of 6 lumens or channels per segment (providing three degrees of freedom and three orientation-related stiffnesses). Other segments may have separate fluid channels to provide separate degrees of freedom, and alternative segments may have fewer than 6 fluid channels. Regardless, by selectively deflating the extension balloons of a first lateral orientation and inflating the opposed contraction balloons, a first side of ring frame skeleton 690 can be shortened. By selectively inflating the extension balloons of the other orientations and by selectively deflating the contraction balloons of those other orientations, the laterally opposed portion of ring frame skeleton 690 can be locally extended, causing the axis of the skeleton to bend. By modulating the amount of elongation and contraction distributed about the three opposed extension/contraction balloon orientations, the skeleton pose can be smoothly and continuously moved and controlled in three degrees of freedom.

While it is possible to include balloons between all the separated flanges so as to maximize available extension forces and the like, there may be advantages to foregoing kinematically redundant balloons in the system for compactness, simplicity, and cost. Toward that end, ring frame skeletons having 1-for-1 opposed extension and contraction balloons can provide the same degrees of freedom and range of motion as provided by the segments of FIGS. 16-23 (including two transverse X-Y lateral bending degrees of freedom and an axial Z degree of freedom), and can also control stiffness, optionally differentially modulating stiffness of the skeleton in different orientations in 3D space. The total degrees of freedom of such a segment may appropriately be referenced as being 4-D (X,Y,Z,&S for Stiffness), with the stiffness degree of freedom optionally having 3 orientational components (so as to provide as many as 5-D or 6-D. Regardless, the 6 fluid channels may be used to control 4 degrees of freedom of the segment.

Figure 22:
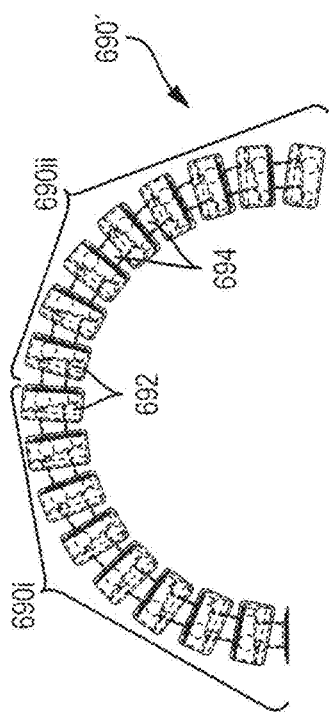
Figure 23:
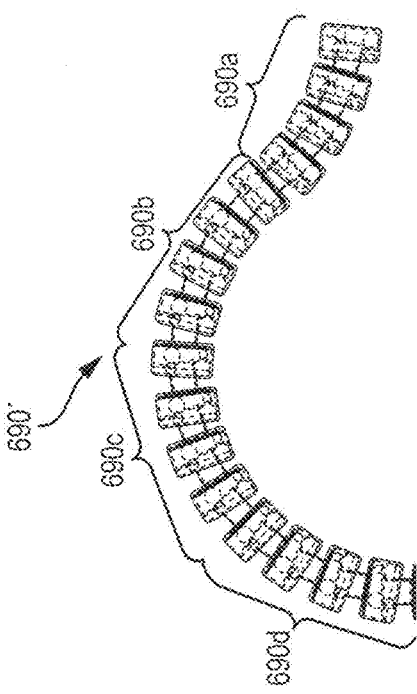

As can be understood with reference to FIGS. 22 and 23, elongate flexible bodies having ring-frame skeletons 690' with larger numbers of inner and outer ring frames 692, 694 (along with associated larger numbers of extension and retraction balloons) will often provide a greater range of motion than those having fewer ring frames. The elongation or Z axis range of motion that can be provided by balloon articulation array may be expressed as a percentage of the overall length of the structure, with larger percentage elongations providing greater ranges of motion. The local changes in axial length that a balloon array may be able to produce along a segment having ring frames 690, 690' (or more generally having the extension contraction skeleton systems described herein) may be in a range of from about 1 percent to about 45 percent, typically being from about 2½ percent to about 25 percent, more typically being from about 5 percent to about 20 percent, and in many cases being from about 7½ percent to about 17½ percent of the overall length of the skeleton. Hence, the longer axial segment length of ring frame skeleton 690' will provide a greater axial range of motion between a contracted configuration and an extended configuration, while still allowing control throughout a range of intermediate axial length states.

Figure 21:
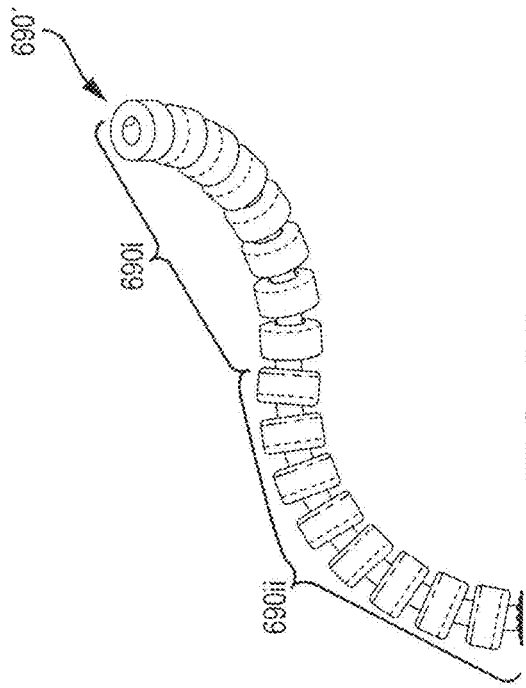
FIGS. 21-23 are illustrations of alternative elongate articulated flexible structures, and show how a plurality of independently controllable axial segments can be combined to allow control of the overall elongate structure with 6 or more degrees of freedom.

As can be understood with reference to FIG. 21, setting the balloon pressures so as to axially contract one side of a ring frame skeleton 690' (having a relatively larger number of ring frames) and axially extend the other side laterally bends or deflects the axis of the skeleton through a considerable angle (as compared to a ring frame skeleton having fewer ring frames), with each frame/frame interface typically between 1 and 15 degrees of axial bend angle, more typically being from about 2 to about 12 degrees, and often being from about 3 to about 8 degrees. A catheter or other articulated elongate flexible body having a ring frame skeleton may be bent with a radius of curvature (as measured at the axis of the body) of between 2 and 20 times an outer diameter of the skeleton, more typically being from about 2.25 to about 15 times, and most often being from about 2.4 to about 8 times. While more extension and contraction balloons 660, 662 are used to provide this range of motion, the extension and contraction balloon subsets may still each be supplied by a single common fluid supply lumen. For example, 6 fluid supply channels may each be used to inflate and deflate 16 balloons in the embodiment shown, with the balloons on a single lumen being extension balloons aligned along one lateral orientation.

Exemplary embodiments of the elongate skeleton 690' and actuation array balloon structures described herein may be functionally separated into a plurality of axial segments 690i, 690ii. Note that many or most of the skeleton components (including frame members or axial series of frame members, and the like) and actuation array components (including the substrate and/or core, some or all of the fluid channels, the balloon outer tube or sheath material, and the like), along with many of the other structures of the elongate flexible body (such as the inner and outer sheaths, electrical conductors and/or optical conduits for diagnostic, therapeutic, sensing, navigation, valve control, and other functions) may extend continuously along two or more axial segments with few or no differences between adjacent segments, and optionally without any separation in the functional capabilities between adjacent segments. For example, an articulated body having a two-segment ring frame skeleton 690' system as shown in FIG. 21 may have a continuous axial series of inner and outer ring frames 692, 694 that extends across the interface between the joints such that the two segments can be bent in coordination with a constant bend radius by directing similar inflation fluid quantities and pressures along the fluid supply channels associated with the two separate segments. As can be understood with reference to FIG. 23E, other than differing articulation states of the segments, there may optionally be few or no visible indications of where one segment ends and another begins.

Despite having many shared components (and a very simple and relatively continuous overall structure), functionally separating an elongate skeleton into segments provides tremendous flexibility and adaptability to the overall articulation system. Similar bend radii may optionally be provided with differing stiffnesses by applying appropriately differing pressures to the opposed balloons 660, 662 of two (or more) segments 690*i*, 690*ii*. Moreover, as can be understood with reference to FIG. 23D, two (or more) different desired bend radii, and/or two different lateral bend orientations and/or two different axial segments lengths can be provided by applying differing inflation fluid supply pressures to the opposed contraction/extension balloon sets of the segments. Note that the work spaces of single-segment and two-segment systems may overlap so that both types of systems may be able to place an end effector or tool at a desired position in 3D space (or even throughout a desired range of locations), but multiple-segment systems will often be able to achieve additional degrees of freedom, such as allowing the end effector or tool to be oriented in one or more rotational degrees of freedom in 6D space. As shown in FIG. 23, articulated systems having more than two segments offer still more flexibility, with this embodiment of ring frame skeleton 690' having 4 functional segments 690*a*, 690*b*, 690*c*, and 690*d*. Note that still further design alternatives may be used to increase functionality and cost/complexity of the system for a desired workspace, such as having segments of differing length (such as providing a relatively short distal segment 690*a* supported by a longer segment having the combined lengths of 690*b*, 690*c*, and 690*d*. While many of the multi-segment embodiments have been shown and described with reference to planar configurations of the segments where all the segments lie in a single plane and are either straight or in a fully bent configuration, it should also be fully understood that the plurality of segments 690*i*, 690*ii*, etc., may bend along differing planes and with differing bend radii, differing axial elongation states, and/or differing stiffness states, as can be understood with reference to FIG. 22.

Catheters and other elongate flexible articulated structures having ring frame skeletons as described above with reference to FIGS. 20-23 provide tremendous advantages in flexibility and simplicity over known articulation systems, particularly for providing large numbers of degrees of freedom and when coupled with any of the fluid supply systems described herein. Suitable ring frames may be formed of polymers (such as nylons, urethanes, PEBAX, PEEK, HDPE, UHDPE, or the like) or metals (such as aluminum, stainless steel, brass, silver, alloys, or the like), optionally using 3D printing, injection molding, laser welding, adhesive bonding, or the like. Articulation balloon substrate structures may initially be fabricated and the balloon arrays assembled with the substrates in a planar configuration as described above, with the arrays then being assembled with and/or mounted on the skeletons, optionally with the substrates being adhesively bonded to the radially inner surfaces of the inner rings and/or to the radially outer surfaces of the outer rings, and with helical or serpentine axial sections of the substrate bridging between ring frames. While extension and retraction balloons 660, 662 associated with the ring frame embodiments are shown as spherical herein, using circumferentially elongate (and optionally bent) balloons may increase an area of the balloon/skeleton interface, and thereby enhance axial contraction and extension forces. A huge variety of modifications might also be made to the general ring-frame skeletal arrangement and the associated balloon arrays. For example, rather than circumferentially separating the balloons into three lateral orientations, alternative embodiments may have four lateral orientations (+X, −X, +Y, and −Y) so that four sets of contraction balloons are mounted to the frame in opposition to four sets of extension balloons. Alternative embodiments of the ring frame structures may have apertures in the circumferential flanges between balloons so as to allow a multi-lumen shaft with intermittent balloons adhered thereon to wrap around the ring frames and then advance axially. In some embodiments, axially aligned slots may be cut though the proximal and distal flanges of, for example, an outer ring frame to accommodate a multi-lumen shaft, and the axial web of the outer ring frame between the slots may also be removed, leaving an open "C" shape when the frame is viewed axially, thereby facilitating assembly. Regardless, while ring-frame skeletons have lots of capability and flexibility and are relatively geometrically simple so that their functionality is relatively easy to understand, alternative extension/contraction articulation systems having helical skeleton members (as described below) may be even more easily fabricated and/or even more easily assembled with articulation balloon array components, particularly when using the advantageous helical multi-lumen core substrates and continuous balloon tube structures described above.

First reviewing components of an exemplary helical frame contraction/expansion articulation system, FIGS. 24A-24E illustrate actuation balloon array components and their use in a helical balloon assembly. FIGS. 24F and 24G illustrate exemplary outer and inner helical frame members. After reviewing these components, the structure and use of exemplary helical contraction/expansion articulation systems (sometimes referred to herein as helical push/pull systems) can be understood with reference to FIGS. 25 and 26.

Referring now to FIGS. 24A and 24B, an exemplary multi-lumen conduit or balloon assembly core shaft has a structure similar to that of the core described above with reference to FIGS. 14 and 15. Core 702 has a proximal end 704 and a distal end 706 with a multi-lumen body 708 extending therebetween. A plurality of lumens 710*a*, 710*b*, 710*c*, . . . extend between the proximal and distal ends. The number of lumens included in a single core 702 may vary between 3 and 30, with exemplary embodiments have 3, 7 (of which one is a central lumen), 10 (including 1 central), 13 (including 1 central), 17 (one being central), or the like. The multi-lumen core will often be round but may alternatively have an elliptical or other elongate cross-section as described above. When round, core 702 may have a diameter 712 in a range from about 0.010" to about 1", more typically being in a range from about 0.020" to about 0.250", and ideally being in a range from about 0.025" to about 0.100" for use in catheters. Each lumen will typically have a diameter 714 in a range from about 0.0005" to about 0.05", more preferably having a diameter in a range from about 0.001" to about 0.020", and ideally having a diameter in a range from about 0.0015" to about 0.010". The core shafts will typically comprise extruded polymer such as a nylon, urethane, PEBAX, PEEK, PET, other polymers identified above, or the like, and the extrusion will often provide a wall thickness surrounding each lumen of more than about 0.0015", often being about 0.003" or more. The exemplary extruded core shown has an OD of about 0.0276"", and 7 lumens of about 0.004" each, with each lumen surrounded by at least 0.004" of the extruded nylon core material.

Referring still to FIGS. 24A and 24B, the lumens of core 702 may have radial balloon/lumen ports 716*a*, 716*b*, 716*c*, . . . , with each port comprising one or more holes formed through the wall of core 702 and into an associated lumen 710*a*, 710*b*, 710*c*, . . . respectively. The ports are here shown as a group of 5 holes, but may be formed using 1 or more holes, with the holes typically being round but optionally being axially elongate and/or shaped so as to reduce pressure drop of fluid flow therethrough. In other embodiments (and particularly those having a plurality of balloons supplied with inflation fluid by a single lumen), having a significant pressure drop between the lumen and the balloon may help even the inflation state of balloons, so that a total cross section of each port may optionally be smaller than a cross-section of the lumen (and/or by limiting the ports to one or two round lumens). Typical ports may be formed using 1 to 10 holes having diameters that are between 10% of a diameter of the associated lumen and 150% of the diameter of the lumen, often being from 25% to 100%, and in many cases having diameters of between 0.001" and 0.050". Where more than one hole is included in a port they will generally be grouped together within a span that is shorter than a length of the balloons, as each port will be contained within an associated balloon. Spacing between the ports will correspond to a spacing between balloons to facilitate sealing of each balloon from the axially adjacent balloons.

Regarding which lumens open to which ports, the ports along a distal portion of the core shaft will often be formed in sets, with each set being configured to provide fluid flow to and from an associated set of balloons that will be distributed along the loops of the core (once the core is bent to a helical configuration) for a particular articulated segment of the articulated flexible body. When the number of lumens in the core is sufficient, there will often be separate sets of ports for different segments of the articulated device. The ports of each set will often form a periodic pattern along the axis of the multi-lumen core 702, so that the ports provide fluid communication into M different lumens (M being the number of different balloon orientations that are to be distributed about the articulated device axis, often being 3 or 4, i.e., lumen 710*a*, lumen 710*b*, and lumen 710*c*) and the pattern repeating N times (N often being the number of contraction balloons along each orientation of a segment). Hence, the multi-lumen core conduit can function as a substrate that supports the balloons, and that defines the balloon array locations and associated fluid supply networks described above. Separate multi-lumen cores 702 and associated balloon arrays may be provided for contraction and expansion balloons.

As one example, a port pattern might be desired that includes a 3×5 contraction balloon array for a particular segment of a catheter. This set of ports might be suitable when the segment is to have three lateral balloon orientations (M=3) and 5 contraction balloons aligned along each lateral orientation (N=5). In this example, the distal-most port 716*a* of the set may be formed through the outer surface of the core into a first lumen 710*a*, the next proximal port 716*b* to lumen 710*b*, the next port 716*c* to lumen 710*c*, so that the first 3 (M) balloons define an "a, b, c" pattern that will open into the three balloons that will eventually be on the distal-most helical loop of the set. The same pattern may be repeated 5 times (for example: a, b, c, a, b, c, a, b, c, a, b, c, a, b, c) for the 5 loops of the helical coil that will support all 15 contraction balloons of a segment to the fluid supply system such that the 5 contraction balloons along each orientation of the segment are in fluid communication with a common supply lumen. Where the segment will include expansion balloons mounted 1-to-1 in opposition to the contraction balloons, a separate multi-lumen core and associated balloon may have a similar port set; where the segment will include 2 expansion balloons mounted in opposition for each contraction balloon, two separate multi-lumen cores and may be provided, each having a similar port set.

If the same multi-lumen core supplies fluid to (and supports balloons of) another independent segment, another set of ports may be provided axially adjacent to the first pattern, with the ports of the second set being formed into an M'×N' pattern that open into different lumens of the helical coil (for example, where M'=3 and N'=5: d, e, f, d, e, f, d, e, f, d, e, f, d, e, f), and so on for any additional segments. Note that the number of circumferential balloon orientations (M) will often be the same for different segments using a single core, but may be different in some cases. When M differs between different segments of the same core, the spacing between ports (and associated balloons mounted to the core) may also change. The number of axially aligned contraction balloons may also be different for different segments of the same helical core, but will often be the same. Note also that all the balloons (and associated fluid lumens) for a particular segment that are on a particular multi-lumen core will typically be either only extension or only contraction balloons (as the extension and contraction balloon arrays are disposed in helical spaces that may be at least partially separated by the preferred helical frame structures described below). A single, simple pattern of ports may be disposed near the proximal end of core shaft 702 to interface each lumen with an associated valve plate of the manifold, the ports here being sized to minimized pressure drop and the port-port spacing corresponding to the valve plate thickness. Regardless, the exemplary core shown has distal ports formed using groups of 5 holes (each having a diameter of 0.006", centerline spacing within the group being 0.012"), with the groups being separated axially by about 0.103".

Referring now to FIGS. 24C and 24D, a continuous tube of flexible balloon wall material 718 may be formed by periodically varying a diameter of tube wall material to form a series of balloon shapes 720 separated by smaller profile sealing zones 722. Balloon tube 718 may include between about 9 and about 290 regularly spaced balloon shapes 720, with the sealing zones typically having an inner diameter that is about equal to the outer diameters of the multi-lumen helical core shafts 702 described above. In some embodiments, the inner diameters of the sealing zones may be significantly larger than the outer diameters of the associated cores when the balloon tube is formed, and the diameters of the sealing zones may be decreased (such as by heat shrinking or axially pull-forming) before or during assembly of the balloon tube and core shaft. The sealing zone may have a length of between about 0.025" and about 0.500", often being between about 0.050" and about 0.250". Decreasing the length of the sealing zone allows the length of the balloon to be increased for a given catheter size so as to provide larger balloon/frame engagement interfaces (and thus greater articulation forces), while longer sealing zones may facilitate assembly and sealing between balloons so as to avoid cross-talk between articulation channels.

Referring still to FIGS. 24C and 24D, the balloon shapes 720 of the balloon tube 718 may have diameters that are larger than the diameters of the sealing zones by between about 10% and about 200%, more typically being larger by an amount in a range from about 20% to about 120%, and often being from about 40% to about 75%. The thickness of balloon tube 718 will often vary axially with the varying local diameter of the tube, the locally large diameter portions forming the balloon shapes optionally being in a range from about 0.00008' (or about 2 microns) to about 0.005", typically being from about 0.001" and about 0.003". Balloon tube 718 may initially be formed with a constant diameter and thickness, and the diameter may be locally expanded (by blow forming, by vacuum forming, by a combination of both blow forming and vacuum forming, or by otherwise processing the tube material along the balloon shapes 720), and/or the diameter of the balloon tube may be locally decreased (by heat shrinking, by axial pull-forming, by a combination of both heat shrinking and pull forming, or by otherwise processing the tube material along the sealing zones), with the tube material often being processed so as to both locally expand the diameter along the desired balloon shapes and to locally contract the diameter along the sealing zones. Particularly advantageous techniques for forming balloon tubes may include the use of extruded polymer tubing corrugators, including the vertical small bore corrugators commercially available from Unicore, Corma, Fraenkische, and others. Suitable custom molds for such pipe corrugators may be commercially available from GlobalMed, Custom Pipe, Fraenkische, and others. Still more advanced fabrication techniques may allow blow or vacuum corrugation using a robotic shuttle corrugator and custom molds, particularly when it is desirable to change a size or spacing of balloons along a continuous tube. It should be noted that while a single continuous balloon tube is shown, a plurality of balloon tubes (each having a plurality (or in some cases, at least one) balloon shape) can be sealingly mounted onto a single core. Regardless, the sealing zones will often have a material thickness that is greater than that of the balloon shapes.

The balloon shapes 720 of the balloon tube 718 may each have a relatively simple cylindrical center section prior to assembly as shown. The tapers between the balloon center sections and the sealing zones can take any of a variety of shapes. The tapers may, for example, be roughly conical, rounded, or squared, and will preferably be relatively short so as to allow greater balloon/frame engagement for a given landing zone length. More complex embodiments may also be provided, including forming the balloon shapes with curved cylindrical center sections, optionally while corrugating or undulating the surfaces of the tapers so that the balloon tube overall remains relatively straight. The lengths of each center section is typically sufficient to define an arc-angle of from 5 to 180 degrees about the axis of the desired balloon assembly helix, more typically being from about 10 to about 50 degrees, the lengths of the center sections often being in a range from about 0.010" to about 0.400" for medical applications, more typically being from about 0.020" to about 0.150", and many times being in a range from about 0.025" to about 0.100". The exemplary balloon shapes may have an outer diameter of about 0.051" over a total balloon length (including the tapers) of about 0.059"

As can be understood with reference to FIGS. 24C, 24D, 24E, and 24E-1, balloon tube 718 may be sealingly affixed to core 702, and the core/balloon tube assembly may then be formed into a desired helical shape. The balloon tube may be sealed over the helical core using adhesive (such as any of those described above, often including UV-cured adhesives) thermal bonding, laser bonding, die bonding, and/or the like. Sealing of the balloons may also benefit from a compression structure disposed over the balloon material to help maintain tube/core engagement when the balloons are inflated. Suitable compression structures or techniques may include short sections of heat-shrink materials (such as PET) shrunk onto the sealing zones, high-strength filament windings wrapped circumferentially around the sealing zones and adhesively bonded, swaging of metallic ring structures similar to marker bands over the sealing zones, small bore crimp clamps over the sealing zones, heat-shrinking and/or pull forming the balloon tube onto the core, or the like. Any two or more of these may also be combined, for example, with the balloon tube being adhesively bonded to the core tube by injecting adhesive into the balloon tube around the sealing zone, heat shrinking the balloon tube and a surrounding PET sleeve over the sealing zone, and then swaging a metallic marker band over the sealing PET sleeve (so that the sleeve provides strain relief). Regardless, ports 716 will preferably be disposed within corresponding balloon shapes 720 and will remain open after the balloon/core assembly 730 is sealed together in the straight configuration shown in FIG. 24D. Shape setting of the balloon/core assembly from the straight configuration to the helically curved configuration of FIG. 24E can be performed by wrapping the assembly around and/or within a mandrel and heating the wrapped assembly. Helical channels may be included in the mandrel, which may also have discrete balloon receptacles or features to help ensure alignment of sets of balloons along the desired lateral balloon axes. Regardless, shape setting of the core/ balloon assembly can help set the M different lateral orientations of the balloons, so that the balloons of each set 720*i*, 720*ii*, 720*iii* are aligned (as can be understood with reference to FIGS. 24E and 24E-1).

Figure 24F:
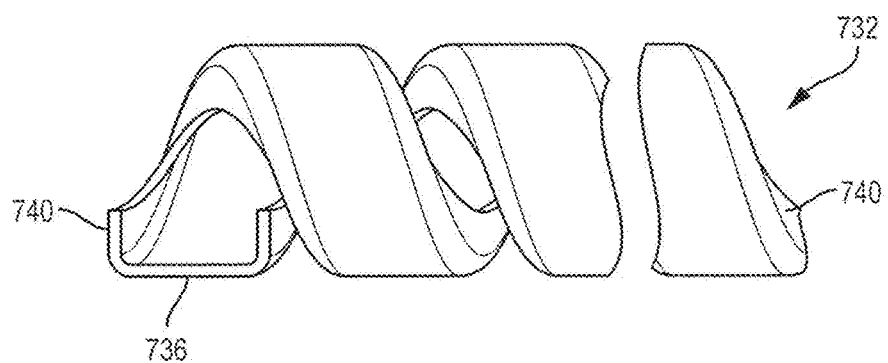
Figure 24G:
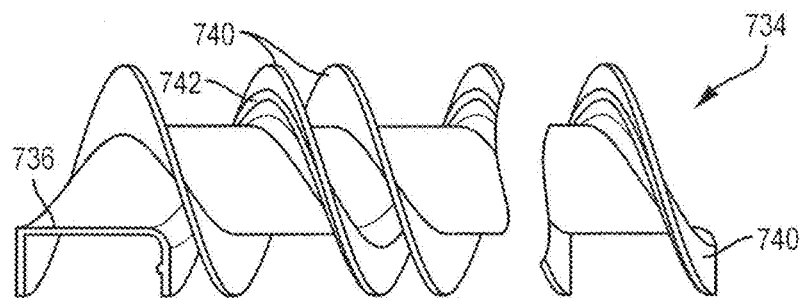

Referring now to FIGS. 24F and 24G, exemplary inner and outer helical C-channel frames, 732 and 734 respectively, can be seen. Inner helical frame 732 and outer helical frame 734 incorporate the modified C-channel frame 680 of FIG. 22*a*, but with the C-channels defined by axially continuous helical walls 736 with flanges 740 along their proximal and distal helical edges. The helical flanges are axially engaged by opposed balloons and allow inflation of the balloons to locally axially contract and/or extend the skeleton and catheter (or other articulatable body) in a manner that is analogous to the annular flanges of the ring frames described above. An optional helical nub 742 protrudes axially into the channel of inner ring frame 734 to allow the frames to pivot against each other along a flange/ flange engagement, so that the nub could instead be included on the flange of the outer frame or on both (or may comprise a separate structure that is axially sandwiched between the flanges of the two frames). Alternative embodiments may forego such a pivotal structure altogether. Optionally, the helical flanges and adjacent axial web may have channels or cuts formed therein between balloon locations so as to increase lateral flexibility of the channels, with narrower sections of the web between axially opposed channels acting as a living hinge.

Referring now to FIGS. 25A-25D, a segment of an exemplary flexible extension/contraction helical frame articulation structure 750 (sometimes referred to herein as a push/pull helical structure) incorporates the components of FIGS. 24A-24G, and provides the functionality of the annular extension/contraction frame embodiments of FIGS. 22B-22I. Push/pull structure includes a skeleton defined by inner and outer helical frames 732, 734, and also includes three balloon/core assemblies 730a, 730b, and 730c, respectively. Each balloon/core assembly includes a set of balloons at three lateral orientations, 720i, 720ii, and 720iii. Balloon/core assembly 730b extends along a helical space that is axially between a flange of the inner frame and a flange of the outer frame, and that is radially between a wall of the inner frame and a wall of the outer frame, so that the frames overlap along this balloon/core assembly. Hence, when balloons 720 of balloon/core assembly 730 inflate, they push the adjacent flanges apart and increase the overlap of the frames, inducing axial contraction of the skeleton, such that the balloons of this assembly function as contraction balloons. In contrast, balloon/core assemblies 730a and 730c are radially adjacent to only inner frame 732 (in the case of assembly 730a) or outer frame 734 (in the case of assembly 730b). Expansion of the balloons 720 of assemblies 730a, 730c pushes axially against frames so as to decrease the overlap of the frames, and acts in opposition to the inflation of balloons 720 of assembly 730b. Hence, balloons 720 of assemblies 730a, 730c function as extension balloons.

Referring now to FIGS. 25A-25C, when all the contraction balloons 720 of assembly 730b are inflated and all the extension balloons of assemblies 730a, 730c are deflated, the push/pull structure 750 is in a straight short configuration as shown in FIG. 25A. Even partial inflation of the extension balloons and even partial deflation of the contraction balloons articulates push/pull structure 750 to a straight intermediate length configuration, and full inflation of all extension balloons of assemblies 730a, 730c (along with deflation of the contraction balloons) fully axially elongates the structure. As with the ring push/pull frames, inflating contraction balloons 720ii along one lateral orientation of assembly 730b (with corresponding deflation of the extension balloons 720ii of assemblies 730a, 730b) locally decreases the axial length of the skeleton along that side, while selective deflation of contraction balloons 720i of assembly 730b (with corresponding inflation of extension balloons 720i of assemblies 730a and 730c) locally increases the length of the skeleton, resulting in the fully laterally bent configuration of FIG. 25E. Note that extension and contraction balloons along the 720iii orientation may be inflated and deflated with the extension and contraction orientation balloons of orientation 720ii so as to keep the curvature in the plane of the drawing as shown. Stiffness of the structure may be modulated uniformly or locally (with axial and/or orientation variations) as described above regarding the ring frame embodiments. Similarly, the number of extension and contraction balloons along each orientation (which will often be associated with the number of loops of assemblies 730a, 730b, etc) may be determined to provide the desired range of motion, resolution, and response. As described with reference to the push/pull ring frame embodiments, the overall articulated portion of the structure will often be separated into a plurality of independently controllable segments.

Referring now to FIG. 25F, push/pull structure 750 will often include an outer flexible sheath 752 and an inner flexible sheath 754. Sheaths 752, 754 may be sealed together at a distal seal 756 distal of the inflation lumens and balloons of assemblies 730, and one or more proximal seal (not shown) may be provided proximal of the balloons and/or near a proximal end of the catheter structure, so as to provide a sealed volume surrounding the articulation balloons. A vacuum can be applied to this sealed volume, and can be monitored to verify that no leaks are present in the balloons or inflation lumen system within a patient body.

Referring now to FIGS. 26A and 26B, an alternative push/pull structure omits one of the two extension balloon assemblies 730a, 730c, and uses a 1-to-1 extension/contraction balloon opposition arrangement as described above with reference to FIGS. 23A and 23B. Note that this embodiment retains balloon assembly 730c that is radially adjacent to outer frame 734 (so that no balloons are visible even with the sheath removed). Alternative embodiments may retain assembly 730a and forego assembly 730c (so that balloons could be seen through a clear sheath, for example).

A variety of catheter sizes and capabilities may be provided, with the number of segments often being related to the size and lumens of the cores shaft. Core shaft 702 has an outer diameter of about 0.028" and 7 lumens, with 6 peripheral lumens having an inner diameter of about 0.004" readily available for formation of associated ports and use in transmitting inflation fluid to and from balloons. A central lumen might be used, for example, in monitoring of the vacuum system to verify integrity of the system. Core shaft 702 can be used, for example, in a 14-15 Fr catheter system having two segments that are each capable of providing up to 120 degrees of bending (or alternatively more or less depending on the number of balloons ganged together on each channel), with such a system optionally capable of providing a bend radius sufficient to fit a 180 degree bend of the catheter within a space of 3 inches or less, ideally within 2½ inches or less, and in some cases within 2 inches or less. Such a system may be beneficial for structural heart therapies, for example, and particularly for mitral valve delivery, positioning, and/or implantation. Other therapies may benefit from smaller catheter profiles, and do not need the bending forces available from a 15 Fr catheter. Electrophysiology therapies such as AFib ablation from within an atrium of the heart may be good examples of therapies which would benefit from the degrees of freedom that can be provided in small structures using the systems described herein. Scaling the 15 Fr system down for a 7-8 Fr ablation catheter might make use of a directly scaled core having half the overall outer diameter and half the lumen inner diameter of core 702, as the pressure-containing stresses in the material would scale with the lumen diameters. However, there may be cost benefits to maintaining minimum lumen wall thicknesses that are above 0.002", preferably at or above 0.0025", and ideally at or above about 0.003". Toward that end, and to provide 6 contraction or extension lumens for two 3D push/pull segments along a common helical core along with a desirably small bend radius, it may be beneficial to use radially elongate core 764 having a 6 lumens that are all surrounded by at least 0.003" of material. Still further advantages may be provided by applying the smaller lumen and wall thickness dimensions of 7 Fr core to a 15 Fr catheter core size, as it results in a 12 inflation lumen core 766. A large $13^{th}$ lumen of this embodiment may help enhance flexibility of the segments, and can again be used to monitor system integrity using a vacuum system. The 12 lumens may allow, for example, a continuous push/pull structure to have 4 independently controllable 3D shape (4D shape+stiffness) segments. A 16 inflation lumen core may be provided by combining the smaller lumen and wall thickness with a radially elongate cross-section, allowing 5 independently controllable 3D segments. It should be understood that still further numbers of lumens at smaller profiles are possible using known and relatively low cost multilumen extrusion techniques.

It should be understood that still further alternative embodiments may take advantage of the beneficial components and assemblies described herein. For example, as can be understood from the disclosure above, inflation of a balloon may be resiliently opposed by a helical spring or other biasing structure so that the spring deflates the balloon and urges a flexible body back toward a pre-balloon-inflation state when the inflation fluid is released from the balloon. Rather than relying on 6 dedicated opposed expansion and contraction balloon channels for each segment (providing independent contraction and expansion along each lateral orientation) in the push/pull ring frame and push/pull helical frame embodiments described above, two or more of the channels (from the same segments or from different segments) may be grouped together to act as a common biasing structure or fluid spring. As an example, all the contraction balloons along two adjacent segments might open to a single lumen that is inflated to less than full pressure. Modulating pressure to the different sets of extension balloons may still allow the extension balloons to articulate each segment with three independent degrees of freedom, as the grouped contraction balloons could selectively be overpowered by the extension balloons (like the coil springs) or may be allowed to deflate the extension balloons. In some embodiments, rather than relying on partial pressure of extension or contraction balloons, an elastomeric material may be mounted over the core of some or all of the extension or contraction balloons of a segment so as to passively oppose a set of the balloons.

Figure 27:
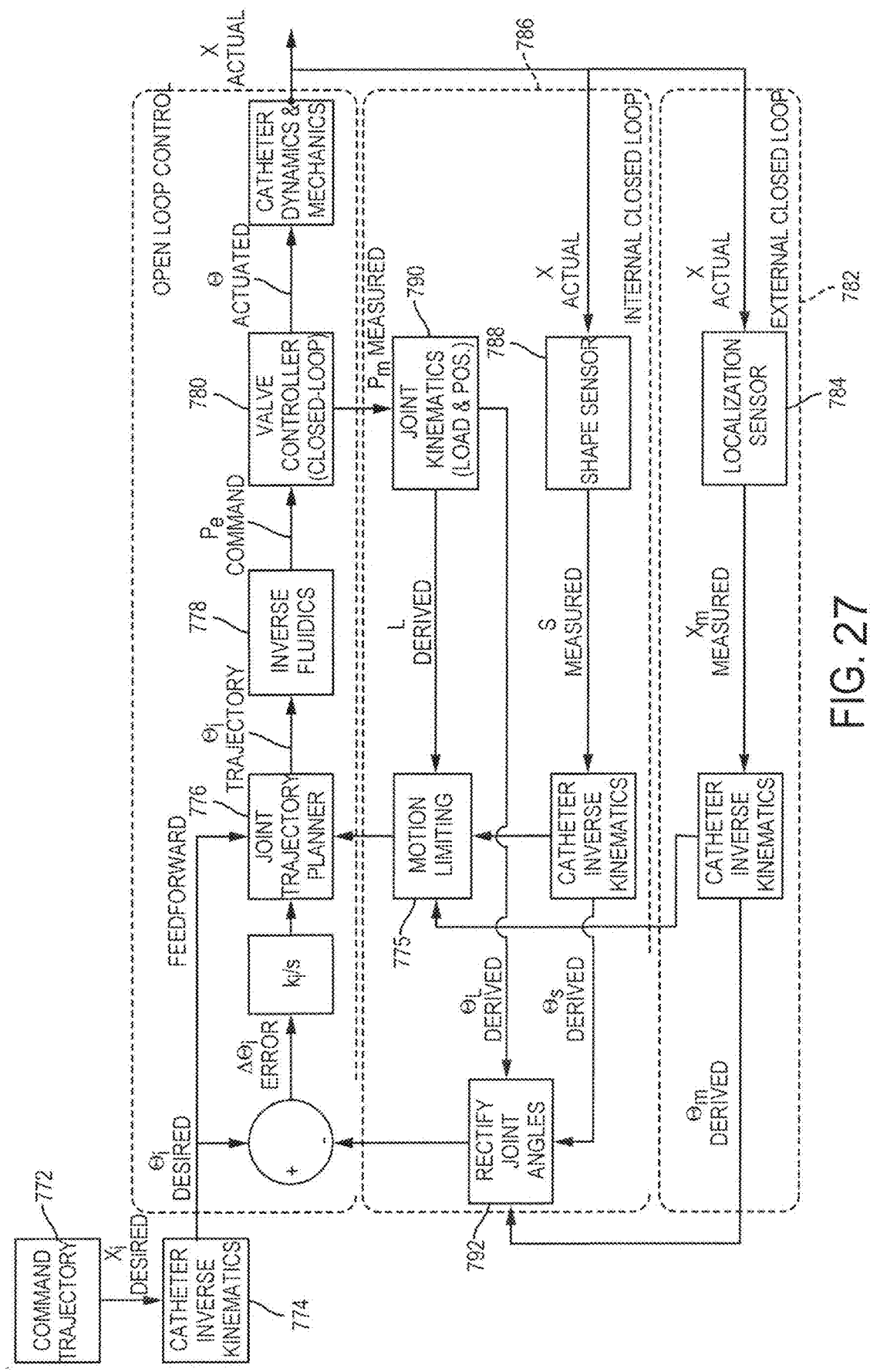
FIG. 27 schematically illustrates control system logic for using the fluid drive systems described herein to articulate catheters and other elongate flexible structures per input provided by a system user.

Referring now to FIG. 27, an articulation controller 770 for directing inflation fluid to and from the actuation balloons of the systems will typically have hardware and/or software configured and programmed to generally seek to cause the articulable structure to assume a new actual position or state $X_{actual}$ in response to a commanded trajectory 772 input by a system user. Many of the articulated flexible structures described herein may be included in robotic systems that can be analyzed and controlled using techniques associated with continuum robots, and the articulated structures will often be under-constrained with more joints then can be directly controlled by the system using standard controller. These excess or redundant degrees of freedom are often managed and made to cooperate using an internal compliance that directs the joints to be at a similar angle relative to the next joint within the segment. These equal joint angles may help lead the system toward a lowest potential energy state for the system. The processor of the system will typically have software modules to determine the next desired position or state of the articulatable structure $X_{iDesired}$, and will apply inverse catheter kinematics 774 to determine the next desired joint state $\Theta_{iDesired}$. A difference between an actual joint state and the next desired joint state is determined to define a joint error, and the desired joint state can be fedforward to a joint trajectory planner 776 along with the joint error to define a joint error trajectory. This joint trajectory can be used in an inverse fluidic calculation 778 to determine command signals that can be fed into a closed-loop valve controller 780 so as to provide an actuated joint state. In some embodiments, closed loop control of the valves may depend on pressure sensing, and may be used to control to specific pressures as determined by valve inverse kinematics. The catheter dynamics and mechanics reaction to the actuated joint state (with the associated environment interactions with the catheter such as tissue forces and the like) result in a new actual position or state $X_{actual}$ of the articulated catheter system.

Feedback on the actual position or state of the articulated system to the controller may be omitted in some embodiments, but other embodiments may benefit from such feedback to provide more precise movements and better correlation (from the system user's perspective) between the command inputs and the actual changes in state. Toward that end, the controller may optionally use one or more closed loop feedback pathways. In some embodiments, a feedback system that is partially or fully external to the articulated structure 782 may sense the actual position or state of the catheter or other articulated structure using a localization sensor 784, such as an electromagnetic navigation system, an ultrasound navigation system, image processing coupled to 3D imaging (such as biplanor fluoroscopy, magnetic resonance imaging, computed tomography, ultrasonography, stereoscopic cameras, or the like; where the imaging modality may optionally also be used to produce images presented to the system user for image guided articulation). In many embodiments, the feedback will be provided using signals obtained from the articulated system itself under an internal closed loop feedback system 786. To obtain a measured shape or state of the articulated structure, a variety of known sensor technologies may be employed as an articulated structure shape sensor 788, including optical fiber shape sensors (such as those using fiber Bragg gratings), electrical shape sensors (such as those which use elastically deformable circuit components), or the like. The measured and/or sensed signals may be processed using inverse kinematics to derive associated measure and/or sensed joint states. Furthermore, balloon array pressure signals will often be available from the pressure sensors of the system, along with information correlating the pressures with the joint or shape state of the articulated system. The history of inflation fluid directed to and exhausted from the articulation balloons may also be used to help determine an estimated inflation fluid quantity present in each balloon (or set of balloons on a common inflation lumen). Where balloons are mounted in opposition or in parallel, the pressure and inflation fluid quantity of these related balloons on separate channels may also be available. Some or all of this pressure information may be processed using a joint kinematics processor 790 to determine a pressure-derived joint position or state (including a derived position of the pressure-articulated joints making up the flexible structure kinematic chain $\Theta_{LDevived}$). The pressure information, preferably along with internal localization information and/or external localization information, may also be used by the joint kinematic processor 790 to derive the loads on the joints, for determining of motion limits 775 as used by the joint trajectory planner 776, and the like. Where more than one is available, the external localization-based feedback joint state, the internal shape-sensor based joint state, and the pressure-derived joint state may be rectified 792 and the rectified (or otherwise any available) joint state compared to the desired joint state to determine the joint error signal.

Figure 28:
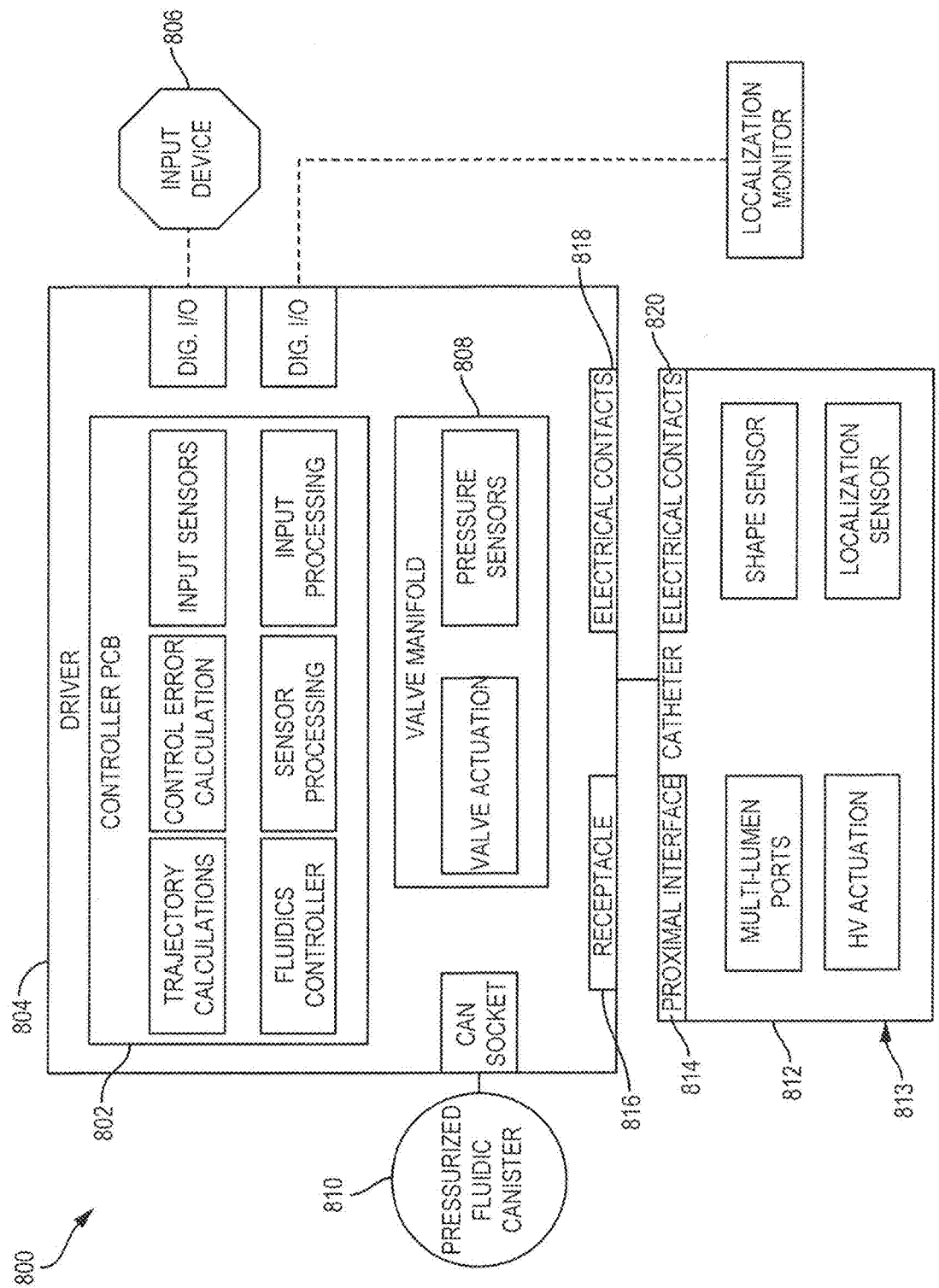
FIG. 28 schematically illustrates a data acquisition and processing system for use within the systems and methods described herein.

Referring now to FIG. 28, an exemplary data processing structure 800 for controlling the shape of a catheter or other articulated elongate flexible bodies described herein can be understood. Much of the data processing occurs on a controller board 802 of reusable driver 804, with the driver optionally comprising a hand-held capital equipment unit. The input device 806 may optionally include a separate workstation with wired or wireless data telemetry (so as to allow, for example, an interventional cardiologist or the like to perform a portion of the procedure while separated from the radiation field of a fluoroscopy system), or input device 806 may be a user interface integrated into the hand-held driver, or both. Preferably, the valve manifold 808 will comprise one of the modular plate manifold structures described herein, and will be contained within the hand-held driver unit 804. Canister 810 may be affixed to the driver (directly or by coupling of the catheter to the driver), and will often be included within a hand-held proximal assembly of deployment system that includes the driver, the proximal interface of the catheter, and other proximal components of the catheter (such as the heart valve actuation or deployment device 813, or the like) during use. Similarly, a battery of the system (not shown) may be integrated into the driver 804, may be mounted to the proximal interface of the catheter, or both.

A catheter 812 or other elongate flexible body for use with driver 804 will generally have a proximal interface 814 that mates with a receptacle 816 of the driver. As can be understood with reference to the descriptions above, the mating of the proximal interface with the receptacle will often provide sealed fluid communication between a balloon array of the catheter and the valves of the manifold assembly. Coupling of the proximal interface with the receptacle may also result in coupling of electrical contacts of the driver 818 with electrical contacts of the catheter 820, thereby facilitate access to internal shape sensor data, external localization data (which may employ a powered fiducial on the catheter and an external electromagnetic sensor system, or the like). Still further communications between the catheter and the driver may also be facilitated, including transmission of catheter identification data (which may include a catheter type for configuration of the controller, a unique catheter identifier so as to help inhibit undesirable and potentially deleterious re-use of the catheter, and the like). As an alternative to (or in addition to) electrical communication of this data, catheter 812 may have an RFID, bar code, or other machine-readable tag on or near proximal interface 814, and driver 804 may include a corresponding reader one or near receptacle 816.

Figure 29A:
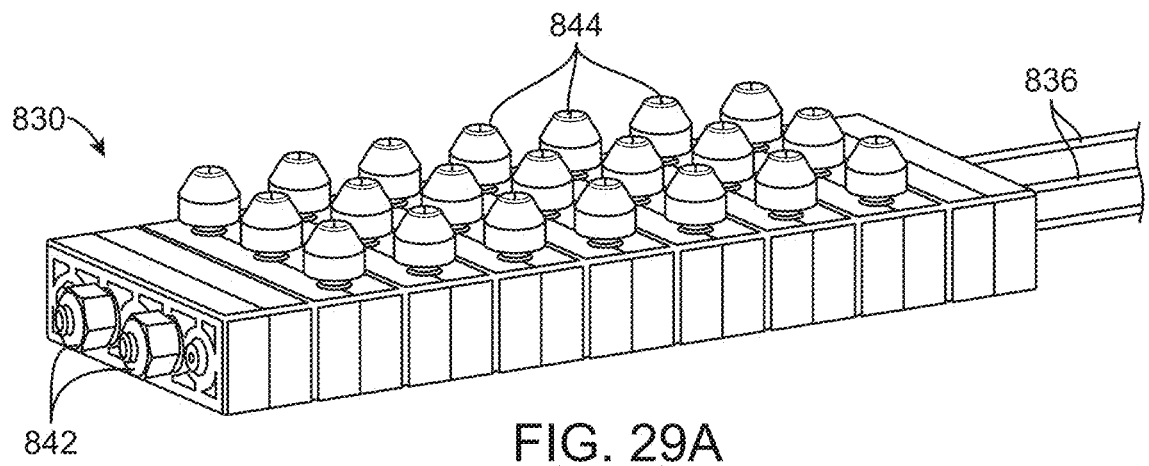
FIGS. 29A-30 illustrate an alternative interface for coupling a modular fluid manifold to a plurality of multi-lumen shafts so as to provide control over articulation of a catheter along a plurality of segments, each having a plurality of degrees of freedom, along with portions of some of the plate modules of the manifold, with the plate modules here having a receptacle member that helps couple the layers of the plates to posts of the interface.
Figure 29B:
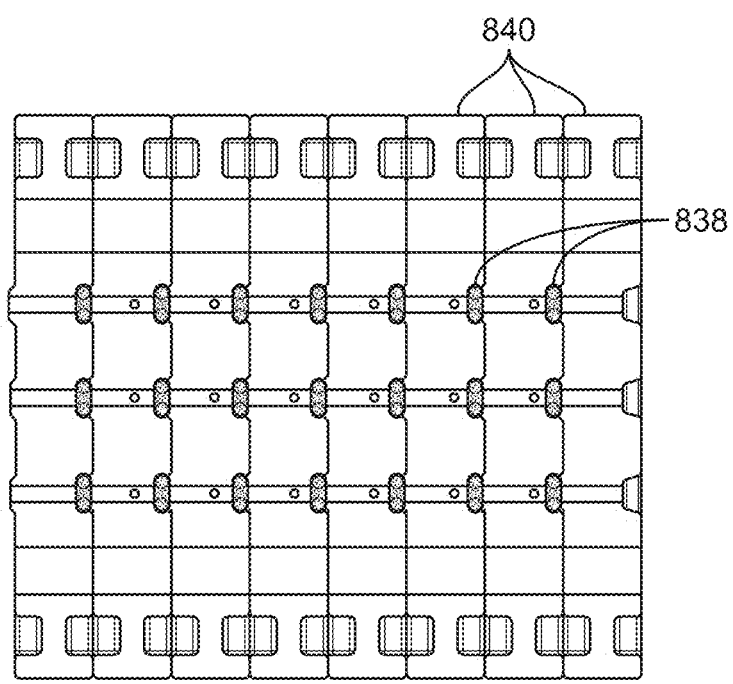
Figure 29C:
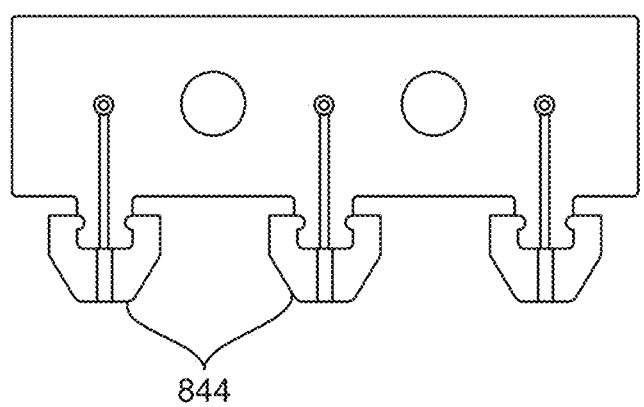
Figure 30:
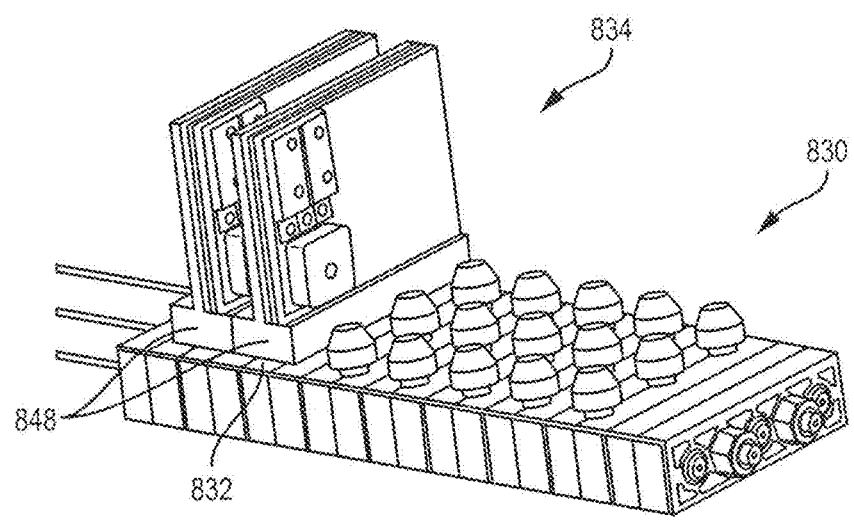

Referring now to FIGS. 29A-30, an alternative proximal interface 830 of the catheter can be understood, along with how it can be mated to an alternative receptacle 832 of an alternative modular manifold 834. Proximal interface 830 provides sealed communication between axially separated ports of up to three multi-lumen shafts 836, with the ports of the multi-lumen shafts being sealed by axially compressing O-rings 838 or other deformable sealing bodies interleaved between more rigid interface members 840. Threaded compression members 842 maintain axial sealing compression between a proximal-most interface member and a distal-most interface member. Posts 844 of interface members 840 extend laterally and parallel to each other. Each interface member 840 includes a post 844 for each multi-lumen shaft, and the number of interface members included in proximal interface 830 is the same as the number of independently used lumens in each multi-lumen shaft, so that the posts form an array with the total number of posts being equal to the total number of independent multi-lumen channels in the articulated structure. Lumens extend radially from the ports of the multi-lumen shaft, through the posts 844, and to an interface port surrounded by a cap of deformable seal material.

Referring to FIG. 30, receptacle 832 of manifold assembly 834 has a series of indentations that correspond with posts 844 of proximal interface 830. The indentations have surfaces that correspond to the posts and seal to the deformable caps with the interface ports each in sealed fluid communication with an associated channel of an associated plate module. In this embodiment, the receptacle surfaces of each plate modules is on a receptacle member 848. The receptacle members support plate layers with channels formed between the layers, with MEMS valves and pressure sensors mounted to the plates as described above. Here, however, the plates of adjacent plate modules may not be in direct plate-plate contact, so that the supply and exhaust flows may extend axially through the receptacle members, through the proximal interface, or through another structure of the manifold assembly.

Referring now to FIGS. 31A-31D, an alternative balloon-articulated structure 850 having a single multi-lumen core may be particularly well suited for smaller profile applications, such as for microcatheters having sizes down to 2 or 3 Fr, guidewires, or the like. Articulated structure 850 generally has a proximal end 852 and a distal end 854 and may define an axis therebetween. A frame 856 of the structure is shown by itself in FIG. 31C and is generally tubular, having a series of loops 858 interconnected by axial struts 860. Two struts may be provided between each pair of adjacent loops, with those two struts being circumferentially offset by about 180 degrees; axially adjacent struts between nearby loop pairs may be offset by about 90 degrees, facilitating lateral bending of the frame in orthogonal lateral bending orientations. As will be understood from many of the prior frame structures described herein, apposed surface region pairs between loops 858 will move closer together and/or farther apart with lateral bending of frame 850, so that a balloon can be used to control the offsets between these regions and thereby the bending state of the frame.

Figure 31A:
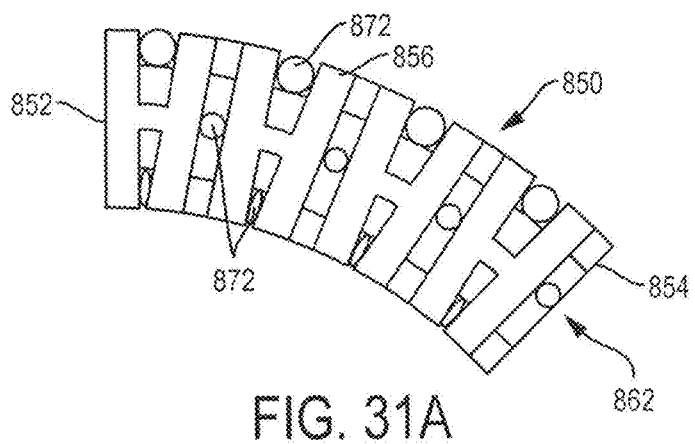
FIGS. 31A-31D illustrate an alternative articulatable structure having a single multi-lumen core with balloons extending eccentrically from the core, along with details of the structure's components and assembly.
Figure 31B:
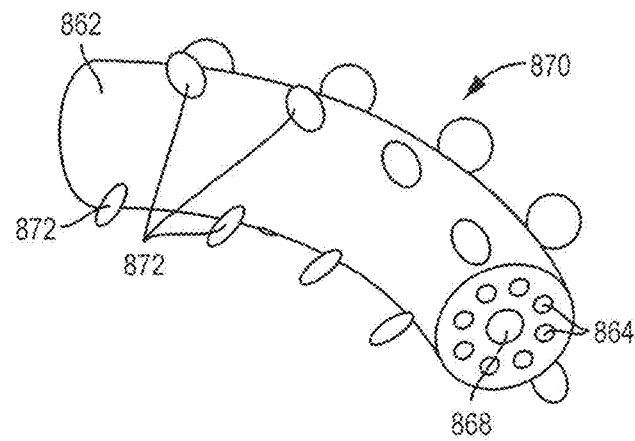
Figure 31C:
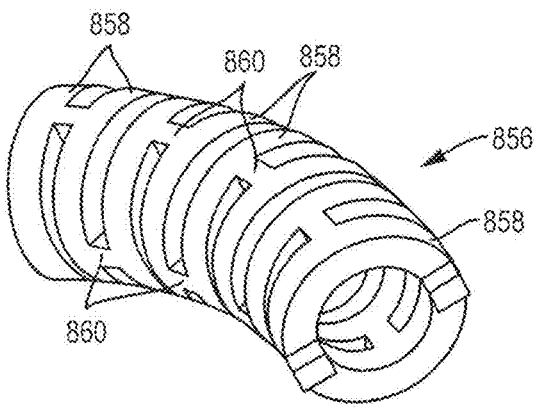
Figure 31D:
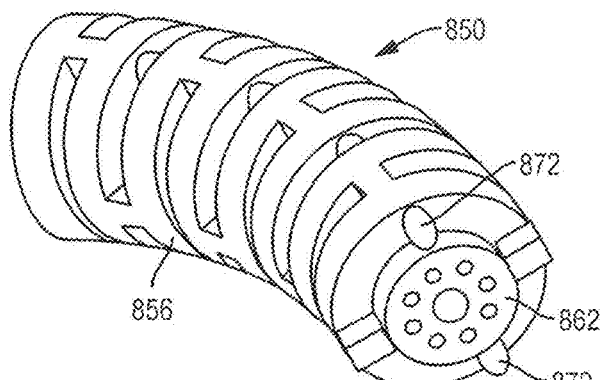

A multi-lumen core 862 is shown by itself in FIG. 31B, and extends axially within the lumen of frame 856 when used (as shown in FIG. 31D). Core 862 includes a plurality of peripheral lumens 864 surrounding a central lumen 868. Central lumen 868 may be left open as a working channel of articulated structure 850, to allow the articulated structure to be advanced over a guidewire, for advancing a guidewire or tool through the articulated structure, or the like. An array 870 of eccentric balloons 872 is distributed axially and circumferentially about the multi-lumen core, with the array again taking the form of an M×N array, with M subsets of balloons being distributed circumferentially, each of the M subsets being aligned along a lateral bending orientation (M here being 4, with alternative embodiments having 1, 2, 3, or other numbers of circumferential subsets as described above). Each of the M subsets includes N balloons, with N typically being from 1 to 20. The N balloons of each subset may be in fluid communication with an associated peripheral lumen 864 so that they can be inflated as a group. Eccentric balloons 872 may optionally be formed by drilling ports between selected peripheral lumens 864 to the outer surface of the body of the core, and by affixing a tube of balloon wall material affixed over the drilled body of multi-lumen core 862, with the inner surface of the balloon tube being sealingly affixed to an outer surface of the multi-lumen body of the core. Alternatively, eccentric balloons may be integral with the multi-lumen core structure, for example, with the balloons being formed by locally heating an appropriate region of the multi-lumen core and pressurizing an underlying lumen of the core to locally blow the material of the multi-lumen body of the core radially outwardly to form the balloons. Regardless, the balloons extend laterally from the body of the multi-lumen core, with the balloons optionally comprising compliant balloons, semi-compliant balloons, or non-compliant balloons. The shape of the inflated balloons may be roughly spherical, hemispherical, kidney shaped (curving circumferentially about the axis of the core), cylindrical (typically with a length:diameter aspect ratio of less than 3:1, with the length extending radially or circumferentially), or some combination of two or more of these.

When multi-lumen core 862 is assembled with frame 856 (as in FIGS. 31A, 31C, and 31D), the body of the multi-lumen core is received in the lumen of the frame and balloons 872 are disposed between the apposed surfaces of loops 858. By selectively inflating one subset of balloons 872 aligned along one of the lateral bending orientations, and by selectively deflating the opposed subset of balloons (offset from the inflated balloons by about 180 degrees), the axis of articulatable structure 850 can be curved. Controlling inflation pressures of the opposed balloon subsets may vary both a curvature and a stiffness of articulatable structure 850, with increasing opposed inflation pressures increasing stiffness and decreasing opposed inflation pressures decreasing stiffness. Varying inflation of the laterally offset balloon sets (at 90 and 270 degrees about the axis, for example) may similarly variably curve the structure in the orthogonal bending orientation and control stiffness in that direction. The profile of the single-core assembly may be quite small, with an exemplary embodiment having an outer diameter of frame 856 at about 1.4 mm, an outer diameter of the body of multi-lumen core 862 of about 0.82 mm, and an inner diameter of the peripheral lumens 864 of about 0.10 mm. The multi-lumen core body and balloons may comprise polymers, such as any of the extrusion or balloons materials described above, and the frame may comprise a polymer or metal structure, the frame optionally being formed by molding, cutting lateral incisions in a tube of material, 3D printing, or the like. Note that the exemplary multi-lumen core structure includes 8 peripheral lumens while the illustrated segment makes use of 4 lumens to articulate the segment in two degrees of freedom; a second segment may be axially coupled with the shown segment to provide additional degrees of freedom, and more lumens may be provided when still further segments are to be included.

Figure 32A:
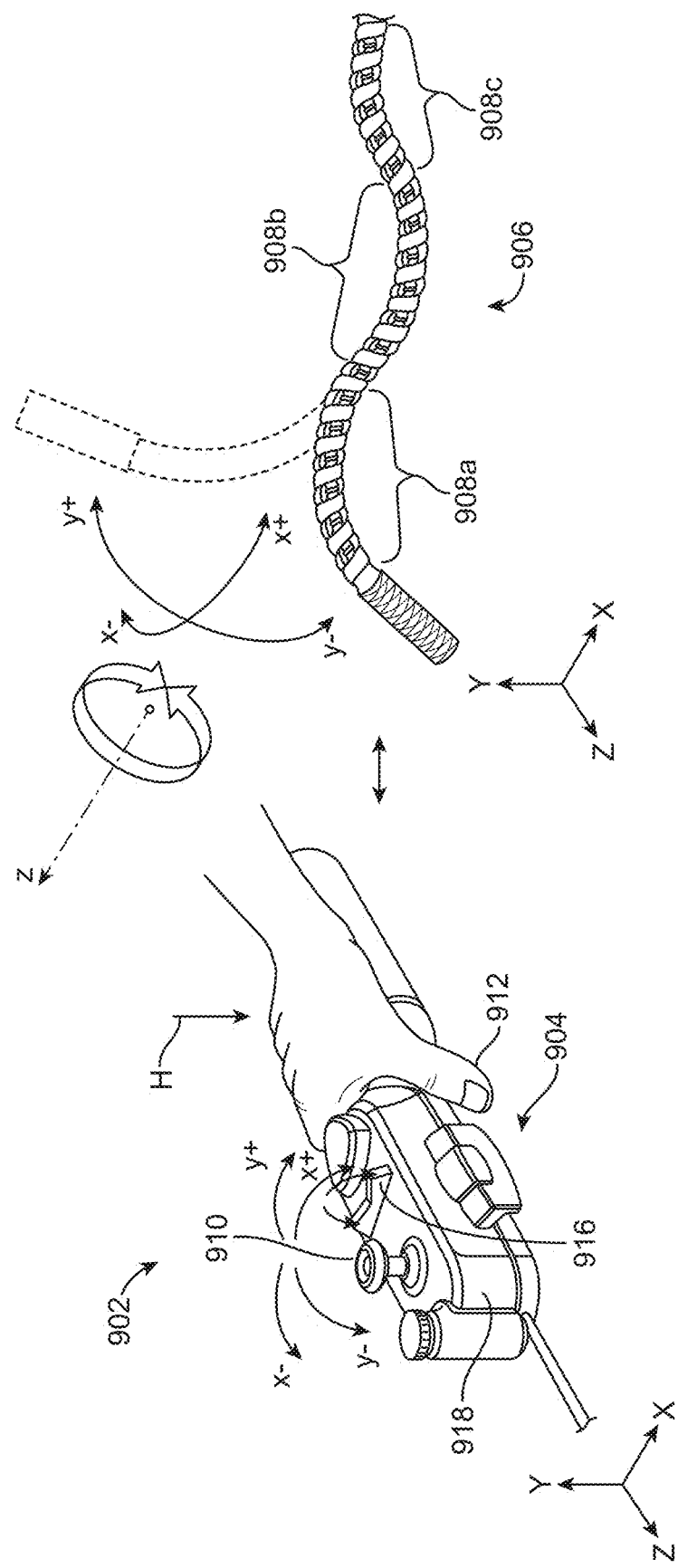
FIG. 32A illustrates a hand-held housing having a joystick and how a movement command can be input by the hand holding the housing by manipulating the joystick with a thumb of hand.

Referring now to FIG. 32A, an articulation system 902 includes a housing input device 904 and an articulated catheter 906 having 3 independently articulatable segments 908a, 908b, 908c. Each segment may have 3 articulated degrees of freedom, including lateral bending in X and Y orientations, and axial elongation in a Z orientation. To control lateral bending of, for example, a distal segment 908a, housing input device 904 may, for example, have an X-Y joystick 910 that is configured to be manipulated by a thumb 912 of a hand H that is holding the housing input device. Ease of use of the input device may be enhanced by alignment between the X-Y joystick 910 and the X-Y articulation of the catheter 906 that is induced by movement of the joystick. The preferred alignment is between the movement command as entered into the input device and the resulting automated movement of segment 908a, 908b, and/or 908c, per the perception of the surgeon, so that the relationship is comfortable or intuitive. The surgeon may primarily perceive movement at the distal end of the catheter from an image obtained by way of fluoroscopy (or some other remote imaging modality) and displayed to the surgeon on a screen or other display device. The desired alignment is typically not directly associated with a true alignment between the catheter tip and the input device, so that the actual orientation of the catheter tip and input device may be at any relative angle. The perception of orientation is related to the relative orientation of the monitoring or imaging field (aka. monitor and camera position/angle) and to the display of the catheter tip image to the surgeon. Suitable alignment may be achieved using a rotational alignment input 916 to electronically rotate the X-Y lateral articulation axes of distal segment 908a, intermediate segment 908b, and/or proximal segment 908c about the Z or elongate axis of the distal segment. Segments 908a, 908b and 908c may be rotationally affixed together about the Z axis, so that providing alignment with any may achieve alignment with all three. Regardless, one or more additional joysticks or other input structures could be provided to provide control over the other degrees of freedom of articulated catheter 906. Alternatively, input for at least some articulation degrees of freedom may be provided by moving a housing 918 of housing input device 904 with hand H, significantly simplifying the user interface and allowing a single hand of the user to provide intuitive input commands for 3, 4, 5, 6, 7, or even 8 or more articulated degrees of freedom of catheter 906, the articulated degrees of freedom sometimes called the degrees of freedom in joint space.

Figure 32B:
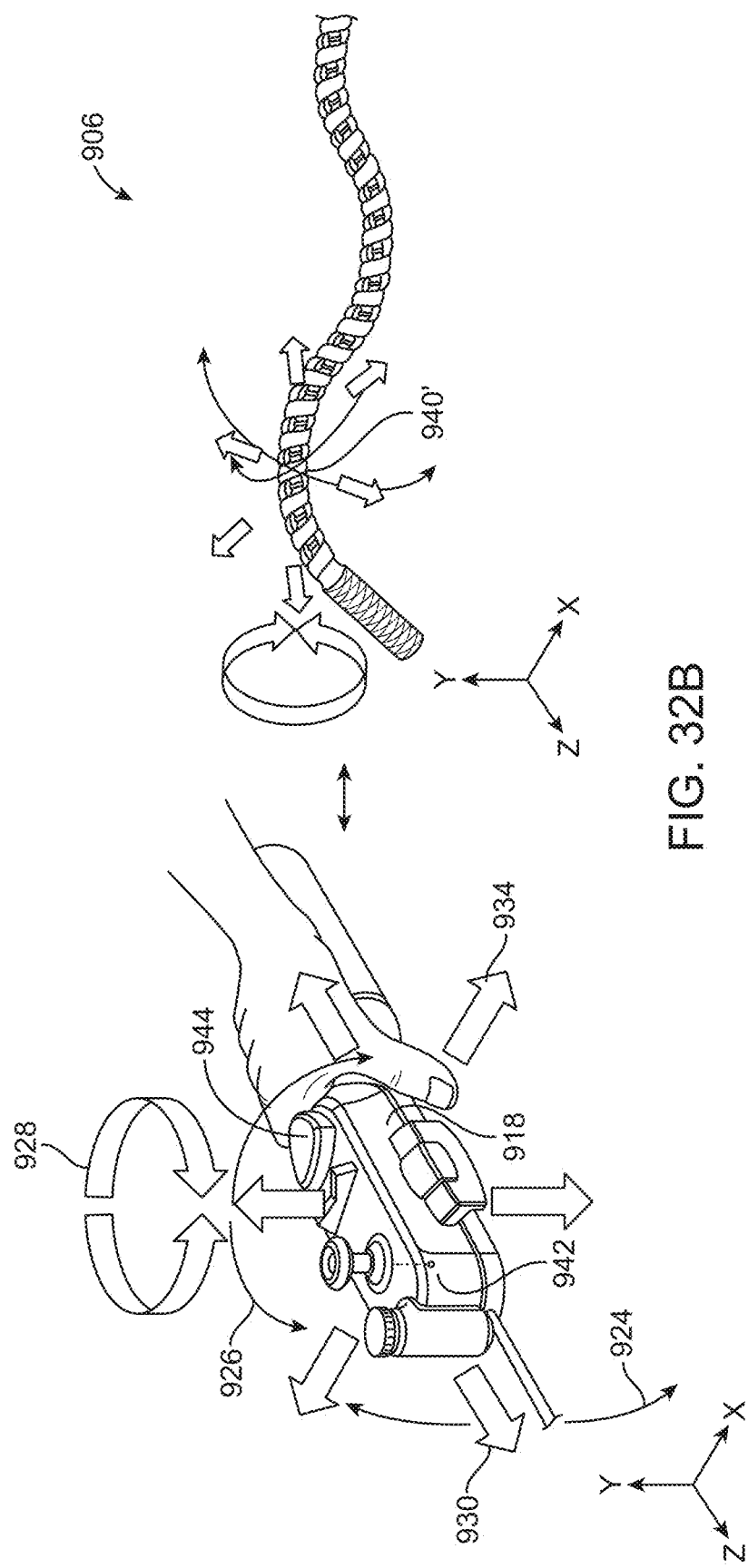
FIG. 32B schematically illustrates an optional correlation between degrees of freedom of the input housing and articulated degrees of freedom of the catheter.

Referring now to FIG. 32B, a mapping of the movement of housing 918 may effectively map input command movements of housing 918 to displayed movements of catheter 906, with movements of the housing in a single input degree of freedom often inducing combined movements of articulation degrees of freedom at a desired coupling location 940', so that the articulated catheter appears to move with output movements that correspond to those of the housing. For example, yaw 928 of housing 918 about input center 942 may result in a combination of elongation and lateral deflections of both the intermediate and proximal segment so as to more precisely mimic yaw at coupling location 940 than could be generated by articulation within any single segment. Similar mappings of pitch and yaw movements of the housing about input center 942 to pitch and yaw of the catheter about coupling location 940, and of the three translation degrees of freedom to translation degrees of freedom of the coupling location, can also be provided as shown. These mappings may help the user to maintain accurate control over the catheter by providing output movements that the user perceives as corresponding intuitively with input command movements.

In many embodiments, movement of housing 918 will only induce movement of catheter 906 while a clutch input 944 is being squeezed by the hand; releasing of the clutch may halt movement of catheter 906. Optionally, the input/output correlation between the housing and the catheter may provide a velocity controller so that movement of housing 918 while clutch input 944 is depressed may provide a velocity command, initiating movement of catheter 906 in the orientation of the housing movement and with a velocity proportional to the scale of the housing movement. Alternatively, an input/output correlation between the housing and the catheter may provide a position controller so that movement of housing 918 while clutch input 944 is depressed may provide a position command, initiating movement of catheter 906 in the orientation of the housing movement and for a distance proportional to the scale of the housing movement. In many embodiments, the coupling center on the catheter may be adjacent the proximal or distal end of the deliverable therapeutic or diagnostic tool, such as a prosthetic valve. This might be at a distal tip of the distal segment, and may make the user feel like they are holding a pair of pliers with something in the pliers, that something being the tool (such as the prosthetic valve).

Figure 33:
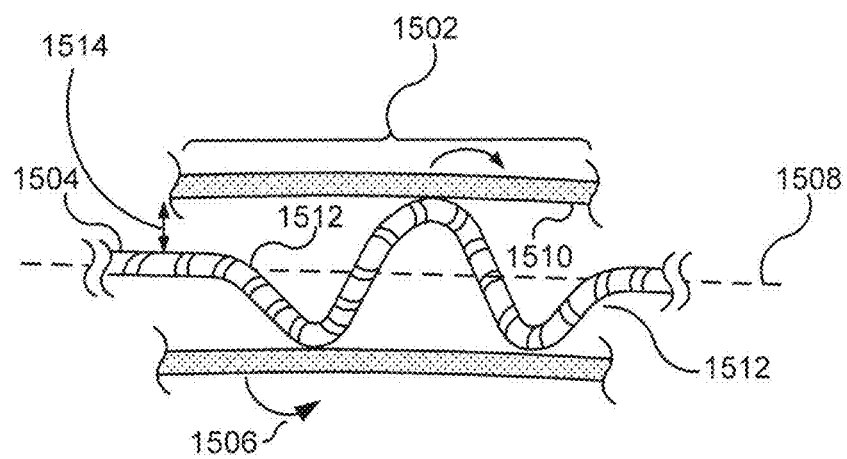
FIG. 33 schematically illustrates a helical anchor configuration of an articulated portion of a catheter, in which circumferential bending of the catheter induces atraumatic catheter/lumen wall engagement.

Referring now to FIG. 33, an exemplary anchor segment 1502 of a catheter 1504 is shown with the segment articulated toward a helical anchor configuration. In the anchor configuration, segment 1502 forms a series of sequential circumferential bends such that segment 1502 is biased to form a generally helical configuration coiling about an axis 1508 of the body lumen 1510. Segment 1502 may be articulated so that if it were unconstrained it would have a helical outer diameter slightly larger than the inner diameter of the of body lumen 1510, thereby biasing the segment to engage the surrounding lumen with sufficient force to inhibit relative movement. Additional centering or orientation bends 1512 near the proximal and/or distal ends of segment 1502 can help limit engagement between the catheter proximally and/or distally of the anchored segment and the surrounding tissue surfaces. For helical anchor configurations, suitable orientation bends may both angle radially inward away from the lumen wall, and then axially so that the catheter body beyond the anchor extends along the axis 1508 with a desired separation 1514 between the catheter body and the surrounding lumen wall. Alternative anchor embodiments may have a serpentine configuration, optionally extending along a plane (such as with a sinusoidal or opposed arc-segment configuration), with suitable orientation bends orienting the catheter body extending distally of the anchor along the centerline of the curved shape. Helical anchor configurations may have one or more full loops of bends, while serpentine configurations will often have more than one full cycle of periodic bends.

As described above, segment 1502 will typically be articulated by inflation of a subset of balloons of a balloon array. The number of balloon channels along used to articulate segment 1502 may be limited (optionally to 4, 3, or even 2) by coupling selected balloons together using a suitable multi-lumen shaft port pattern. To limit trauma to the lumen wall, it may be advantageous to inflate the balloons using an inflation system that, at least in-part, contains gas, thereby allowing the segment to conform to the environmental forces imposed by the surrounding tissue. Such compliant anchoring systems may be offset axially from positioning balloon array systems that at least partially are inflated with liquid, and which may provide a less compliant (and more positionally precise) articulation for example, to improve alignment of therapeutic or diagnostic tools with a target tissue or the like. Different gas/liquid inflation (and related differing compliance properties) may be provided by including a plurality of plenums (such as one with gas and another with liquid) or other differentiated inflation fluid sources, or simply by having different procedures for the different channels, such as by pre-loading N20 or another gas in a first balloon channel and pre-loading saline or another liquid in a second balloon channel. Still further embodiments may, for example, have a single overall plenum with penum pressure maintained by controlled addition of N20 or another gas to a space on one side of a diaphragm. This gas can maintain a pressure of both the gas in the plenum and of an inflation liquid on the other side of the diaphragm. By providing separate gas and liquid header supply valves between an inflation header and the two sides of the diaphragm, balloon channels may be selectably inflated with pressure-controlled gas or liquid as desired, allowing the compliance characteristics of the different balloon channels to be selected and/or controlled.

Figure 34:
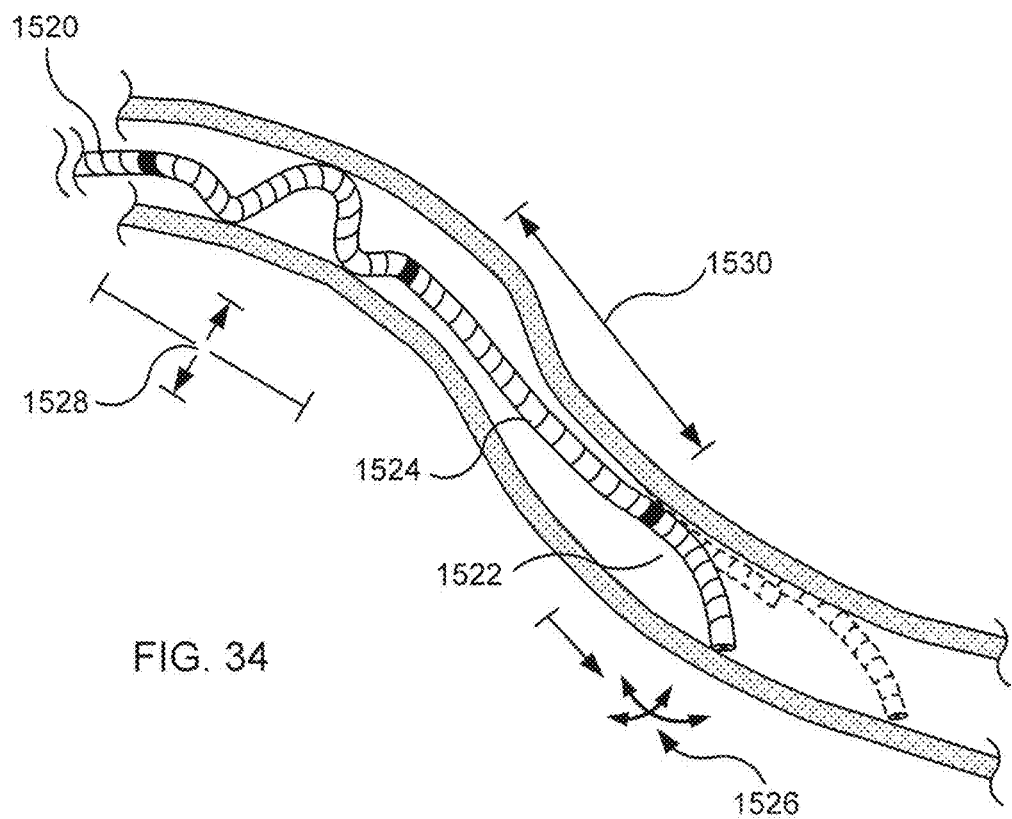
FIG. 34 schematically illustrates the use of proximal and distal articulated segments as anchor segments, shows how an axial elongation of an intermediate segment can be used to help axially advance a catheter within a body lumen.

Referring now to FIG. 34, an alternative three-segment articulated catheter 1520 includes a proximal anchor segment 1502 similar to that described above, a distal segment 1522, and an intermediate segment 1524 extending axially between the proximal and distal segments. Distal segment 1522 may be laterally deflectable along opposed steering orientations 1526, and may also be driven to a lateral bend orientation that is sufficiently bent to engage opposed tissue surface regions of a surrounding lumen wall, thereby axially anchoring the distal segment in a manner similar to deployment of a J-wire or pigtail guidewire or catheter. In contrast, proximal catheter 1528 can be driven to a helical anchor configuration having a helical diameter and length sufficient to provide a stable base relative to surrounding tissues for accurate articulated movement of the more distal segments in three, four, five, or six degrees of freedom. Intermediate segment 1524 can be driven to elongate and/or shorten axially between the anchors. By anchoring the proximal anchor 1520 with the intermediate segment 1524 in a shortened configuration, then elongating the intermediate segment, and then anchoring distal segment 1522, the distal end can be advanced along the body lumen. By then releasing the proximal anchor, shortening the intermediate segment, and re-anchoring the proximal anchor, the distal articulated portion of the catheter can help the entire length of the catheter move distally along the body lumen as shown.

Figure 35C:
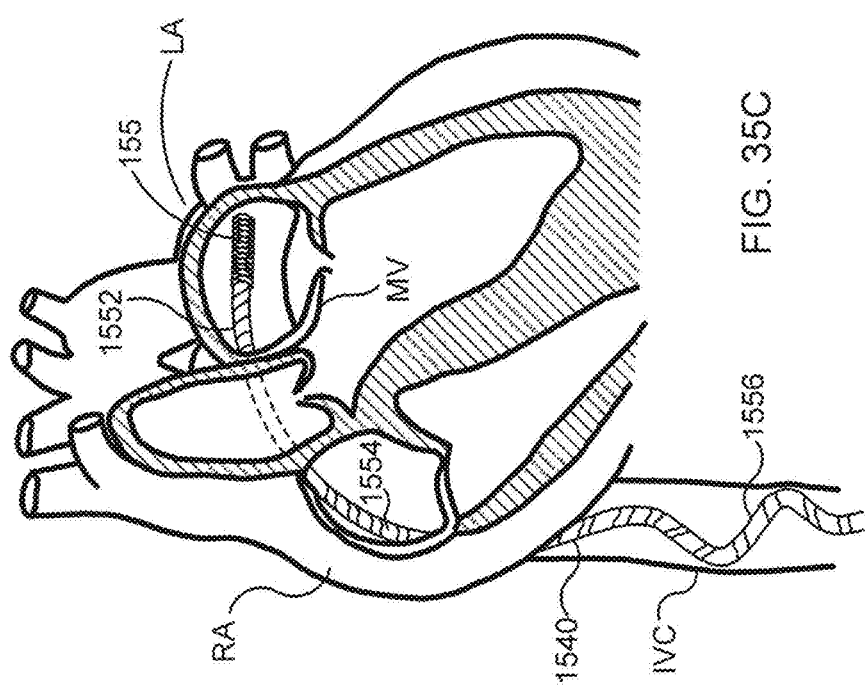

Referring now to FIGS. 35A-35C, advancement of a simplified valve deployment system 1540 in a heart 1542 of a patient body is schematically shown. In this schematic illustration of deployment system 1540, a prosthetic valve is supported at the distal end of an articulated catheter. While not shown for simplicity, a tapered dilation tip and/or a retractable sheath may be provided to facilitate advancement. A guidewire 1544 may be advanced to the heart via the inferior vena cava IVC using known techniques, and access to the mitral valve MV may be provided by crossing the right atrium RA and traversing the septum separating the right atrium from the left atrium LA using standard transseptal access components. Optionally, steering capabilities of the deployment catheter may be used to help direct a transseptal needle through the septum at or adjacent the fossa ovalis under fluoroscopic guidance. While more than one guidewire may be used to gain access, transseptal guidewire 1544 can eventually be positioned in the left atrium, and the deployment catheter 1540 can be advanced over the wire into the right atrium RA as shown in FIG. 35A. As can also be understood with reference to that figure, advancing of the valve from the IVC toward the septum may be facilitated by articulating one or more segments of the deployment catheter using the balloon array articulation systems described above.

For many patients, the fossa ovalis may be between 5 and 14.5 mm above (caudally of) the ostium of the IVC. Craniocaudal and antero-posterior fossa ovalis diameters may be 12.1±3.6 and 14.1±3.6 mm, respectively; the ostium of the IVC may have a diameter between about 18 mm and 30.2 mm, as detailed in an article entitled "Anatomy of the true interatrial septum for transseptal access to the left atrium" by Wieslawa Klimek-Piotrowska (Annals of Anatomy 205 (2016) 60-64), which may be accessed at: http://www.heart-.cm.uj.edu.pl/documents/104468614/110577839/Anatomy %20of%20the %20true%20interatrial %20septum %20for %20transseptal %20access %20to %20the.pdf the full disclosure of which is incorporated herein by reference. Within the separation space between the ostium of the IVC and the fossa ovalis (or other septal penetration site), the segments of catheter 1540 that are resident while gaining access and/or during a valve positioning or deployment may provide a controlled lateral bend angle in a range between about 60 to about 120 degrees, more typically between 70 and 110 degrees, and often of between about 80 and 100 degrees. Pediatric patients may benefit from deployment catheters capably of tighter bend radii, while larger patients and patients with enlarged hearts may use larger diameter catheters having larger bend radii.

Referring now to FIGS. 35A and 35B, while prosthetic valve 1550 is being advanced from the IVC and thru the right atrium, lateral beding of a distal segment 1552 of deployment catheter 1540 may help orient the valve to follow guidewire 1544 toward the left atrium LA. In some embodiments, while the dilation tip adjacent the valve engages the septum the catheter proximal of most or all of the distal segment may be braced against the opposed wall of the right atrium. Optionally, a more proximal segment may anchor the catheter in the IVC. Regardless, axial elongation of distal segment 1552 may help advance the valve into and/or through the septum, with or without distal advancement of a proximal, unarticulated portion of the catheter. In other embodiments, manual or automated advancement of the proximal portion of the catheter into the patient through an introducer valve may be used to move the valve from the right atrium RA to the left atrium LA. As the valve advances within the left atrium, distal segment 1552 may be driven to straighter configuration, and a more proximal segment (such as intermediate segment 1554) may be driven to bend about 80-100 degrees to span from the IVC to the septal crossing site.

Referring now to FIGS. 35B and 35C, when valve 1550 and some, most, or all of distal segment 1552 are within the left atrium LA, a proximal segment 1556 may be driven toward a helical or serpentine anchor configuration within the IVC, with the opposed bends of the segment having a nominal diameter that is larger than that of the surrounding IVC. In other embodiments, an alternative anchor may be employed, such as an elastic balloon that expands from one side of catheter 1540 proximal of the articulated segments, extending a loop of wire laterally from the catheter, or the like. The anchoring engagement between the IVC and catheter 1540 may provide a stable base for articulation of articulation segments that are distal of the anchor. In some embodiments, intermediate segment 1554 or another part of the catheter distal of the anchor may engage a surface of the right atrium opposite the septum. The catheter distal of the anchor will also engage heart tissue of the septum (optionally along the distal or intermediate segment), and these heart tissues may, to some extent, help stabilize the valve. The native mitral valve will move during beating of the heart, and the heart tissues engaging the catheter proximally of the valve may also move with physiological movement that differs from that of the mitral valve.

Figure 36A:
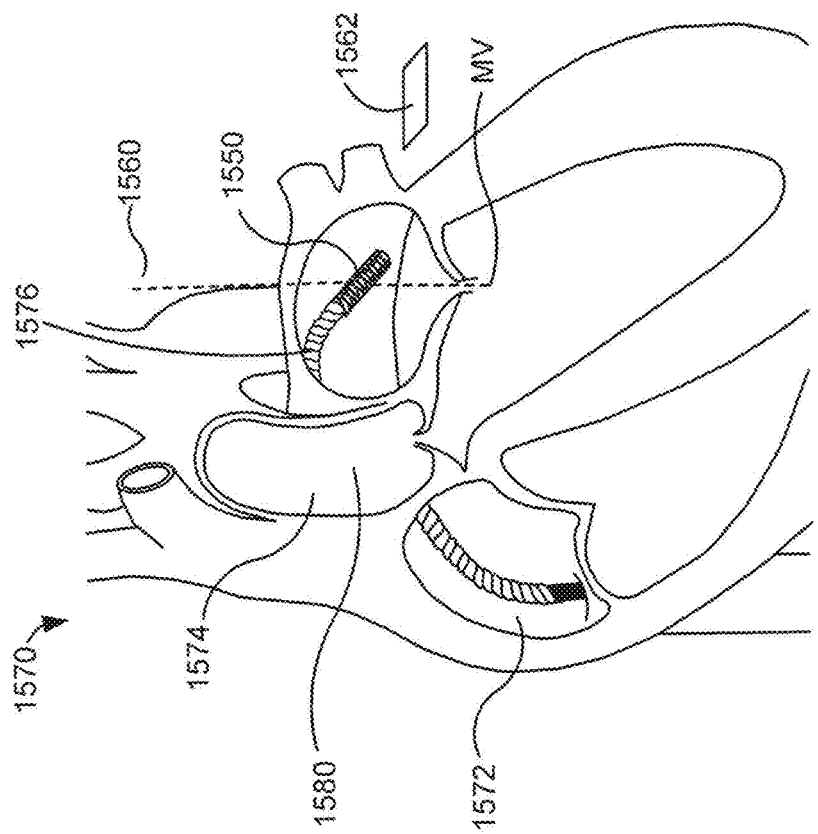
Figure 36C:
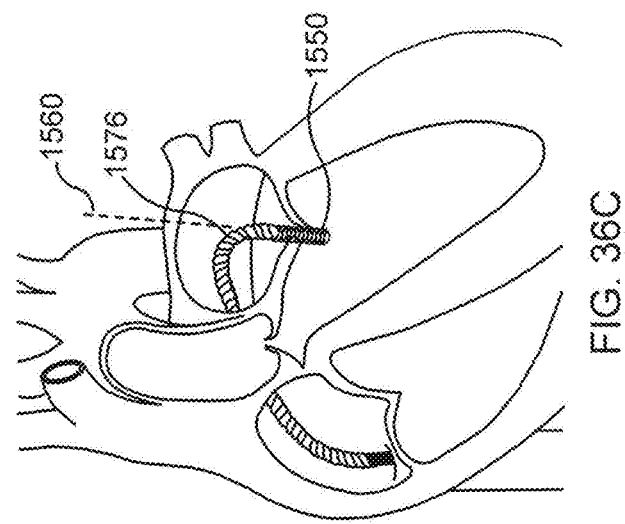
Figure 36B:
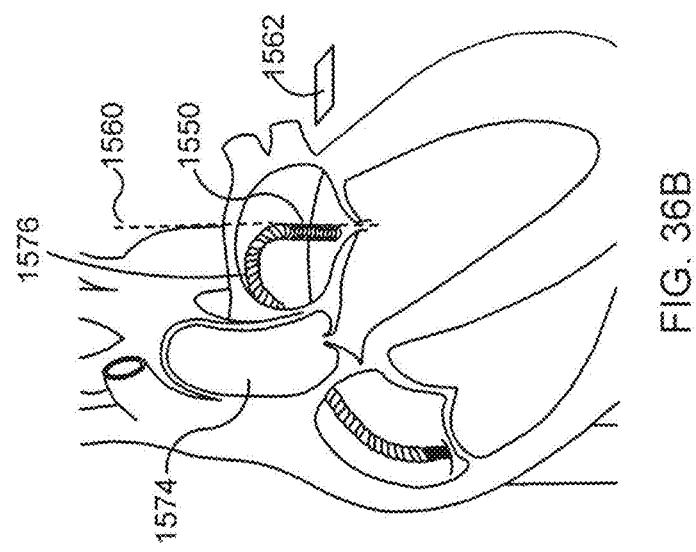

Referring now to FIGS. 36A-36C, exemplary movements of a three segment articulated catheter system for positioning of prosthetic valve 1550 within a mitral valve MV can be understood. Mitral valve MV has an axis 1560, and a valve plane 1562 can be defined by the valve annulus, with the valve plane optionally being perpendicular to the axis. In some embodiments, prosthetic valve 1550 may be axisymmetric, so that desired positioning of the prosthetic valve can be defined by five degrees of freedom relative to the native valve. In other embodiments, the valve structure may be adapted to allow a relatively wide range of axial positioning, so that 4 accurate degrees of freedom are sufficient. In other embodiments, including those having a non-circular prosthetic valve cross-section or a non-planar prosthetic valve seat, six accurate degrees of freedom may be desired. Regardless, deployment system 1570 is shown here with a distal articulated portion having three independently articulatable axial segments 1572, 1574, and 1576 that may each be articulated in two or three degrees of freedom (DOFs) to position prosthetic valve 1550 as desired relative to the native tissues of mitral valve MV. In alternative embodiments, a proximal anchor segment may be used with an intermediate and a distal segment that can each be articulated with 3 DOFs. In still further alternatives, a single 3 DOF segment system may extend through a conventional steerable transseptal catheter.

As can be understood with reference to FIGS. 35C and 36A, it may be desirable to initially advance the distal end of prosthetic valve 1550 beyond the target deployment position, and then to lift the proximal end of the valve caudally within the right atrium. Toward that end, intermediate segment 1574 may curve upward, and distal segment may retract axially and bend downward as shown. As can be understood with reference to FIGS. 36A and 36B, as the axis of prosthetic valve 1550 comes into alignment with axis 1560, the prosthetic valve may remain above the plane 1562 of the native valve tissues. The proximal, intermediate, and distal segments 1572, 1574, 1576 may curve laterally as desired into and/or out of the plane of the images shown so as to bring the prosthetic valve into alignment, with the catheter pivoting about the transseptal axis site 1580, sliding axially through the site 1580, and/or gently laterally displacing cite 1580. As can be understood with reference to FIGS. 36B and 36C, once the distal end of prosthetic valve 1550 has been aligned with the opening of the valve the intermediate segment 1574 can be driven to straighten and then curve downward. Distal segment 1576 may straighten somewhat, and segment(s) 1572, 1574, and/or 1576 may axially elongate to finalize axial alignment and also to axially advance the prosthetic valve to the desired position relative to the plane of the native mitral valve tissues. The valve can then be deployed, often by balloon expansion, proximal retraction of a surrounding sheath, or the like.

Regarding the articulation capabilities of the distal segments, the segments may have similar structures, bend radii, elongation capabilities, and the like. Bending angles and space constrains for the segment(s) spanning the right atrium are described above. For the segment(s) moving within the left atrium, the size of the left atrium may increase with diseases associated with valve disease. As explained in, for example: https://web.stanford.edu/group/ccm_echocardio/cgi-bin/mediawiki/index.php/Left_atrium_dimensions, in a four chamber sonography view the left atrium may have a diameter of between about 28 and 40 mm and a major axis of from about 41 to 61 mm; these dimensions may increase by as much as 100% or more in a severely dilated heart. The articulated catheter segment(s) within the left atrium (usually including most or all of the distal segment, and optionally including a portion of the proximally adjacent segment) will accommodate bends of from 80 to 120 degrees when extending from the transseptal access site, and then bending to extend along the axis of the mitral valve (which may be found at a separation distance of less than one half the LA diameter from the septal wall). Elongation capabilities of each elongatable segment will preferably be at least 5% of the length of that segment in its shortest configuration, often being at least 10% and ideally being 12.5% or more. Articulated portion lengths (in the short configuration, where elongatable, and including all segments and connections therebetween) for valve delivery and/or other valve therapies may be from 2.5 in. to about 11 in., often being between about 4.5 and 8.5 inches.

Figure 37:
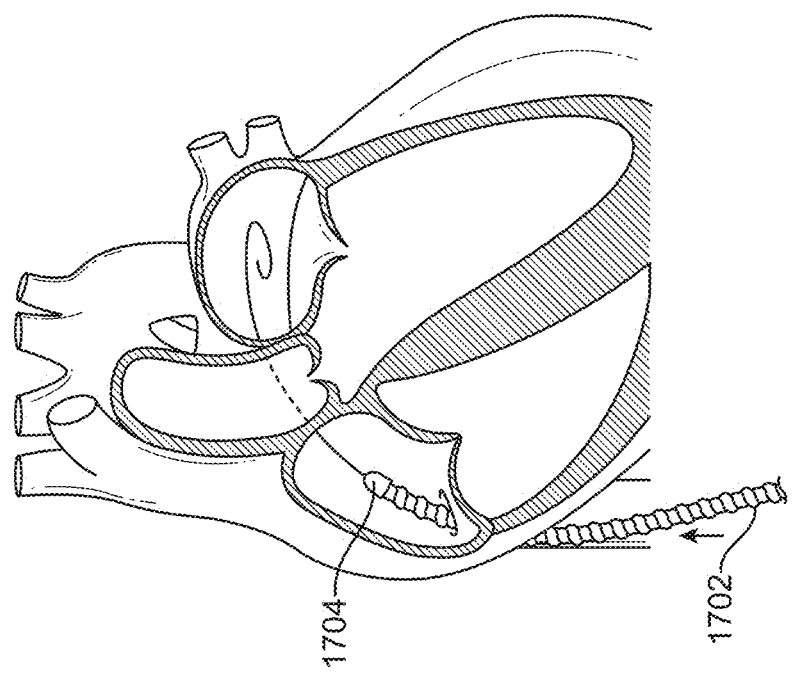
FIGS. 37 and 38 schematically illustrate advancing a cardiac arrhythmia ablation electrode catheter transseptally over a guidewire and into a left atrium.
Figure 38:
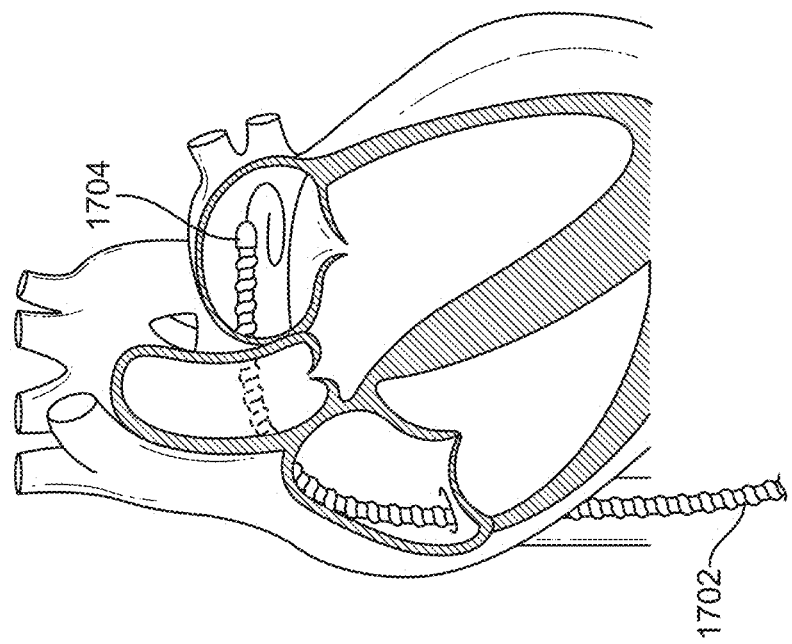
Figure 39:
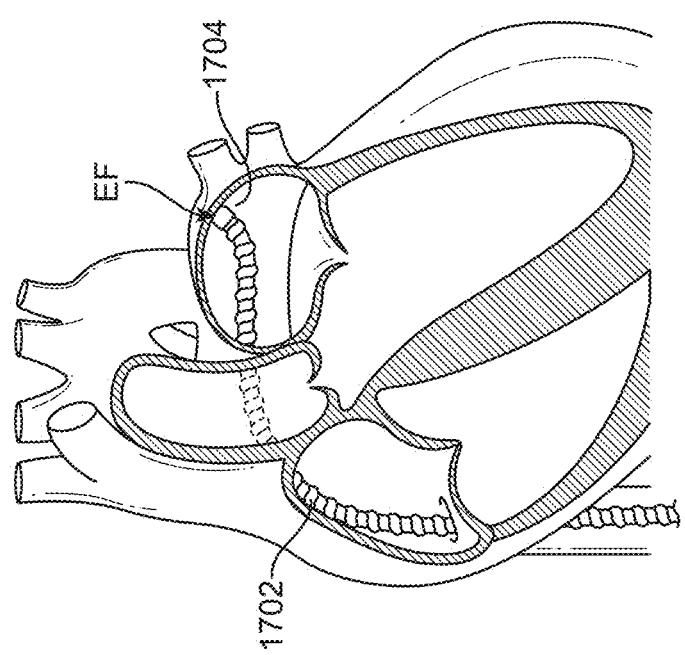

Referring now to FIGS. 37-39, a cardiac ablation catheter 1702 may be introduced into the right atrium via the IVC, and may be advanced transseptally to the left atrium with an approach analogous to the advancement of a valve deployment system described above. The body of catheter 1702 may have a profile of from 5 Fr to about 15 Fr, more typically having a profile of from 8 Fr to 12 Fr. A distal articulatable portion may have from 1 to 4 independently articulatable segments, optionally having one or two segments articulatable in two transverse lateral degrees of freedom with a range of motion of at least 120 degrees, more typically being at least 180 degrees (including 90 degrees to each side, such as +X, −X and +Y, −Y for each segment), and ideally being at least 240 degrees (120 degrees to each side) within the left atrium (or other chamber of the heart to be treated) so as to be able to engage an electrode 1704 against target regions of the endocardial heart tissue, often including at least throughout an ablation pattern sufficient to isolate the ostia of the pulmonary arteries.

A segment proximal of the laterally articulatable segments may be configured to function as an anchor segment as described above (such as for anchoring in the IVC) or a conventional lateral balloon or pull-wire anchor may be included on the catheter body or a surrounding sheath, and there may be a non-articulated portion or limited-capability articulated segment between the anchor and the electrode positioning segments (such as a segment that articulates laterally in only one orientation (i.e., +X only), or that bends passively and can be controllably elongated). Electrode 1704 may comprise, for example, a cooled 8 Fr electrode having passages for saline (or other conductive cooling fluid) to be transmitted therethrough, as is included on known cardiac ablation catheter systems. As shown in FIG. 39, engagement between the electrode and tissue will typically have an associated engagement force vector EF. Electrode ablation efficacy may benefit from engagement forces in a range over 20 gr (with engagement forces measured using a Force Time Integral or FTI, as can be understood with reference to http://circep.ahajournals.org/content/7/1/5.full. Advantageously, engagement pressure may be measured by monitoring the balloon pressure via the balloon inflation channels extending to the proximal end of the catheter, as explained above. Engagement pressures below a maximum desired force threshold may also be beneficial so as to inhibit tamponade of the electrode, with suitable maximum force thresholds optionally being in a range from about 40 to about 75 gr, typically being about 50 gr. Additionally, the orientation of the engagement force vector EF can be identified by differential pressures of the channels, as also described above. It will often be desirable to provide an indication of the engagement pressure magnitude and/or orientation to the user via a display, warning light, speaker, haptic vibration generator, or other output of the system. Compliance of the segments may be tailored to maintain engagement forces in the desired range despite physiological movement during a procedure, such as by controlling antagonistic balloon inflation pressures or selectably inflating with gas, liquid, or a desired mixture of both in one or more of the balloon inflation channels. Still further options include automatically releasing pressure when engagement force exceeds (or will exceed) the maximum desired threshold, or the like.

Figure 40:
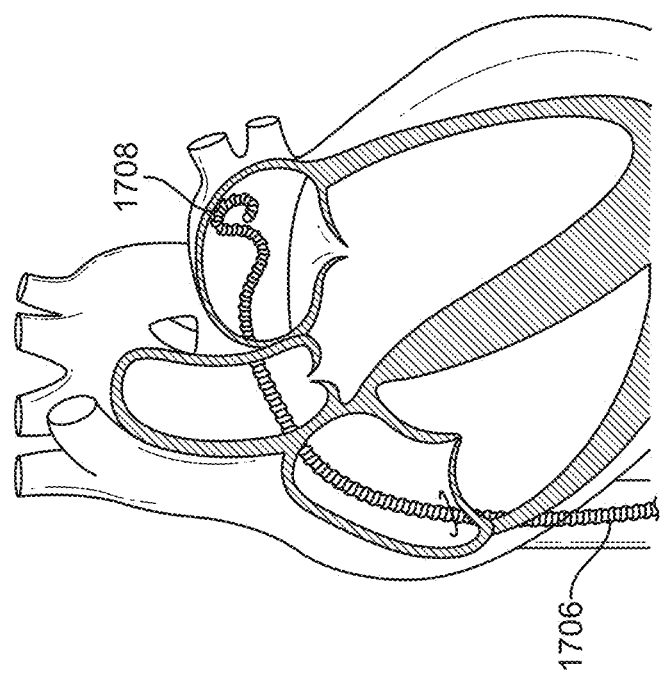
FIGS. 39 and 40 schematically illustrate robotically steering a cooled ablation electrode and diagnostic electrode loop within a left atrium of a heart, and measuring engagement forces between the electrode(s) an endocardial tissue surface via pressure signals.

Referring now to FIG. 40, diagnostic electrode catheter system 1706 may include one or more articulating segments proximal of an electrode array 1708, and the array may be urged to a desired configuration (such as the round barber pole lasso configuration shown) either resiliently, by a pull wire, or by articulation balloons. Diagnostic electrode array catheters may have smaller profiles than many ablation catheters (such as having a profile of from 4 to 7 Fr), and both ablation and diagnostic electrode catheters may be guided at least in part with reference to an electrophysiology guidance map system, such as those available commercially from Biosense Webster, Boston Scientific, St. Jude, Abbott, and others. Still further diagnostic and/or therapeutic tools and catheters may be provided, for example, including a pacing electrode, a catheter for advancement into a coronary sinus, a lead deployment catheter, and/or the like. Note that more than one of these catheter systems may be disposed within the heart simultaneously, for example, with both an ablation electrode catheter and a diagnostic electrode array disposed in the left atrium, while a conventional or balloon-articulated pacing electrode is within the coronary sinus.

Figure 41B:
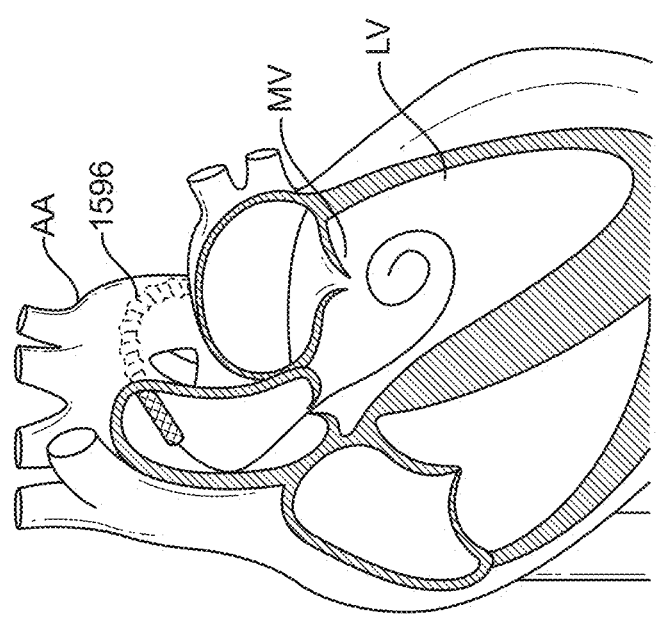
FIGS. 41A and 41B illustrate trans-aortic access to the left ventricle and retrograde treatment of the mitral annulus.
Figure 41A:
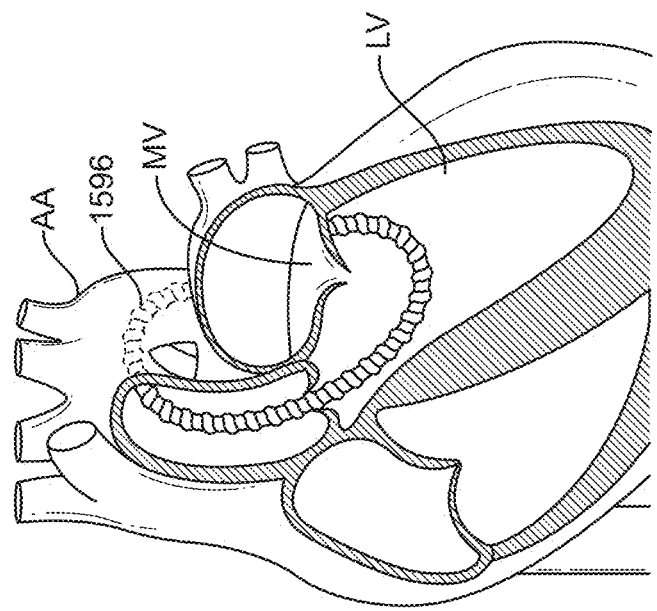

Referring now to FIGS. 41A and 41B, diagnosis and/or therapies of the ventricles may also benefit by modifying existing deployment technology so as to take advantage of the balloon articulated systems described herein. For these and some other procedures, it may be advantageous to access the tissues surfaces apically of the mitral and/or tricuspid valve annulus, and/or other tissues within the left and right ventricles. Access to the left ventricle can be obtained by advancing a distal end of a transseptal catheter down through the mitral valve and then articulating one or two distal segments of the catheter within the ventricle using a retrograde approach. An alternative retrograde approach is illustrated in FIGS. 41A and 41B, in which a multi-segment balloon articulated catheter 1596 is articulated to facilitate across the aortic valve and into the left ventricle LV over a guidewire. One or two distal segments are then driven angles in a range from 120 to 270 degrees to provide retrograde access to the lower annulus tissues of the mitral valve MV. Similar access may be provided for an ablation electrode for treatment of arrhythmias associated with tissues of the ventricles. Access to the tissues along the right ventricle may be accessed by, for example, advancing a catheter into the right atrium via the IVC, and bending the segment(s) in the right atrium toward and through the opening of the tricuspid valve, or more directly by approaching the right atrium via the superior vena cava and proceeding downward.

Figure 42A:
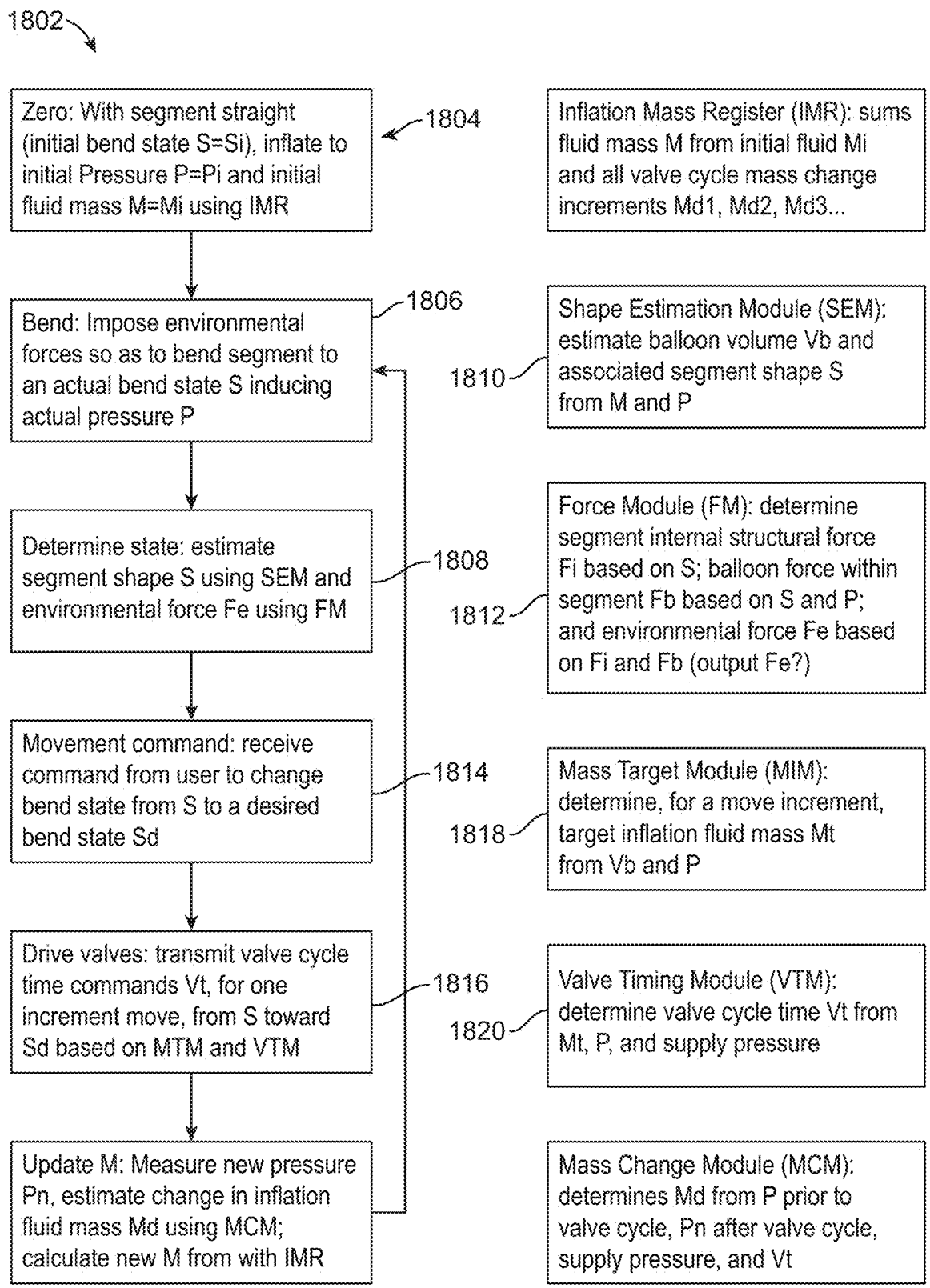
FIGS. 42A-42C are flow charts schematically illustrating methods for determining valve actuation commands based on the mass of inflation fluid transmitted to an array of actuation balloons.
Figure 42B:
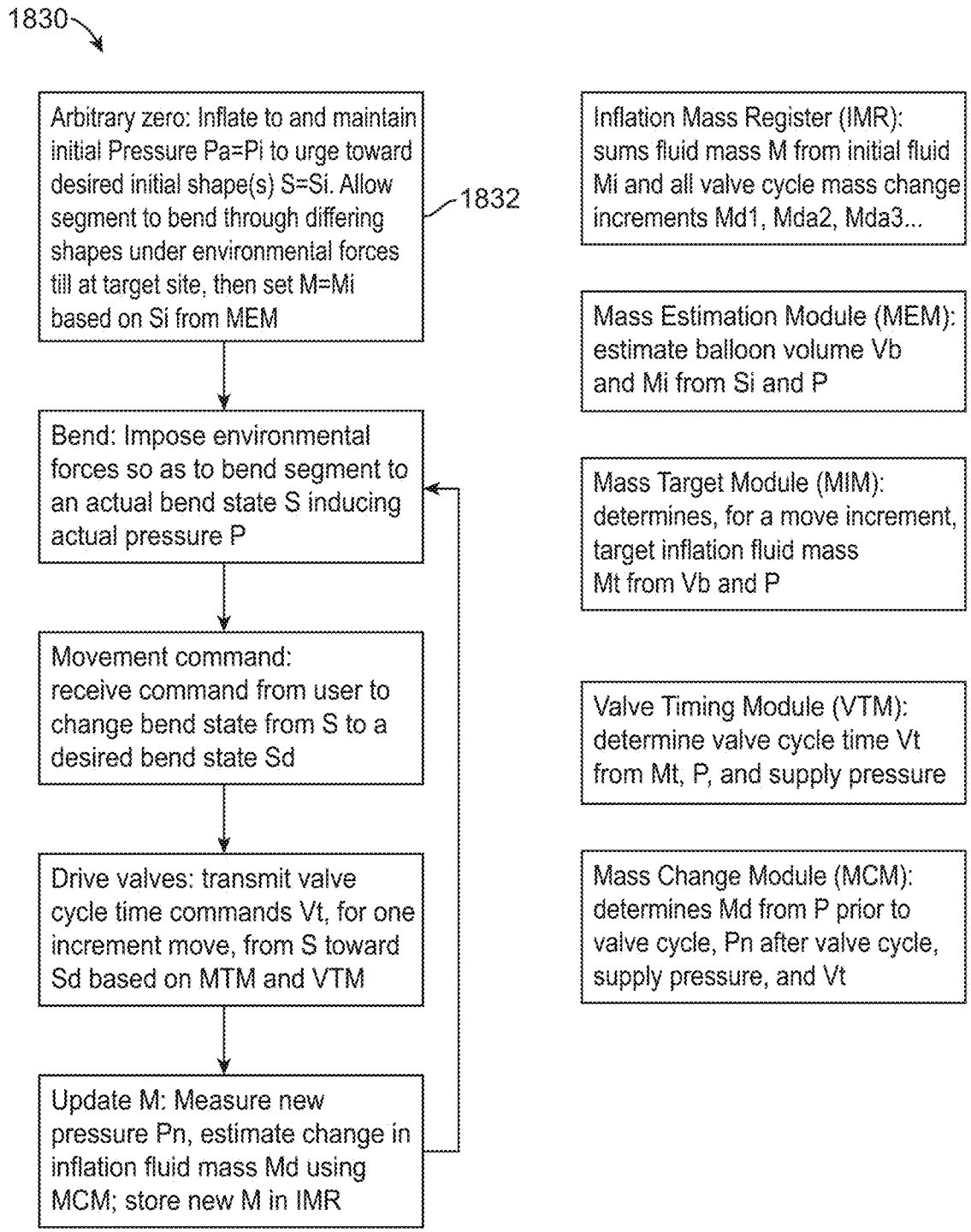
Figure 42C:
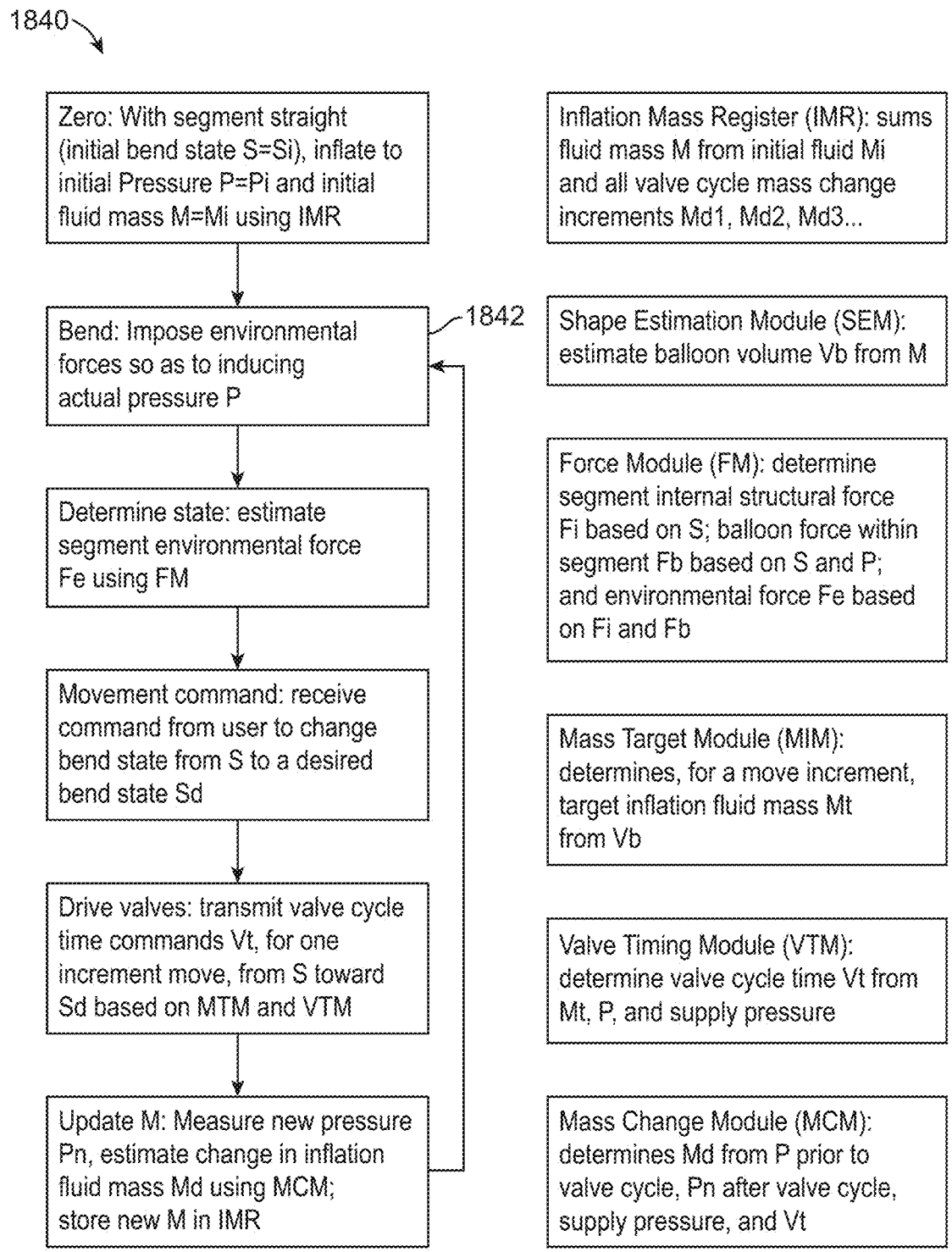

Referring now to FIGS. 42A-42C, flow charts illustrate methods for determining valve commands based in-part on a mass of inflation fluid directed to fluid expandable bodies, most often to subsets of balloons included in an actuation balloon array. As can be understood with reference to FIG. 42A, a first exemplary valve command derivation method and processor 1802 calculates valve command cycle times Vt by tracking a mass of liquid or gas inflation fluid transmitted to and from one or more groups of balloons, and may also be used to estimate environmental forces Fe imposed against a catheter. An initial mass of inflation fluid Mi is introduced into the balloon channel (including the balloons and associated lumens, connectors, sensors, etc. downstream of the valves) by restraining the segment in a predetermined bend state Si (typically straight, but optionally in some alternative shape such as a center of motion or the like) and inflating the balloons and channel to a desired initial pressure Pi. This setting of the initial mass state is sometimes referred to as zeroing the mass 1804, and is analogous to the moving of a joint to a known initial or time zero location.

During use (after zeroing of the segment(s)), environmental forces Fe (such as those associated with tissue or blood pushing against the catheter along or distal of the segment, acceleration of the catheter with heartbeat, breathing, or other physiological movement, and the like) will typically bend the segment 1806. This bending of the segment can change the volume of the balloons along the segment, resulting in a change in pressure P. Changes in pressure may be significant in systems using incompressible inflation fluids such as saline, water, or other liquids, and/or by keeping a ratio between balloon volumes and total channel volume below a threshold. In such systems, a bend and/or force state of the segment(s) can be determined 1808. More specifically, a shape estimation module 1810 may estimate balloon volume Vb and associated segment shape S from the inflation fluid mass in the segment M, the pressure P, and optionally with the geometry of the balloons, channels, and balloon engagement surfaces of the segment, and the compliance of the balloons and channel, and/or with empirical testing of the segment and similar structures. A force estimation module 1812 can determine environmental forces Fe from the differences between internal structural segment forces Fi, and from forces imposed by the balloons Fb. Balloon forces may be determined empirically and/or from the geometry of the balloons (associated with shape S of the segment), preferably with accommodation for the changes in balloon/frame engagement area with differing frame offsets. Internal structural forces Fi may similarly be calculated, but may benefit from empirical measurement of external forces to achieve differing segment states without balloon inflation.

The catheter and other flexible bodies described herein will typically be articulated under computer control, often per the input of a user, with the movement command being received by the processor 1814 to bend from the current bend state or configuration S to a desired bend state Sd. Commands to cycle the valves can be determined and transmitted so as to generate the desired segment movement 1816. Preferably, the commands will be simple binary commands (open/close) with a valve cycle time Vt suitable to allow the desired mass flow through a solenoid or other open/close valve structure. The target inflation fluid mass flow increment Mt may be determined in a mass target increment module MIM 1818 from the balloon volume Vb and current balloon channel pressure P. Note that it may be beneficial to determine inflation fluid mass increments for the current bend state so as to produce even movement increments (i.e., to avoid larger movement increments near the center of the range of motion and smaller movement increments near the ends of the range). A valve timing module 1820 can determine the appropriate valve cycle time Vt using the mass increment target Mt, the balloon pressure, and optionally the supply pressure and exhaust pressure (to obtain the difference in pressures across the valves). Estimates of the mass of inflation fluid transiting the valves during cycling Md may be calculated by measuring pressures after the cycle (such as by determining an average pressure across the valve during flow) together with the valve cycle time Vt, and this estimate of the flow can be used to update the mass of the inflation fluid in the balloon channel(s). The bending 1806, command 1814, and calculations can be repeated throughout an articulation or series of movements of the catheter.

A variety of alternative valve command processor modules could be employed by the systems described herein, and related processors and methods can be understood with reference to FIGS. 42B and 42C. In the valve command method and process arrangement of FIG. 42B, a simplified system makes use of a compressible inflation fluid such as nitrous oxide, $CO_2$, or an alternative gas. Rather than zeroing the system at a controlled bend state, the system maintains a pre-determined pressure during insertion to the worksite 1832. The balloon volume Vb and initial inflation fluid mass Mi are calculated from the pressure and an assumed initial shape of the segment(s) (which may be based on an unconstrained shape the segment at that pressure, so that the estimate benefits from a shape that does not push significantly against adjacent tissue). Simplified inflation fluid monitoring and valve timing calculations may be performed similar to those described above, without calculating catheter/tissue engagement forces based on inflation pressure. Note that engagement forces may instead be determined based on other sensors, optionally from the difference between a relaxed bend state for a given channel mass (as measured empirically or as calculated kinematically) and a measured bend state (as measured with an optical fiber shape sensing system, an image-based shape sensing system, an electromagnetic position sensing system, or the like), combined with known structural stiffness of the segment(s).

Another mass-based control processor and method 1840 is illustrated in FIG. 42, here for use with incompressible inflation fluids. The calculations are simplified somewhat, as the mass of inflation fluid, the associated balloon volume, and the associated segment shape are more tightly coupled, such that the relationships between them vary less with channel pressure and/or with environmental forces. Note that many mass-based fluid articulation control processors and methods (including methods 1802, 1830, and 1840), like many of the related control architectures described above, measure pressure of multiple balloon subsets, and use that pressure to derive feedback on the actual state of the articulated structure, with that feedback either being output to the system user, used to drive the articulated structure toward a desired configuration, or both.

While the exemplary embodiment have been described in some detail for clarity of understanding and by way of example, a variety of modifications, changes, and adaptations of the structures and methods described herein will be obvious to those of skill in the art. Hence, the scope of the present invention is limited solely by the claims attached hereto.

What is claimed is:

1. A method for diagnosing and/or treating an arrhythmia of a heart of a patient, the method comprising:
   introducing an elongate flexible cardiac catheter body into the heart, the catheter body having a proximal end and a distal end with an axis therebetween and an arrhythmia tool mounted near the distal end of the catheter body;
   articulating the catheter body proximal of the tool so as to bend the axis of the catheter body along a lateral bending orientation and align the tool with a target tissue region within the heart by inflating a subset of an array of articulation balloons disposed along the catheter body proximal of the tool;
   wherein the heart including a tissue, wherein the tool is distal of the first subset of articulation balloons, and a fluid source is in fluid communication with the balloons, the fluid source having an inflation fluid; and
   determining, by a processor coupled with the fluid source and with the balloons, an engagement force between the tool and the tissue induced by the bending of the axis of the catheter, wherein the engagement force is determined in response to a pressure of the inflation fluid.

2. The method of claim 1, further comprising controlling, with the processor, the engagement force by varying the bending of the axis using the subset of balloons.

3. The method of claim 2, wherein a plurality of valves couple the balloons with the fluid source, and wherein the controlling of the engagement force comprises controlling, with a feedback system of the processor, articulation of the articulated portion by actuating the valves.

4. The method of claim 1, wherein the tool comprises an ablation electrode or a diagnostic electrode array, and further comprising ablating the engaged tissue or sensing electrical signals of the engaged tissue with the tool.

5. The method of claim 1, wherein a pressure sensor is coupled to the balloons and the processor couples an output to the pressure sensor, further comprising providing, with the output, to a system user, an indication of the engagement force between the electrode and the heart induced by the bending of the axis in response to balloon pressure signals.

6. The method of claim 5, further comprising determining, with the processor and in response to pressure signals from the pressure sensor, an orientation of the engagement force and identifying, to the user, the orientation of the engagement force with the indication.

7. The method of claim 1, further comprising advancing the tool transseptally within the heart.

8. The method of claim 1, wherein the array of the balloons includes a second subset of the balloons, the second subset comprising a plurality of the balloons, and further comprising inflating the second subset so as to induce bending of the axis along a second lateral bending orientation transverse to the first lateral orientation, and wherein the articulated portion includes a first articulated segment and a second articulated segment, wherein the axis along the first segment is bent along the first and second lateral orientations by the first and second subsets, and wherein the axis along the second segment is bent along third and fourth lateral orientations.

9. The method of claim 8, wherein inflation of a third subset of balloons axially elongates the articulated portion.

10. The method of claim 1, wherein a structural skeleton extends along the axis, the structural skeleton having a plurality of axial offsets, the offsets defined by axial separations between distally oriented surface of the structural skeleton and proximally oriented surfaces of the structural skeleton, the balloons disposed within the offsets, wherein the subset of balloons are eccentric and aligned along the axis and the bending of the axis is performed by inflating the subset of balloons so that the balloons urge the proximally oriented surfaces and distally oriented surfaces apart and increasing the offset to bend the axis away from the subset of balloons.

11. A method for diagnosing and/or treating a tissue of a patient, the tissue having a tissue surface, the method comprising:
introducing, into a patient, an elongate flexible catheter body having a proximal end and a distal end with an axis therebetween;
advancing, toward the tissue surface, a diagnostic and/or treatment tool mounted near the distal end of the catheter body;
varying a lateral bend of the axis, in response to user input from the proximal end, along an articulation portion of the catheter body disposed proximal of the tool;
wherein an engagement force between the tool and the tissue surface varies in response to the lateral bend of the axis and induces pressure within a plurality of fluid channels extending along the axis between the proximal end and the tool;
determining, with a processor and in response to the pressure, the engagement force; and
indicating, with an output coupled with the processor and to the user, the force of the engagement;
wherein an array of articulation balloons are disposed along the articulated portion and coupled to the proximal end by the plurality of fluid channels, the engagement inducing a plurality of differing pressures in the balloons in response to an orientation of the engagement force, wherein the output indicates the engagement orientation.

12. The method of claim 11, wherein a plurality of valves couple the processor to the plurality of fluid channels extending along the axis, wherein the processor articulates the catheter body by actuating the valves so as to bend the axis in a plurality of lateral bending orientations, wherein a sensor transmits signals to the processor, the signals comprising feedback signals indicating an articulation state of the catheter body, and wherein the processor is configured to actuate the valves using the feedback signals.

13. An articulation method comprising:
providing:
an elongate flexible body having a proximal end and a distal end with an axis therebetween;
a surface near the distal end of the elongate flexible body;
an articulation balloon array proximal of the surface;
a fluid channel extending along the axis between the proximal end and the balloon array;
a pressure sensor coupled with the channel; and
a processor coupled with the pressure sensor:
varying lateral bending of the axis by inflating a plurality of balloons of the balloon array;
varying an engagement between the surface and a target structure in response to varying of the bending of the axis;
inducing pressure within the channel, the pressure varying with the lateral bending of the axis; and
determining, with the processor in response to pressure signals from the processor, a force of the engagement.

14. The method of claim 13, wherein the processor determines a mass of inflation fluid present in the channel and/or a subset of the balloons in the articulation array, and uses the mass of inflation fluid and a stiffness of the elongate flexible body to determine the force of engagement.

* * * * *